US011311538B2

(12) United States Patent
Bindra et al.

(10) Patent No.: US 11,311,538 B2
(45) Date of Patent: Apr. 26, 2022

(54) COMPOSITIONS AND METHODS FOR TARGETING CANCERS

(71) Applicant: YALE UNIVERSITY, New Haven, CT (US)

(72) Inventors: Ranjit Bindra, New Haven, CT (US); Peter Glazer, Guilford, CT (US); Parker Sulkowski, Guilford, CT (US); Brian Shuch, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 362 days.

(21) Appl. No.: 16/510,122

(22) Filed: Jul. 12, 2019

(65) Prior Publication Data
US 2020/0016156 A1 Jan. 16, 2020

Related U.S. Application Data

(60) Provisional application No. 62/697,872, filed on Jul. 13, 2018.

(51) Int. Cl.
| A61K 31/55 | (2006.01) |
| A61K 31/498 | (2006.01) |
| A61K 31/445 | (2006.01) |
| A61K 31/4196 | (2006.01) |
| A61K 31/4164 | (2006.01) |
| A61P 35/00 | (2006.01) |
| A61K 31/502 | (2006.01) |
| A61K 31/166 | (2006.01) |
| A61K 31/454 | (2006.01) |
| A61K 31/4184 | (2006.01) |
| A61K 31/215 | (2006.01) |
| A61K 31/04 | (2006.01) |
| A61K 31/47 | (2006.01) |
| A61K 31/145 | (2006.01) |
| A61K 31/5025 | (2006.01) |
| A61K 45/06 | (2006.01) |

(52) U.S. Cl.
CPC ............ *A61K 31/502* (2013.01); *A61K 31/04* (2013.01); *A61K 31/145* (2013.01); *A61K 31/166* (2013.01); *A61K 31/215* (2013.01); *A61K 31/4184* (2013.01); *A61K 31/454* (2013.01); *A61K 31/47* (2013.01); *A61K 31/5025* (2013.01); *A61K 31/55* (2013.01); *A61K 45/06* (2013.01)

(58) Field of Classification Search
CPC .... A61K 31/55; A61K 31/498; A61K 31/445; A61K 31/4196; A61K 31/4164; A61P 35/00
USPC ................ 514/215, 248, 250, 323, 383, 396
See application file for complete search history.

(56) References Cited

U.S. PATENT DOCUMENTS

| 6,288,110 B1 | 9/2001 | Marikovsky |
| 2007/0060597 A1* | 3/2007 | Qi .......................... A61P 35/04 |
| | | 514/259.31 |
| 2011/0229479 A1 | 9/2011 | Vogelstein et al. |
| 2014/0377336 A1 | 12/2014 | Brown et al. |
| 2016/0010159 A1 | 1/2016 | Lin et al. |

FOREIGN PATENT DOCUMENTS

| WO | 2015123229 A1 | 8/2015 |
| WO | 2015153498 A1 | 10/2015 |
| WO | 2016044666 A1 | 3/2016 |

OTHER PUBLICATIONS

Baader , et al., "Inhibition of prolyl 4-hydroxylase by oxalyl amino acid derivatives in vitro, in isolated microsomes and in embryonic chicken tissues", The Biochemical Journal, 300 (Jun. 1, 1994), 525-530.
Bai , et al., "Integrated genomic characterization of IDH1-mutant glioma malignant progression", Nat Genet. (Jan. 2016); 48(1): 59-66.
Barletta , et al., "Succinate dehydrogenase-deficient tumors: diagnostic advances and clinical implications", Advances in Anatomic Pathology. 19 (4): 193-203 (Jul. 2012) (Abstract only).
Bindra , et al., "Basal repression of BRCA1 by multiple E2Fs and pocket proteins at adjacent E2F sites", Cancer Biology & Therapy, 5(10), 1400-1407 (Oct. 2006).
Chu , et al., "KDM4B as a target for prostate cancer: structural analysis and selective inhibition by a novel inhibitor", J Med Chem, 57(14), 5975-5985 (Jul. 24, 2014).
Dang , et al., "IDH mutations in cancer and progress toward development of targeted therapeutics", Annals of Oncology : official journal of the European Society for Medical Oncology / ESMO 27(4), 599-608 (Apr. 2016).
Fu , et al., "Glioma-derived mutations in isocitrate dehydrogenase 2 beneficial to traditional chemotherapy", Biochem Biophys Res Commun. 410(2), Jul. 2011, 218-223.
Gross , et al., "Targeting cancer with kinase inhibitors", The Journal of Clinical Investigation, 125(5), 1780-1789 (May 1, 2015).
Intlekofer , et al., "Hypoxia Induces Production of L-2-Hydroxyglutarate", Cell Metab. (Aug. 4, 2015); 22(2):304-11. PubMed PMID: 26212717; PubMed Central PMCID: PMCPMC4527873.
Linehan , et al., "Molecular pathways: Fumarate hydratase-deficient kidney cancer-targeting the Warburg effect in cancer", Clin Cancer Res., (Jul. 1, 2013) 19(13):3345-52. PubMed PMID: 23633457; PubMed Central PMCID: PMCPMC4447120.

(Continued)

*Primary Examiner* — Raymond J Henley, III
(74) *Attorney, Agent, or Firm* — Saul Ewing Amsterin & Lehr LLP; Kathryn Doyle; Domingos J. Silva

(57) ABSTRACT

In various aspects and embodiments the invention provides a method of treating or preventing a cancer in a mammalian subject in need thereof, the method comprising administering to the subject a therapeutically effective amount of at least one compound selected from the group consisting of a DNA repair inhibitor, a DNA strand break repair inhibitor, and a homologous recombination (HR) repair inhibitor, wherein cells in the cancer comprise a fumarate hydratase (FH) and/or succinate dehydrogenase (SDH) mutation.

15 Claims, 37 Drawing Sheets

(56) References Cited

OTHER PUBLICATIONS

Loser, et al., "Sensitization to radiation and alkylating agents by inhibitors of poly(ADP-ribose) polymerase is enhanced in cells deficient in DNA double strand break repair", Molecular Cancer Therapeutics, 9(6), 1775-1787 (Jun. 2010).

Losman, et al., "What a difference a hydroxyl makes: mutant IDH, (R)-2-hydroxyglutarate, and cancer", Genes & Dev, 27(8), 836-852 (Apr. 15, 2013).

Lu, et al., "Hypoxia-Induced Epigenetic Regulation and Silencing of the BRCA1 Promoter", Molecular and Cellular Biology, 31(16), 3339-3350 (Aug. 2011).

Mallette, et al., "RNF8- and RNF168-dependent degradation of KDM4A/JMJD2A triggers 53BP1 recruitment to DNA damage sites", Embo J, (Feb. 28, 2012), 31(8), 1865-1878.

Michels, et al., "Predictive biomarkers for cancer therapy with PARP inhibitors", Oncogene 33, 3894-3907 (2014), published online Sep. 16, 2013.

Oldham, et al., "Hypoxia-Mediated Increases in L-2-hydroxyglutarate Coordinate the Metabolic Response to Reductive Stress", Cell Metab. (Aug. 4, 2015) 22(2):291-303. PubMed PMID: 26212716; PubMed Central PMCID: PMCPMC4526408.

Rohle, et al., "An Inhibitor of Mutant IDH1 Delays Growth and Promotes Differentiation of Glioma Cells", Science 340(6132), 626-630 (May 3, 2013).

Scanlon, et al., "Multifaceted Control of DNA Repair Pathways by the Hypoxic Tumor Microenvironment", Molecular Cancer Research : MCR 12, 1016-1028; published in final edited form: DNA Repair (Amst). (Aug. 2015); 32: 180-189.

Sciacovelli, et al., "Oncometabolites: Unconventional triggers of oncogenic signalling cascades", Free Radic Biol Med. (Nov. 2016) 100: 175-181; PubMed PMID: 27117029.

Shim, et al., "Another small molecule in the oncometabolite mix: L-2-Hydroxyglutarate in kidney cancer", Oncoscience. (May 2015) 2(5):483-6. PubMed PMID: 26097881; PubMed Central PMCID: PMCPMC4468334.

Sulkowski, et al., "2-Hydroxyglutarate produced by neomorphic IDH mutations suppresses homologous recombination and induces PARP inhibitor sensitivity", Science Translational Medicine, (Feb. 2017) 9(375), eaal2463, 32 pages.

Sulkowski, et al., "Krebs-cycle-deficient hereditary cancer syndromes are defined by defects in homologous-recombination DNA repair", Nat Genet. 50(8), Aug. 2018, 1086-1092.

Tateishi, et al., "Extreme Vulnerability of IDH1 Mutant Cancers to NAD+ depletion", Cancer Cell. (Dec. 14, 2015) 28(6): 773-784.

Terunuma, et al., "MYC-driven accumulation of 2-hydroxyglutarate is associated with breast cancer prognosis", J Clin Invest. (Jan. 2014) 124(1):398-412. PubMed PMID: 24316975; PubMed Central PMCID: PMCPMC3871244.

Tran, et al., "Increased sensitivity to radiochemotherapy in IDH1 mutant glioblastoma as demonstrated by serial quantitative MR volumetry", Neuro-oncology 16(3), 414-420 (Mar. 2014).

Wang, et al., "KDM4A Coactivates E2F1 to Regulate the PDK-Dependent Metabolic Switch between Mitochondrial Oxidation and Glycolysis", Cell Reports (Sep. 13, 2016) 16(11), 3016-3027.

Xu, et al., "Oncometabolite 2-Hydroxyglutarate Is a Competitive Inhibitor of a-Ketoglutarate-Dependent Dioxygenases", Cancer Cell (Jan. 18, 2011) 19(1), 17-30.

Young, et al., "Kdm4b histone demethylase is a DNA damage response protein and confers a survival advantage following γ-irradiation", J Biol Chem. (Jul. 19, 2013) 288(29): 21376-21388.

Karpel-Massler et al., "PARP Inhibition Restores Extrinsic Apoptotic Sensitivty in Gioblastoma", PLOS One, Published Dec. 22, 2014, pp. 1-24, DOI:10.1371/journal.pone.0114583.

\* cited by examiner

FIG. 1B

| Specimen | Size | Grade | T stage | M Stage |
|---|---|---|---|---|
| Normal Kidney-1 | - | - | - | - |
| Normal Kidney-2 | - | - | - | - |
| Normal Kidney-3 | - | - | - | - |
| HLRCC-1 Renal Lymph Node | 9 | 3 | T3a | M1 |
| HLRCC-2 Renal Metastases | 10 | 2 | T2 | M1 |
| HLRCC-3 | 16 | 3 | T4 | M1 |
| SDHB Head and Neck PGL-1 | 2 | - | - | M0 |
| SDHB Abdominal PGL-2 | 9.5 | - | - | M0 |
| Papillary RCC, Type 1 -1 | 13 | 2 | T3a | M0 |
| Papillary RCC, Type 1 -2 | 2.1 | 2 | T1a | M0 |
| Papillary RCC, Type 2 -1 | 2.7 | 3 | T1a | M0 |
| Papillary RCC, Type 2-2 | 5 | 2 | T1a | M0 |
| Clear Cell RCC -1 | 8 | 3 | T3a | M0 |
| Clear Cell RCC - 2 | 10.8 | 4 | T3a | M0 |
| Clear Cell RCC - 3 | 11 | 4 | T4 | M0 |
| Clear Cell RCC - 4 | 8.2 | 3 | T3a | M0 |
| Clear Cell RCC - 5 | 8.6 | 2 | T3a | M0 |
| Clear Cell RCC - 6 | 7.5 | 3 | T2a | M0 |
| Clear Cell RCC - 7 | 17 | 1 | T2b | M0 |
| Chromophobe RCC - 1 | 9 | 2 | T2a | M0 |
| Chromophobe RCC - 2 | 17.5 | 3 | T3a | M0 |
| Chromophobe RCC - 3 | 5.5 | 3 | T3a | M0 |
| Renal Oncocytoma - 1 | 6.7 | - | - | - |
| Renal Oncocytoma - 2 | 7.3 | - | - | - |
| Renal Oncocytoma - 3 | 8.5 | - | - | - |

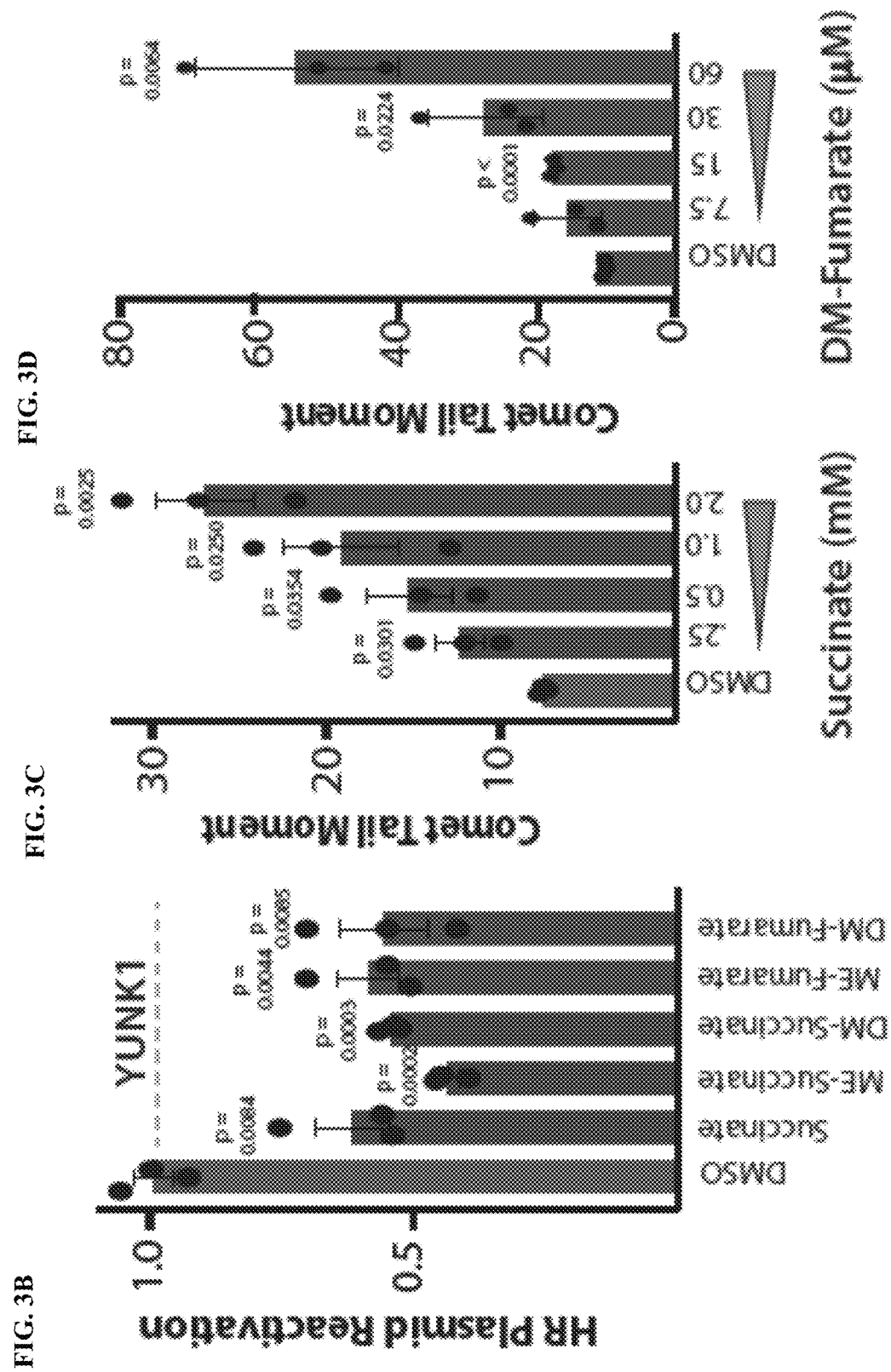

FIG. 5A
FIG. 5B
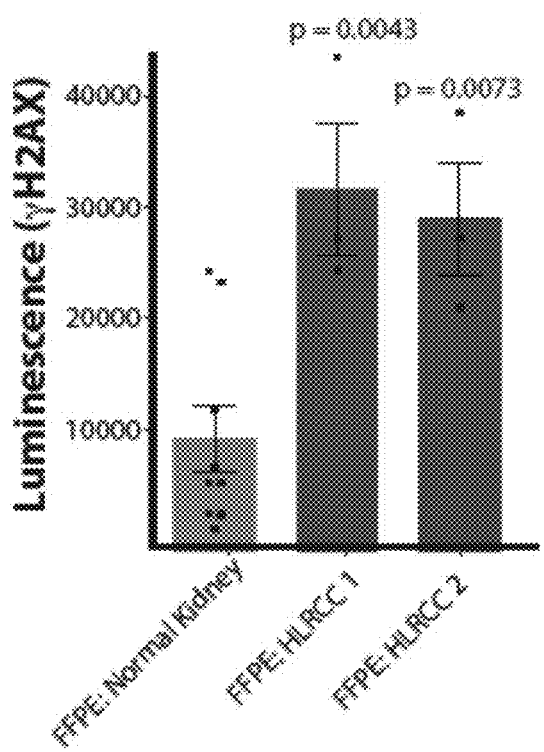
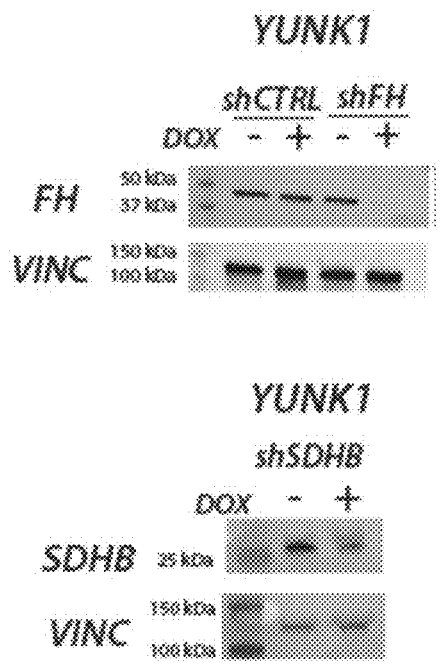
FIG. 5C
FIG. 5D
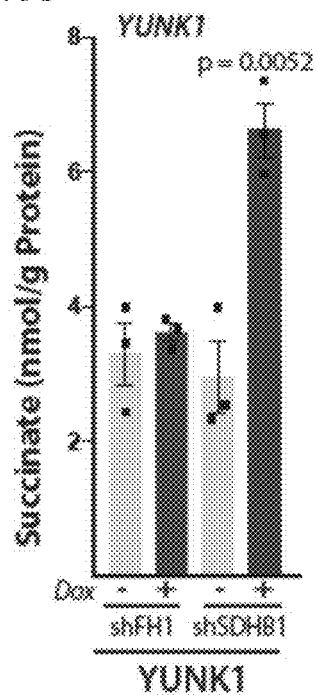
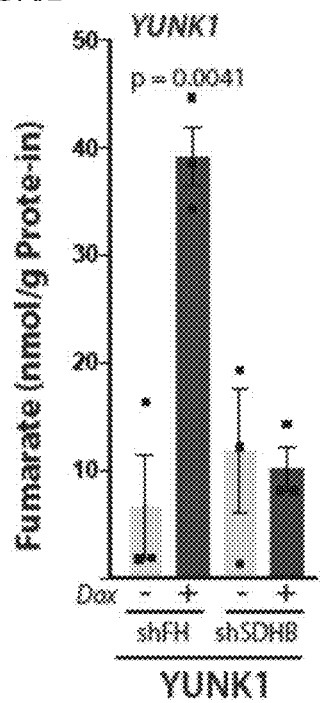

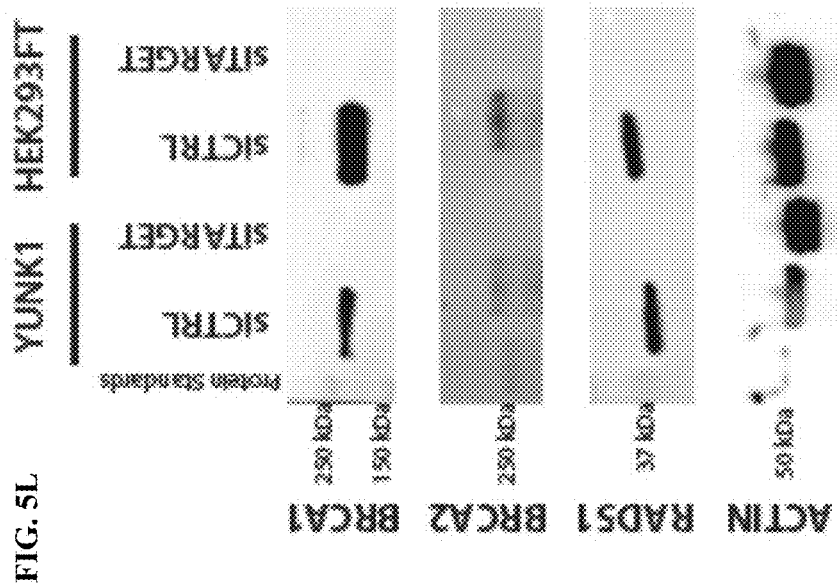
FIG. 5L
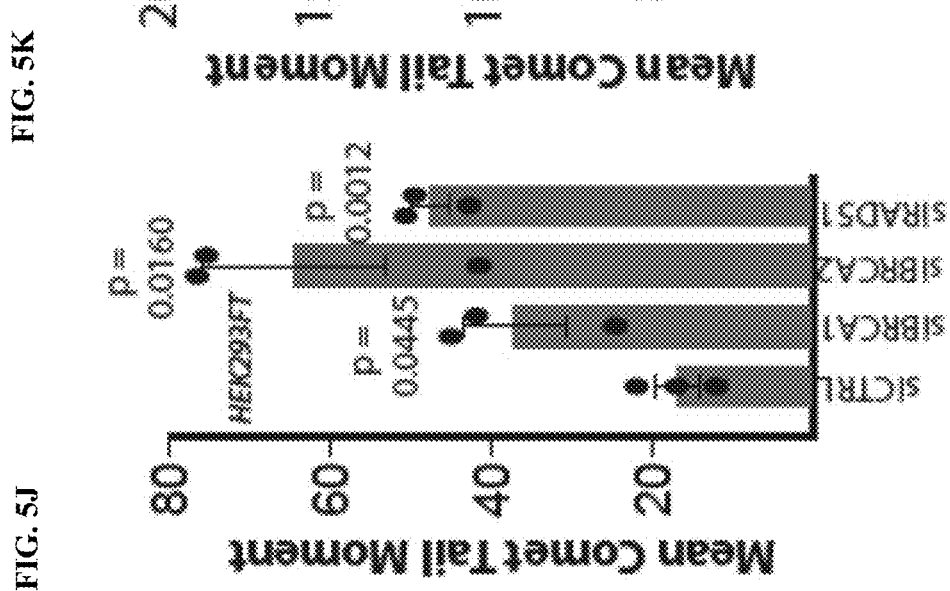
FIG. 5K
FIG. 5J

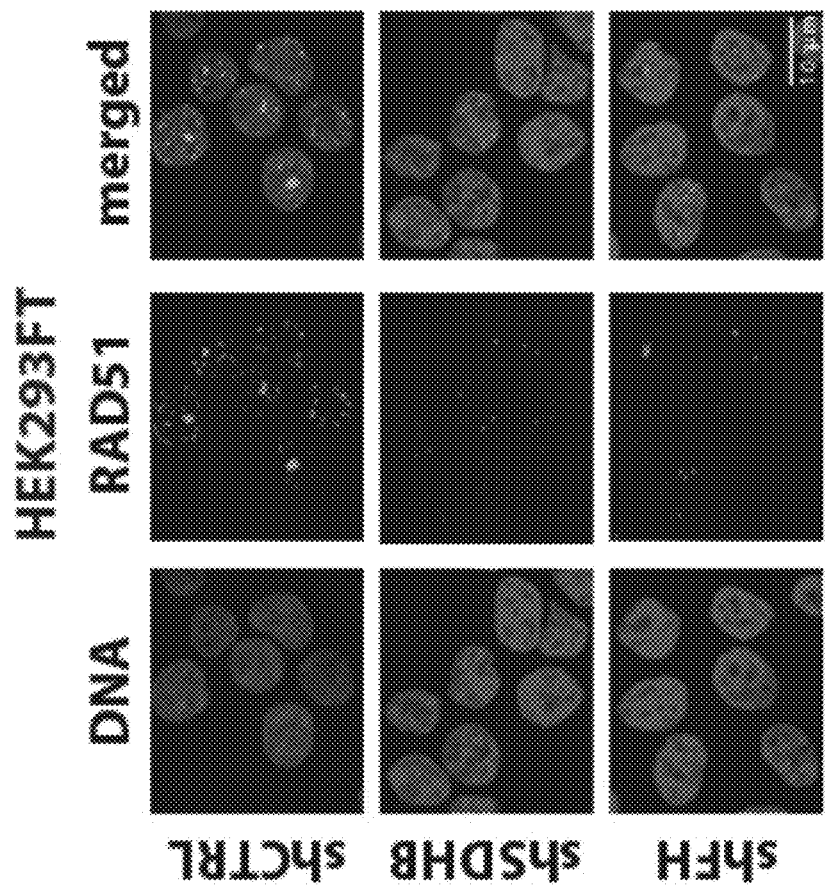
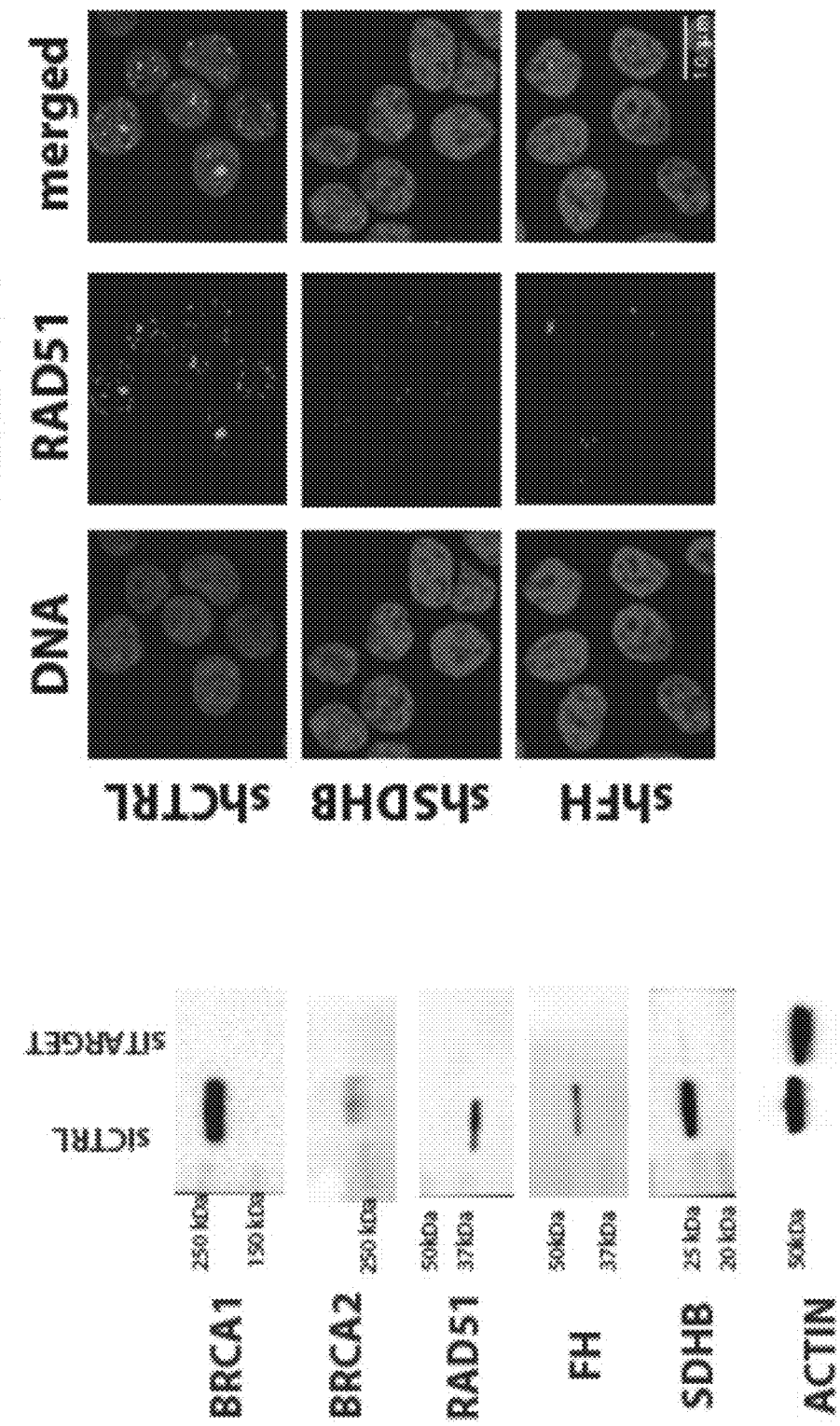

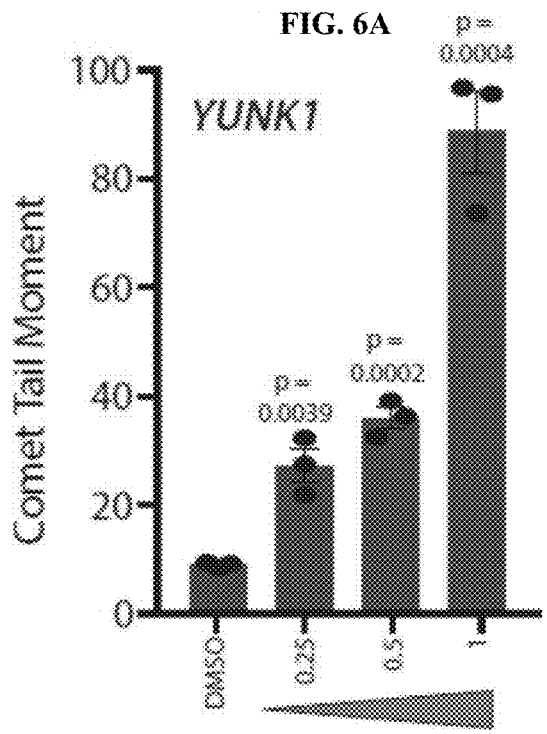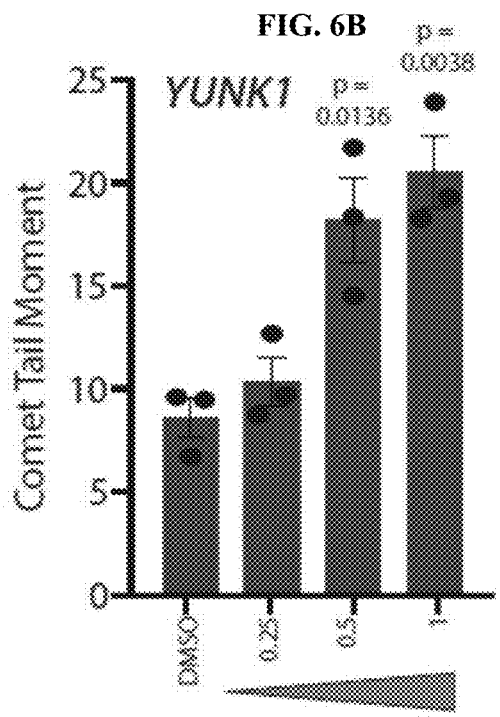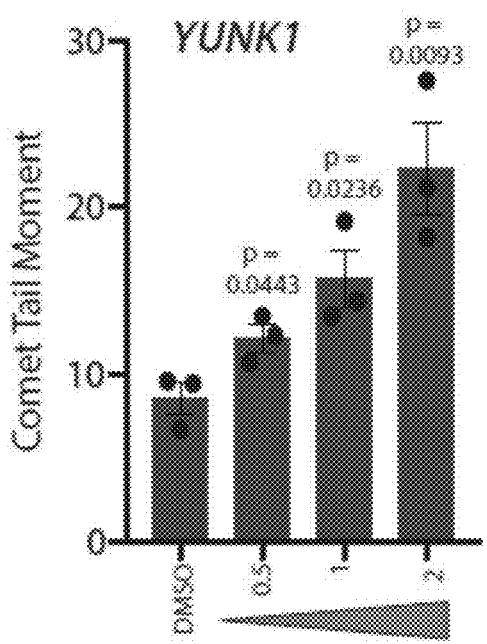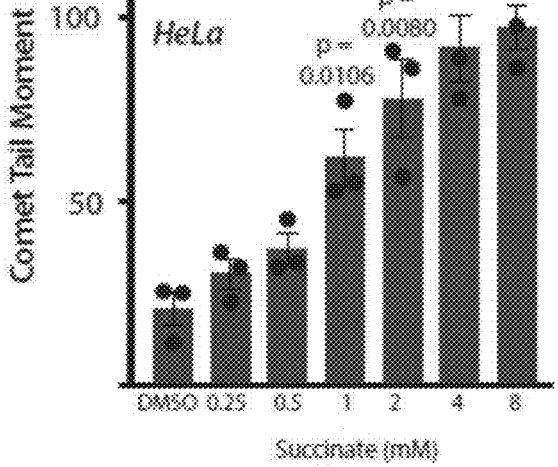

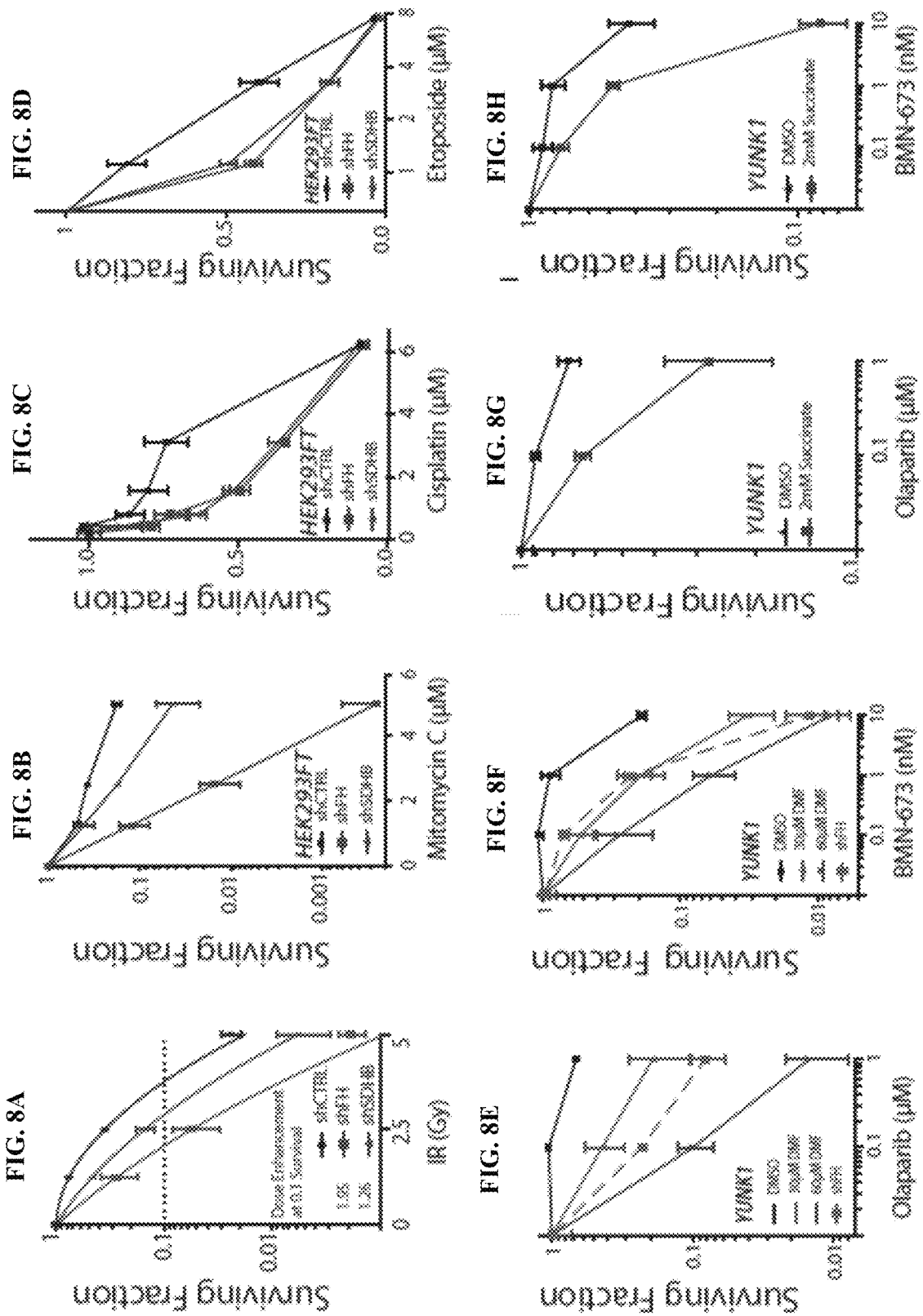

COMPOSITIONS AND METHODS FOR TARGETING CANCERS

CROSS REFERENCE TO RELATED APPLICATIONS

The present application claims priority under 35 U.S. C. § 119(e) to U.S. Provisional Patent Application No. 62/697,872 filed Jul. 13, 2018, which is incorporated herein by reference in its entirety.

STATEMENT REGARDING FEDERALLY SPONSORED RESEARCH OR DEVELOPMENT

This invention was made with government support under grants R35CA197574, R01CA215453, and R01ES005775 awarded by National Institutes of Health. The government has certain rights in the invention.

BACKGROUND OF THE INVENTION

Genomic instability is a hallmark of cancer cells. To maintain genomic stability and ensure high-fidelity transmission of genetic information, cells have evolved a complex mechanism to repair DNA double-strand breaks (DSBs), through homologous recombination (HR). Frequently, the inability to properly coordinate repair of damaged DNA underlies tumorigenesis and disease progression in malignancies. Many human cancer syndromes have been linked to mutations in DNA repair pathway. For instance, germline mutations in the tumor suppressors BRCA1 and BRCA2, two critical HR repair mediators, predispose to both breast and ovarian cancer. However, HR-mediated DNA repair deficiency also sensitizes cancer cells to DNA-damage-inducing therapy such as radiation therapy and DNA-damage-based chemotherapy. One of the most exciting recent therapeutic breakthroughs in cancer is identification of a synthetic lethal interaction between HR repair deficiency and poly(ADP-ribose) polymerase (PARP) inhibition. PARP inhibitors inhibit single-strand DNA repair, which leads to DSBs when DNA replication occurs. Normal cells can repair these DSBs. However, HR repair-deficient cancer cells cannot repair PARP-inhibitor-induced DSBs and die when treated with these drugs. Thus, PARP inhibitors can selectively target HR repair-deficient cancer.

There is a need in the art to develop novel therapeutics which specifically target and exploit the molecular mechanisms related to enzymatic defects and oncometabolite production. There is also a need to identify and develop novel compositions that inhibit DNA repair to render tumor cells sensitive to PARP inhibition. The present invention addresses and meets these needs.

SUMMARY OF THE INVENTION

In one aspect, the invention provides a method of treating or preventing a cancer in a mammalian subject in need thereof, the method comprising administering to the subject a therapeutically effective amount of at least one compound selected from the group consisting of a DNA repair inhibitor, a DNA strand break repair inhibitor, and a homologous recombination (HR) repair inhibitor, wherein cells in the cancer comprise a fumarate hydratase (FH) and/or succinate dehydrogenase (SDH) mutation.

In various embodiments, the cancer is not Hereditary Leiomyomatosis and Renal Cell Cancer (HLRCC) and/or Succinate Dehydrogenase-related Hereditary Paraganglioma and Pheochromocytoma (SDH PGL/PCC).

In various embodiments, the cancer is HLRCC and/or SDH PGL/PCC.

In various embodiments, the at least one compound comprises at least one poly(ADP-ribose) polymerase (PARP) inhibitor selected from the group consisting of olaparib, Iniparib, Niraparib, Veliparib, Rucaparib, 3-aminobenzamide and BMN-673 (Talazoparib), or at least one alpha-ketoglutarate-dependent dioxygenase A or B (KDM4A or KDM4B) inhibitor selected from the group consisting of DMOG, NSC 636819, PK 118 310, NCGC 00247751, NCGC 00244536, NCGC 00247743, IXO1, Disulfiram, and JIB04.

In various embodiments, the subject is further administered at least one antitumor agent. In various embodiments, the antitumor agent is selected from the group consisting of a topoisomerase inhibitor, an alkylating agent, nitrosoureas, an antimetabolite, an antitumor antibiotic, an antimicrotubule agent, a hormonal agent, a DNA strand break inducing agent, an epidermal growth factor (EGF) receptor inhibitor, an anti-EGF receptor antibody, an AKT inhibitor, an mTOR inhibitor, a CDK inhibitor, a tyrosine kinase receptor (TKR) inhibitor, a serine/threonine kinase inhibitor, a phosphatidyl inositol 3-kinase-like (PIKK) protein kinase inhibitor, a DNA dependent protein kinase (DNA-PK) inhibitor, an Ataxia Telangiectasia Mutated (ATM) inhibitor, an Ataxia Telangiectasia and Rad3 Related (ATR) inhibitor, a ribonucleotide reductase inhibitor, and an immune checkpoint inhibitor.

In various embodiments, treatment of the subject with the at least one compound and at least one antitumor agent is synergistic.

In various embodiments, the at least one compound and at least one antitumor agent are co-administered to the subject. In various embodiments, the at least one compound and at least one antitumor agent are coformulated for administration to the subject.

In various embodiments, the subject is further administered radiation therapy. In various embodiments, treatment of the subject with at least one compound and the radiation therapy is synergistic.

In various embodiments, the at least one compound is administered to the subject by a route selected from the group consisting of oral, transdermal, transmucosal, intravesical, intrapulmonary, intraduodenal, intragastrical, intrathecal, subcutaneous, intramuscular, intradermal, intra-arterial, intravenous, intrabronchial, inhalation, pleural, peritoneal, subcutaneous, epidural, otic, intraocular, and topical.

In various embodiments, the cancer comprises at least one selected from the group consisting of brain head and neck cancer, glioma, meningioma, glioblastoma multiforme, lymphoma, leukemia, acute myeloid leukemia (AML), cholangiocarcinoma, multiple myeloma and neuroblastoma. In various embodiments, the cancer comprises glioma, acute myelogenous leukemia or cholangiocarcinoma.

In various embodiments, the mammal is a human.

In another aspect, the invention provides a method of treating a cancer in a mammalian subject in need thereof, the method comprising administering to the subject a therapeutically effective amount of at least one compound selected from the group consisting of fumarate, succinate, and/or analogues or derivatives thereof.

In various embodiments, the cancer (a) does not comprise a FH and/or SDH mutation; and/or (b) is not HLRCC and/or SDH PGL/PCC.

In various embodiments, the at least one compound induces a defect in DNA repair, DNA strand break repair or a homologous recombination (HR) of the cancer cells in the subject.

In various embodiments, the subject is further administered at least one antitumor agent and one poly(ADP-ribose) polymerase (PARP) inhibitor.

In various embodiments, the PARP inhibitor is selected from the group consisting of olaparib, Iniparib, Niraparib, Veliparib, Rucaparib, 3-aminobenzamide and BMN-673 (Talazoparib).

In various embodiments, the antitumor agent is selected from the group consisting of a topoisomerase inhibitor, an alkylating agent, nitrosoureas, an antimetabolite, an antitumor antibiotic, an antimicrotubule agent, a hormonal agent, a DNA strand break inducing agent, an epidermal growth factor (EGF) receptor inhibitor, an anti-EGF receptor antibody, an AKT inhibitor, an mTOR inhibitor, a CDK inhibitor, a tyrosine kinase receptor (TKR) inhibitor, a serine/threonine kinase inhibitor, a PIKK protein kinase inhibitor, a DNA-PK inhibitor, an ATM inhibitor, an ATR inhibitor, a ribonucleotide reductase inhibitor, and an immune checkpoint inhibitor.

In various embodiments, treatment of the subject with the at least one compound, the at least one antitumor agent and the PARP inhibitor is synergistic.

In various embodiments, the at least one compound, the at least one additional antitumor agent and the PARP inhibitor are co-administered to the subject. In various embodiments, the at least one compound, the at least one additional antitumor agent and the PARP inhibitor are coformulated for administration to the subject.

In various embodiments, the method further comprises administration of a PARP inhibitor and a radiation therapy to the subject. In various embodiments, treatment of the subject with the at least one compound and the PARP inhibitor and radiation therapy is synergistic.

In various embodiments, the at least one compound is administered to the subject by a route selected from the group consisting of oral, transdermal, transmucosal, intravesical, intrapulmonary, intraduodenal, intragastrical, intrathecal, subcutaneous, intramuscular, intradermal, intraarterial, intravenous, intrabronchial, inhalation, pleural, peritoneal, subcutaneous, epidural, otic, intraocular, and topical.

In various embodiments, the cancer comprises at least one selected from the group consisting of breast cancer, prostate cancer, ovarian cancer, cervical cancer, skin cancer, pancreatic cancer, colorectal cancer, renal cancer, liver cancer, brain cancer, glioma, meningioma, glioblastoma multiforme, melanoma, lymphoma, leukemia, acute myeloid leukemia (AML), cholangiocarcinoma, lung cancer, endometrial cancer, head and neck cancer, sarcoma, multiple myeloma and neuroblastoma.

In various embodiments, the cancer comprises cells defective in at least one protein selected from the group consisting of BRCA1, BRCA2, PTEN, ATM, ATR, PALB2, FANCD2, RAD50, RAD51, other component of the homology dependent DNA repair pathway or the non-homologous end joining pathway or other component that mediate or regulate DNA repair.

In various embodiments, the mammal is a human.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 1A-1C: High levels of succinate or fumarate in patient-derived HLRCC and PGL/PCC tumors correlate with elevated DNA double-stand breaks. FIG. 1A: Liquid chromatography-mass spectrometry (LC/MS) quantification of succinate and fumarate, as indicated, along with quantification of DNA double-strand breaks (DSBs) by the neutral comet assay in a series of human tumor samples and normal tissue specimens, as indicated. For LC/MS n=1; for neutral comet assay, n=3 replicates per clinical sample; bars represent mean±SEM. FIG. 1B: Clinical characteristics of the patient-derived tumor samples studied. FIG. 1C: Representative images of neutral comet assays as a measure of DNA DSBs performed on the human tumor samples and normal tissues as quantified in FIG. 2A. For each clinical sample the assay was repeated 3 independent times.

FIG. 2A: Western blot analysis of SDHB and FH expression in constitutive shRNA models of SDHB or FH knockdown in YUNK1 cells, as well as in the patient-derived, FH-deficient HLRCC cell lines, UOK 262 (FH −/−), UOK 268 (FH p.His192Asp) and NCCFH1 (FH−/−) This analysis was independently performed 3 times with similar results, and images were cropped around the known molecular weight of the band of interest.
FIG. 2Q: Representative images of RAD51 foci formation upon 2 Gy IR in YUNK1 cells with or without shRNA suppression of SDHB or FH. This analysis was repeated 3 times with quantification shown in FIG. 2P. For FIGS. 2B-2E, 2G, 2H-2I, 2K-2O, and 2P statistical analyses were by two-sided t-test (df=4); bars represent mean of 3 independent experiments±SEM.

FIGS. 3A-3L: High levels of succinate and fumarate suppress homologous recombination and induce elevated DNA double-strand breaks in a pathway mediated by the lysine demethylases, KDM4A and KDM4B. FIG. 3A: Quantification of U2OS DR-GFP HR assay after 24 h treatment with indicated doses of indicated metabolites. FIG. 3B: Quantification of luciferase reactivation by HR in YUNK1 cells after 24 h treatment with 2 mM succinate, 2 mM monoethyl-succinate, 2 mM dimethyl-succinate, 1 mM dimethyl-fumarate, or 60 µM dimethyl-fumarate. FIGS. 3C-3D: Quantification of neutral comet assay performed in YUNK1 cells after 24 h treatment with indicated doses of dimethyl-fumarate (FIG. 3C) and succinate (FIG. 3D). FIG. 3E: Representative images and corresponding quantification of HEK293FT cells treated with 2 mM succinate (Succ) or 30 uM dimethyl-fumarate (Fum) for 24 h prior to immune fluorescence staining for γH2AX or DAPI staining for DNA. This analysis was independently performed 3 times with similar results and quantification is shown in FIG. 3F. FIGS. 3F-3G: Quantification of γH2AX (FIG. 3F) and p53BP1 (FIG. 3G) foci in HEK293FT cells treated with indicated doses of metabolites. FIG. 3H: Quantification of the neutral comet assay performed in UOK 262 and UOK 268 HLRCC cell lines with or without transient transfection with an FH expression construct or after 24 h treatment with the indicated doses of succinate or dimethyl-fumarate or with DMSO control. FIG. 3I: Western blot analysis of histone 3 lysine 36 trimethylation (H3K36me3) and histone 3 lysine 9 trimethylation (H3K9me3) levels in normal kidney and in patient-derived samples of PGL/PCC and HLRCC tumors, with numbering of respective samples corresponding to FIGS. 1A-1C. Actin is used as a loading control and YUNK shSDHB1 is included as a control. This analysis was independently performed 2 times with similar results, and images were cropped around the known molecular weight of the band of interest. FIG. 3J: Quantification and representative images of neutral comet assays performed in HLRCC cell lines, UOK 262 and UOK 268, with or without transfection with expression constructs for FH, KDM4A, KDM4B or KDM4C or treatment with 2 mM dimethyl-α-ketoglutarate (αKG). FIG. 3K: Quantification of neutral comet assay performed in YUNK1 cells treated for 24 h with the indicated doses of metabolites, with or without concurrent transfection with KDM4A expression constructs or with 2 mM dimethyl-α-ketoglutarate treatment. FIG. 3L: DR-GFP assay after treatment with the indicated doses of dimethyl-succinate, dimethyl-fumarate and/or dimethyl-α-ketoglutarate. Statistical analyses were by two-sided t-test (df=4); bars represent mean±SEM of 3 independent experiments.

FIGS. 4A-4B: Clonogenic survival assays in response to the PARP inhibitors Olaparib (FIG. 4A) and BMN-673 (FIG. 4B) in HEK293FT cells with or without knockdown of SDHB or FH, or with or without treatment with 2 mM succinate or 60 µM dimethyl-fumarate, as indicated. FIG. 4N: Non-limiting model of succinate- and fumarate-induced HR suppression via inhibition of KDM4A/B leading to synthetic lethality with PARP inhibitors.

FIG. 5A: Quantification of γH2AX ELISA performed on FFPE normal kidney samples and FFPE HLRCC cases. n=3 for HLRCC samples and n=9 for Normal kidney samples±SEM. Statistical analysis by two tailed t-test, df=10. Dots represent technical replicates. FIG. 5R: Representative images of RAD51 foci formation upon 2Gy IR treatment of HEK293FT cells with or without shRNA suppression of FH or SDHB compared to non-targeted control shRNA. For FIGS. 5C-5D, 5G, 5I-5K, 5M, and 5O, statistical analyses were by two-sided t-test with df=4, and bars represent mean±SEM. For FIGS. 5G-5I, 5M-5N, and 5Q, images were cropped around the known molecular weight of the band of interest and these are representative blots, with each blot repeated independently 3 times with similar results.

FIGS. 6A-6L: Quantification of neutral comet assay results after metabolite treatment of cell lines. FIGS. 6A-6C: Quantification of neutral comet assay performed in YUNK1 cells 24 h after the addition of indicated doses of (FIG. 6A) monoethylfumarate, (FIG. 6B) monoethyl-succinate and (FIG. 6C) dimethyl-succinate to the cell culture medium. FIG. 6D: Quantification of neutral comet assay performed in HeLa cells 24 h after addition of the indicated doses of succinate to the cells. FIGS. 6E-6H: Quantification of neutral comet assay performed in (FIG. 6E) HeLa, (FIG. 6F) HEK293FT, (FIG. 6G) 786-O, and (FIG. 6H) RCC4 cells 24 h after the addition of indicated concentrations of metabolites. FIGS. 6I-6J: Quantification of immunofluorescent γH2AX foci in YUNK1 cells 24 h after the addition of the indicated doses of (FIG. 6I) dimethylfumarate and (FIG. 6J) succinate. FIGS. 6K-6L: Quantification of immunofluorescent p53BP1 foci in YUNK1 cells 24 h after the addition of the indicated doses of (FIG. 6K) dimethyl-fumarate and (FIG. 6L) succinate. For all panels n=3, bars represent mean±SEM and statistical analysis was by two-sided t-test and df=4.

FIG. 7A: Western Blot analysis of histone 3 lysine 36 trimethylation (H3K36me3) and histone 3 lysine 9 trimethylation (H3K9me3), along with total histone 3, in YUNK1 cells with constitutive shRNA knockdown of FH and SDHB, as well as in HLRCC patient derived cell lines, UOK 262, UOK 268, and NCCFH1. Actin was as used as a loading control. FIGS. 7B-7C: Western blot analysis of H3K36me3 and H3K9me3 levels in doxycycline-inducible shRNA knockdowns of FH and SDHB in (FIG. 7B) YUNK1 cells and (FIG. 7C) HEK293FT cells treated with doxycycline for 96 h before collection of cells for western blot analysis. Actin was used as a loading control. FIG. 7D: Western blot analysis of H3K36me3 and H3K9me3, along with total H3, in HEK293FT tumor xenografts harvested for analysis when the tumors were 80 mm$^3$ in size. FIGS. 7E-7F: Western blot analysis of H3K36me3 and H3K9me3 in YUNK1 cells treated with the indicated concentrations of (FIG. 7E) dimethylfumarate or (FIG. 7F) monoethyl-succinate for 24 h. Actin is used as a loading control. Each blot was independently performed 3 times with similar results. For all panels, images were cropped around the known molecular weight of the band of interest.

FIGS. 8A-8L: DNA-repair-inhibitor and DNA-damaging-agent sensitivity in cells deficient in Krebs-cycle enzymes. FIG. 8A: Clonogenic survival assay in HEK293FT shSDHB clone 1 (+doxycycline), HEK293FT shFH clone 1 (+doxycycline) and HEK293FT shCTRL (+doxycycline) after treatment with the indicated doses of ionizing radiation. Dose enhancement ratio at 0.1 survival is indicated. FIGS. 8B-8D: Clonogenic survival assay in HEK293FT shSDHB clone 1+doxycycline, HEK293FT shFH clone 1+doxycycline, and HEK293FT shCTRL+doxycycline with the indicated doses of (FIG. 8B) mitomycin C, (FIG. 8C) cisplatin, and (FIG. 8D) etoposide. FIGS. 8E-8F: Clonogenic survival assay with the indicated doses of (FIG. 8E) Olaparib and (FIG. 8F) BMN-673 for YUNK1 cells also treated or not with 30 µM or 60 µM of dimethyl fumarate, as indicated, or with doxycycline to induce FH knockdown. FIGS. 8G-8H: Clonogenic survival assay with the indicated doses of (FIG. 8G) Olaparib and (FIG. 8H) BMN-673 for YUNK1 cells also treated or not with 2 mM succinate. FIG. 8I: Clonogenic survival assay in YUNK1 cells with constitutive shRNA knockdown of FH and SDHB in response to BMN-673. FIG. 8J: Clonogenic survival assay of cell lines of renal origin treated with indicated doses of mitomycin C. FIGS. 8K-8L: Clonogenic survival assay in response to BMN-673 in HeLa cells also treated or not with (FIG. 8K) 2 mM succinate or (FIG. 8L) 1 mM monoethyl-fumarate or 60 µM dimethyl-fumarate. For all panel n=3, dots represent mean±SEM.

(FIG. 9A) Western blot image and (FIG. 9B) quantification of total cellular poly-ADP-Ribose (PAR) levels in HEK293FT tumor samples 24 h after treatment with the indicated concentrations of BMN-673. n=6 replicates; bars represent mean±SEM. Statistical analysis by two-sided t-test with df=10. For FIG. 9A, images were cropped around the known molecular weight of the band of interest.

DETAILED DESCRIPTION OF THE INVENTION

Figure 1A:
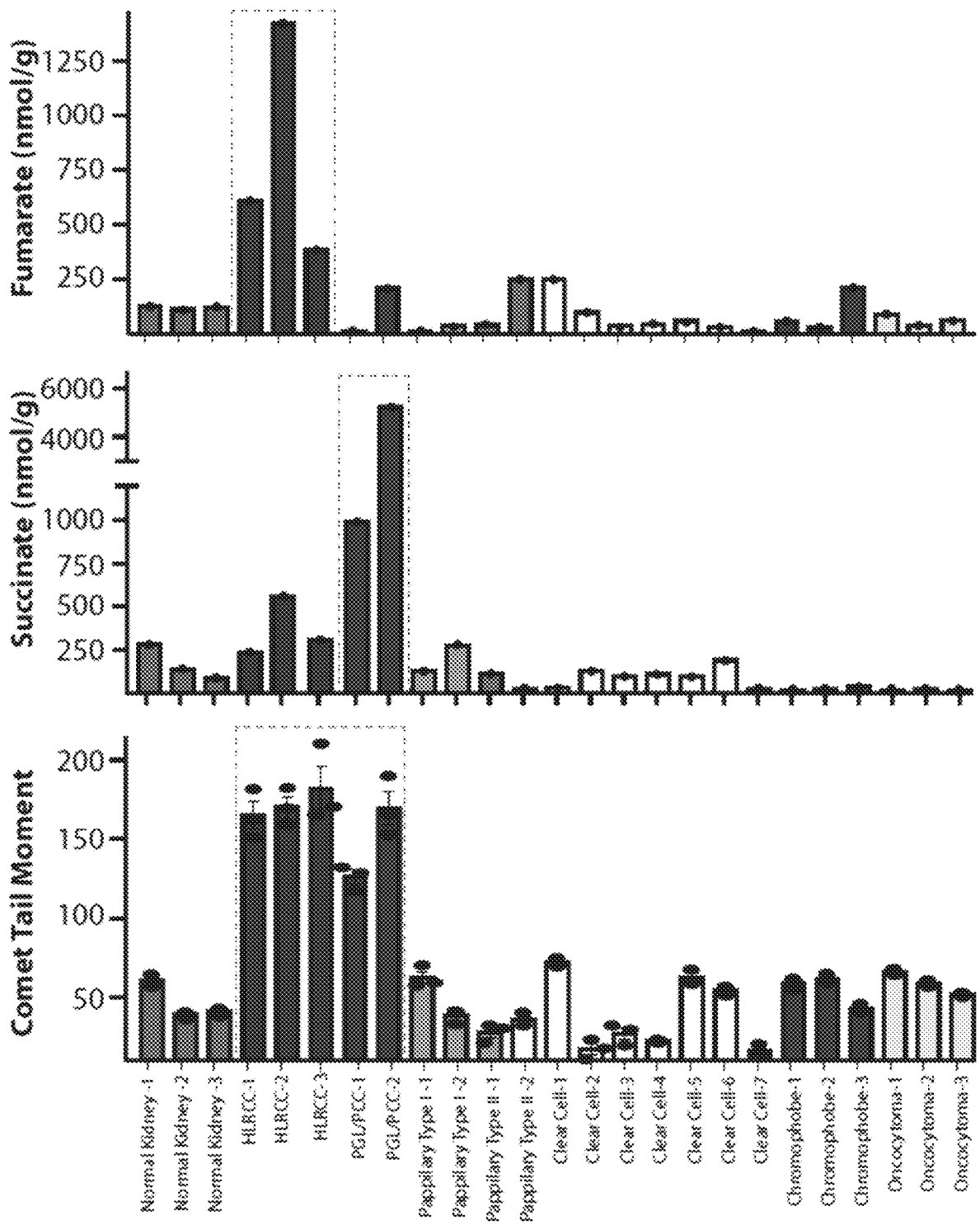

The present invention relates in part to the unexpected discovery of novel compounds that sensitize a tumor cell to anticancer therapies and that comprise succinate, fumarate, and/or derivatives or analogues thereof. The present invention also includes methods for treating or preventing cancer in a subject, wherein the cancer cells have a fumarate hydratase (FH) and/or succinate dehydrogenase (SDH) mutation.

Radiation therapy and chemotherapy are frequently used in cancer treatment, but unfortunately innate or acquired resistance to these therapies remains a major clinical challenge in oncology. The development of compounds that sensitize tumor cells to established therapies thus represents an attractive approach to optimize therapy and extend survival and quality of life in patients. As demonstrated herein, the present invention provides a novel class of DNA double-strand break repair inhibitors that exhibits potent synthetic lethal activity in the setting of DNA damage response and DNA repair defects.

As demonstrated herein, treatment with the compound of the invention is synergistic with hypoxia and PARP inhibition, and this synergism is amplified further in the context of a cancer with FH and/or SDH mutation. Without wishing to be limited by any theory, the mechanism of action of this class of compounds, derivatives and variants thereof appears to be related to inhibition of homologous recombination repair.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "antitumor agent" or "chemotherapeutic agent" refers to a compound or composition that may be used to treat or prevent cancer. Non-limiting examples of these agents are DNA damaging agents, such as topoisomerase inhibitors (for example, etoposide, camptothecin, topotecan, irrinotecan, teniposide, mitoxantrone), anti-microtubule agents (for example, vincristine, vinblastine and taxanes), antimetabolite agents (for example, cytarabine, methotrexate, hydroxyurea, 5-fluorouracil, flouridine, 6-thioguanine, 6-mercaptompurine, fludaribine, pentostatin, cholorodeoxyadenosine), DNA alkylating agents (for example, cisplatin, mecholorethamine, cyclophosphamide, ifosphamide, melphalan, chlorumbucil, busulfan, thiotepa, carmustine, lomustine, carboplatin, dacarbazine, procarbazine, temozolomide) and DNA strand break inducing agents (for example, bleomycin, doxarubicin, daunorubicine, idarubicine, mitomycin C).

Antitumor agents include but are not limited to avicin, aclarubicin, acodazole, acronine, adozelesin, adriamycin, aldesleukin, alitretnoin, allopurinl sodium, altretamine, ambomycin, amitantrone acetate, aminoglutethimide, amscrine, anastrazole, annoceous acetogenins, anthramycin, asimicin, asparaginase, asperlin, azacitidine, azetepa, azotomycin, batimstat, benzodepa, bexarotene, bicalutamide, bisantrene, bisanafide, bizelesin, bleomycin, brequinar, brompirimine, bullatacin, busulfan, cabergoline, cactinomycin, calusterone, caracemide, carbetimer, carbopltin, carmustine, carubicin, carzelesin, cedefingol, chlorumbucil, celecoxib, cirolemycin, cisplatin, cladiribine, crisnatol, cyclophosphamide, cytarabine, dacarbazine, DACA, dactinomycin, daunorubicin, daunomycin, decitabine, denileukine, dexormaplatin, dezaguanine, diaziqone, docetaxel, doxarubicin, droloxifene, dromostalone, duazomycin, edatrexate, eflornithin, elsamitrucin, estramustine, etanidazole, etoposide, etropine, fadrozole, fazarabine, feneretinide, floxuridine, fludarabine, flruouracil, fluorocitabine, 5-FdUMP, fosquidone, fosteuecine, FK-317, FK-973, FR-66979, FR-900482, gemcitabine, gemtuzumab, ozogamicin, Gold Au198, goserelin, guanacone, hydroxyurea, idarubicine, ilmofosine, interferon alpha and analogs, iprolatin, irinotecan, lanreotide, letrozole, leuprolide, liarozole, lometrexol, lomustine, losoxantrone, masoprocol, maytansine, maturedepa, mecholoroethamine, megesterol, melengesterol, melphalan, menogaril, metoprine, mycophenolic acid, mitindomide, mitocarcin, mitogillin, mitomalacin, mitomycin, mitomycin C, mitosper, mitotane, mitoxantrone, nocodazole, nogalamycin, oprelvekin, ormaplatin, profiromycin, oxisuran, paclitaxel, pamidronate, pegaspargase, peliomycin, pentamustin, peplomycin, perfosfamide, pipobroman, piposulfan, piroxantrone, plicamycin, plomestane, porfimer, prednimustin, procarbazine, puromycin, pyrazofurin, riboprine, rogletimide, rituximab, rolliniastatin, safingol, samarium, semustine, simtrazene, sparfosate, sparcomycin, sulphofenur, spirogermanium, spiromustin, spiroplatin, squamocin, squamotacin, streptozocin, streptonigrin, $SrCl_2$, talosmycin, taxane, taxoid, tecoglan, temoprofin, tegafur, teloxantrone, teniposide, terxirone, testolactone, thiamiprine, thiotepa, thymitaq, tomudex, tiazofurin, tirapamazine, Top-53, topetecan, toremixifine, trastuzumab, trestolone, tricribine, trimetrexate, tricribine, trimetrexate glucuronate, triptorelin, tubulozole, uracil mustard, valrubicine, uredepa, vapreotide, vinblastin, vincristine, vindesin, vinepidine, zinostatin, vinglycinate, vinleurosine, vinorelbine, vinrosidine, vinzolidine, vorozole, zeniplatin, zorubicine, 2-chlorodeoxyrubicine, 2'-deoxyformycin, CEP-751, raltitrexed, N-propargyl-5,8-didezafolic acid, 2-chloro-2'-arabinofluoro-2'-deoxyadenosine, 2-chloro-2'-deoxyadenosine, 9-aminocamptothecin anisomycin, trichostatin, hPRL-G129R, linomide, sulfur mustard, N-methyl-N-nitrosourea, fotemustine, streptozotocin, bisplatinum, temozolomide, mitozolomide, AZQ, ormaplatin, CI-973, DWA2114R, JM216, JM335, tomudex, azacitidine, cytrabincine, gemcitabine, 6-mercaptopurine, teniposide, hypoxanthine, doxorubicine, CPT-11, daunorubicine, darubicin, epirubicine, nitrogen mustard, losoxantrone, dicarbazine, amscrine, pyrazoloacridine, all trans retinol, 14-hydroxy-retro-retinol, all-trans retinoic acid, N-(4-hydroxyphenyl) rertinamide, 13-cisretinoic acid, 3-methyl TTNEB, 9-cisretenoic acid, fludarabine, and 2-Cda.

Additional antitumor agents include adecylpenol, 20-epi-1,25-dihydroxyvitamin-D3, 5-ethynyl uracil, abiraterone, aclarubicine, acylfulvene, adozelecin, aldesleukin, ALL-TK antagonists, altretamine, ambumastine, amidox, amifostine, amino levulinic acid, anagralide, anastrozole, andrographolide, antagonist D, antarelix, anti-dorsalizing morphogenetic protein-1, antiandrogen, antiestrogen, antineoplastone, antisense oligonucleotides, aphidicolin, apoptosis gene modulators, apotosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine, perillyl alcohol, phenozenomycin, phenyl acetate, phosphatase inhibitors, picibanil, pilocarbine and salts or analogs thereof, pirarubucin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, mTOR inhibitors, prostaglandins J2, protease inhibitors, protein A based immune modulators, PKB inhibitors PKC inhibitors, microalgal, protein tyrosine phosphatase inhibitors, purine nucleoside phosphorylase inhibitors, purpurins, pyrazoloacridines, pyridoxylated haemoglobin polyoxyethylene conjugate, raf antagonists, raltitrexed, ramosetron, ras farnesyl protein tranaferase inhibitors, ras inhibitors, ras-GAP inhibitors, ratellitptine demethylated, Rhenium Re186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binfing protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Additional antitumor agents include antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: fibrinogen I125, fludeoxyglucose F18, flurodopa F18, insulin I125, iobenguane I123, iodipamide sodium I131, iodoantipyrine I131, iodocholesterol iodopyracet I125, iofetamine HCL I123, iomethin I131, iomethin I131, iothalamate sodium I125, iothalamate I131, iotyrosine I131, liothyronine I125, merosproprol Hg197, methyl ioodobenzo guanine (MIBG-I131 or MIBGI123) selenomethionine Se75, technetium Tc99m furifosmin, technetium Tc99m gluceptate, Tc99m biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc 99m teboroxime, Tc 99m tetrofosmin, Tc99m tiatide, thyroxine I125, thyroxine I131, tolpovidone I131, triolein I125, treoline 1125, and treoline 131.

Another category of antitumor agents is anticancer supplementary potentiating agents, e.g., antidepressant drugs (imipramine, desipramine, amitryptyline, clomipramine, trimipramine, doxepin, nortryptyline, protryptyline, amoxapine, and maprotiline), or non-trycyclic anti-depressant drugs (sertaline, trazodone and citalopram), $Ca^{2+}$ antagonists (verapamil, nifedipine, nitrendipine and caroverine), calmodulin inhibitors (prenylamine, trifluroperazine and clomipramine), amphotericin B, triparanol analogs (e.g., tomoxifene), antiarrythmic drugs (e.g., quinidine), antihypertensive drugs (e.g., resepine), thiol depleters (e.g., buthionine and sulofoximine) and multiple drug resistance reducing agents such as cremaphor EL.

In certain embodiments, antitumor agents include annoceous acetogenins, ascimicin, rolliniastatin, guanocone, squamocin, bullatacin, squamotacin, axanes, baccatin, and taxanes (Paclitaxel and docetaxel).

In certain embodiments, antitumor agents include immune checkpoint inhibitors, such as but not limited to: monoclonal antibodies that target PD-1 and/or PD-L1, such as, but not limited to, pembrolizumab (KEYTRUDA®), lambrolizumab (MK-3475), nivolumab (BMS-936558/MDX-1106/ONO-4538, OPDIVO®), pidilizumab, CT-011, AMP-224, AMP-514, BMS-936559/MDX-1105, MPDL3280A, MSB0010718C and MEDI-4736; monoclonal antibodies that target CTLA-4, such as but not limited to ipilimumab (YERVOY®).

In certain embodiments, antitumor agents include anti-CD20 mAB, rituximab, rituxan, tositumoman, Bexxar, anti-HER2, trastuzumab, Herceptin, MDX20, antiCA125 mAB, antiHE4 mAB, oregovomab mAB, B43.13 mAB, Ovarex, Breva-REX, AR54, GivaRex, ProstaRex mAB, MDX447, gemtuzumab ozoggamycin, Mylotarg, CMA-676, anti-CD33 mAB, anti-tissue factor protein, Sunol, IOR-C5, C5, anti-EGFR mAB, Erbitux, anti-IFR1R mAB, MDX-447, anti-17-1A mAB, edrecolomab mAB, Panorex, anti-CD20 mAB (Y-90 lebelled), ibritumomab tiuxetan (IDEC-Y2B8), zevalin, and anti-idiotypic mAB.

In certain embodiments, antitumor agents include a serine/threonine kinase inhibitor, a phosphatidyl inositol 3-kinase-like (PIKK) protein kinase inhibitor, a DNA dependent protein kinase (DNA-PK) inhibitor (e.g. NU7441, NU7026, KU-0060648, PI-103, PIK75, PP121 and DMNB), an Ataxia Telangiectasia Mutated (ATM) inhibitor (e.g. KU-55933, KU-60019 and CP-466722), an Ataxia Telangiectasia and Rad3 Related (ATR) inhibitos (BEZ235, VE-821 and AZD6738) or an ATM/ATR inhibitor (e.g. Wartmannin, CGK 733, Torin 2 and VE-822).

In certain embodiments, antitumor agents include Poly (ADP-ribose) polymerase (PARP) inhibitors, such as but not limited to olaparib, Iniparib, Talazoparib, Niraparib, Veliparib, Rucaparib, and 3-aminobenzamide.

As used herein, the term "ATM" refers to ataxia telangiectasia mutated.

As used herein, the term "BRCA1" refers to breast cancer 1, early onset.

As used herein, the term "BRCA2" refers to breast cancer 2, early onset.

As used herein, the term "PALB2" or "FANCN" refers to partner and localizer of BRCA2.

As used herein, the term "PTEN" refers to phosphatase and tensin homolog and is a tumor suppressor.

As used herein, the term "RAD50" and "RAD51" are exemplary of DNA repair protein.

As used herein, the term "cancer" is defined as disease characterized by the rapid and uncontrolled growth of aberrant cells. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, endometrial cancer, glioma, glioblastoma multiforme, neuroblastoma, melanoma, cholangiocarcinoma and the like. The term "cancer" as used herein, should be construed to include any malignant tumor including, but not limited to, carcinoma (any cancer of epithelial origin) or sarcoma (any mesenchymal neoplasm that arises in bone and soft tissues).

As used herein the terms "cholangiocarcinoma" refers to a form of bile duct cancer composed of mutated epithelial cells. Mutations in IDH1 and IDH2 are among the most common genetic alterations in cholangiocarcinoma, particularly in intrahepatic cholangiocarcinoma (IHCC).

In one aspect, the terms "co-administered" and "co-administration" as relating to a subject refer to administering to the subject a compound of the invention or salt thereof along with a compound that may also treat the disorders or diseases contemplated within the invention. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, oral, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, pleural, peritoneal, subcutaneous, epidural, otic, intraocular, and/or topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "DNA repair protein-deficient cell" refers to a cell wherein one or more of the proteins involved in the pathway(s) for DNA repair is absent, expressed at a low level, less active (by virtue of mutation(s), truncation(s), deletion(s), partial inactivation, inhibition by small molecules and/or other proteins, and so forth) or inactive, as compared to a control cell. In certain embodiments, the one or more proteins that is/are absent, expressed at a low level, less active or inactive belongs to the DNA double-strand break (DSB) repair pathway.

As used herein, the terms "effective amount," "pharmaceutically effective amount" and "therapeutically effective amount" refer to a sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

The term "anti-tumor effective amount" as used herein refers to an amount of a compound that treats or prevents cancer.

"Glioma" as used herein is a type of brain tumor. Gliomas can be classified as grade I to grade IV on the basis of histopathological and clinical criteria established by the World Health Organization (WHO). WHO grade I gliomas are often considered benign. Gliomas of grade II or III are invasive, progress to higher-grade lesions. Grade IV tumors (glioblastomas) are the most invasive form. Exemplary brain tumors include, e.g., astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma (Balss et al., Acta Neuropathol 116:597-602 (2008); Yan et al., N Engl J Med. 360(8):765-73 (2009)).

As used herein, the term "Isocitrate dehydrogenase (IDH)" refers to a class of enzymes that catalyze the oxidative decarboxylation of isocitrate to 2-oxoglutarate (i.e., α-ketoglutarate, α-KG). These enzymes belong to two distinct subclasses, one of which utilizes NAD(+) as the electron acceptor and the other NADP(+). Five isocitrate dehydrogenases are known in the art: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes and plays a role in NADPH production. The nucleotide and amino acid sequences of IDH1 are well known in the art and has been reported in several species. In some embodiments, the human nucleotide and amino acid sequences of IDH1 are GenBank entries NM-005896.2 and NP-005887.2 respectively. The human IDH1 gene encodes a protein of 414 amino acids (Nekrutenko et al., Mol. Biol. Evol. 15:1674-1684 (1998); Geisbrecht et al., J. Biol. Chem. 274:30527-30533 (1999); Sjoeblom et al., Science 314:268-274 (2006)).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. In some embodiments, the human nucleotide and amino acid sequences of IDH2 can be found as GenBank entries NM-002168.2 and NP-002159.2 respectively. The human IDH2 gene encodes a protein of 452 amino acids (Huh et al., EMBL/GenBank/DDBJ databases; and The MGC Project Team, Genome Res. 14:2121-2127 (2004)).

A non-mutant (e.g., wild type) IDH1 catalyzes the oxidative decarboxylation of isocitrate to α-KG thereby reducing NAD (NADP+) to NADP (NADPH), e.g., in the forward reaction:

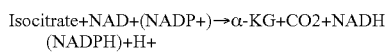

Isocitrate+NAD+(NADP+)→α-KG+CO2+NADH (NADPH)+H+

A mutant IDH has the ability to convert a-KG to 2-HG. In some embodiments, a mutant IDH1 can arise from a mutation of His, Ser, Cys or Lys, or any other at residue 132 as described previously by Yan et al. (Yan et al., N Engl J Med 360:765-773 (2009)). A mutant IDH2 can arise from a mutation of Gly, Met or Lys, or any other at residue 172 (Yan et al., N Engl J Med 360:765-773 (2009)). Exemplary mutations include the following: R132H, R132C, R132S, R132G, R132L, and R132V.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound and/or composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, "metastasis" refers to the distant spread of a malignant tumor from its sight of origin. Cancer cells may metastasize through the bloodstream, through the lymphatic system, across body cavities, or any combination thereof.

As used herein, "proliferating" and "proliferation" refer to cells undergoing mitosis.

The terms "patient" and "subject" and "individual" are used interchangeably herein, and refer to any animal, or cells thereof, whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the present invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The term "prevent," "preventing" or "prevention," as used herein, means avoiding or delaying the onset of symptoms associated with a disease or condition in a subject that has not developed such symptoms at the time the administering of an agent or compound commences.

By the term "specifically bind" or "specifically binds," as used herein, is meant that a first molecule preferentially binds to a second molecule (e.g., a particular receptor or enzyme), but does not necessarily bind only to that second molecule.

A "therapeutic" treatment is a treatment administered to a subject who exhibits signs of pathology, for the purpose of diminishing or eliminating those signs.

As used herein, the term "treat," "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Description

Hereditary Leiomyomatosis and Renal Cell Cancer (HLRCC) and Hereditary Paraganglioma and Pheochromocytoma (SDH PGL/PCC) are autosomal dominant cancer predisposition syndromes characterized by the heterozygous inheritance of loss-of-function mutations in the Fumarate Hydratase (FH) gene or succinate dehydrogenases genes (SDHA, SDHAF2, SDHB, SDHC and SDHD), respectively. Subsequent loss of heterozygosity (LOH) at these loci eliminates the remaining functional allele, resulting in excess accumulation of the respective metabolites: fumarate in the case of HLRCC, and succinate in SDH PGL/PCC. Both metabolites are thought to have a driving role in these heredity cancer syndromes via inhibition of alpha-ketoglutarate (aKG) dependent dioxygenases. Since these dioxygenases include enzymes that mediate histone demethylation or promote DNA demethylation, the associated oncogenesis has been attributed to disruption of normal epigenetic gene regulation. However, the mechanism by which these metabolites drive tumorigenesis is poorly understood. 2-hydroxyglutarate (2HG), an oncometabolite produced by the neomorphic activity of somatically mutated isocitrate dehydrogenase 1 and 2 (IDH1/2) enzymes in gliomas and other malignancies, causes homologous recombination (HR) deficiency due to the ability of 2HG to inhibit αKG-dependent enzymes. Because fumarate and succinate can also inhibit these enzymes, in certain embodiments these metabolites can act in a manner analogous to 2HG. As shown herein, high levels of fumarate and succinate in HLRCC and SDH PGL/PCC, respectively, suppress HR via inhibition of two key lysine demethylases, KDM4A and KDM4B, thereby conferring a previously unsuspected vulnerability to inhibitors of poly (ADP-ribose) polymerase (PARP).

Figure 1C:
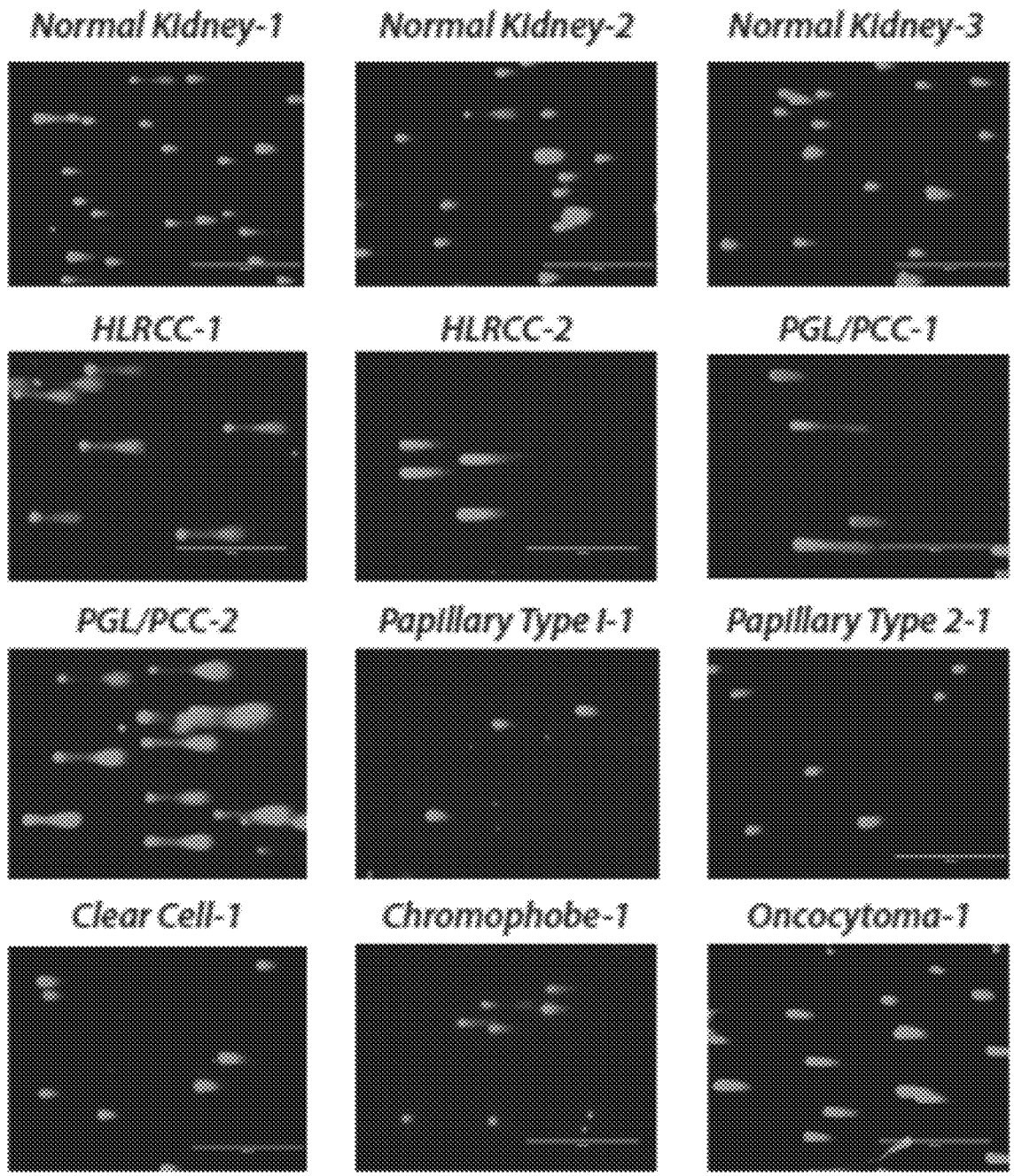

A collection of primary human HLRCC and SDH PGL/PCC tumor samples and corresponding control samples was profiled for fumarate and succinate production by liquid chromatography-mass spectrometry (LC/MS) (FIGS. 1A-1B) and for the presence of DNA double strand breaks (DSBs) by the neutral comet assay (FIGS. 1A-1C). High levels of DNA DSBs were observed in HLRCC samples (correlating with overproduction of fumarate) as well as in SDH PGL/PCC samples (producing high amounts of succinate). Quantification of the levels of the phosphorylated histone, γH2AX, another marker of DNA DSBs, by ELISA in formalin fixed, paraffin-embedded (FFPE) samples revealed high levels of γH2AX in HLRCC samples (FIG. 5A), in keeping with reduced HR repair capacity.

Figure 2A:
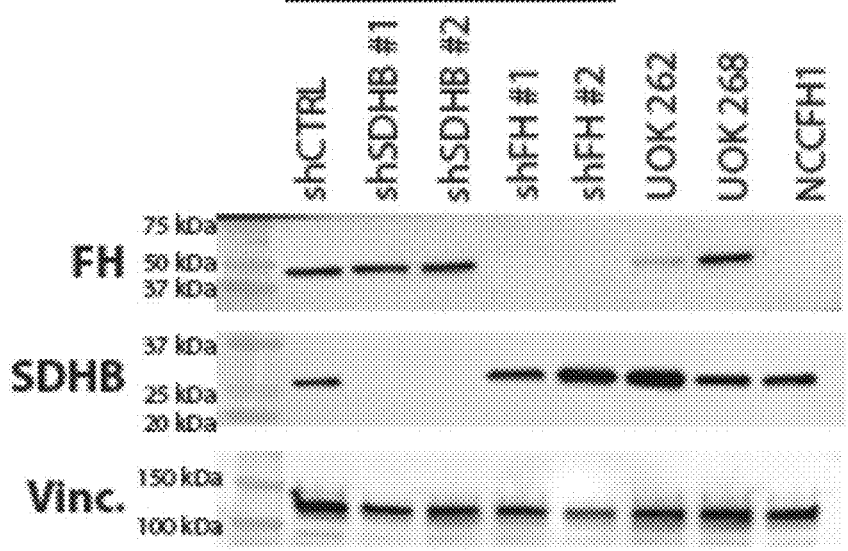
FIGS. 2A-2Q: Deficiency in succinate dehydrogenase or fumarate hydratase causes reduced homologous recombination (HR) DNA repair, elevated DNA double-strand breaks, and increased DNA damage response foci.
Figure 2B:
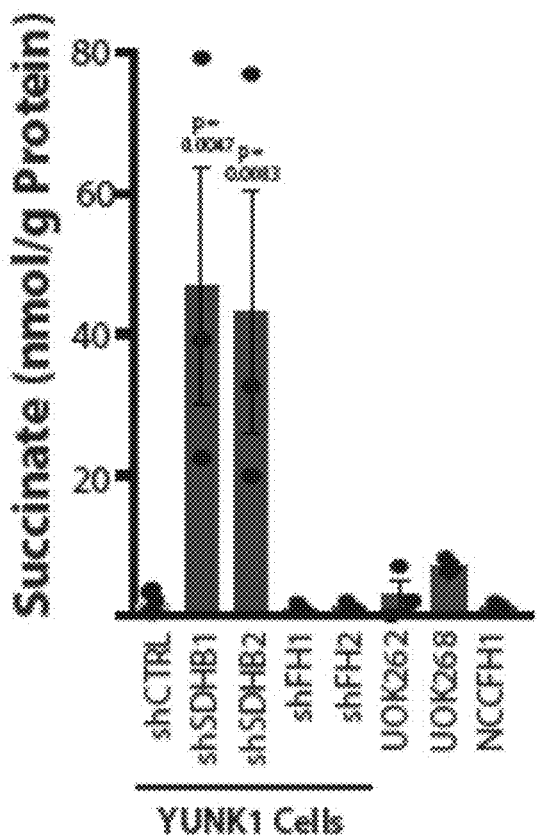
FIGS. 2B-2C: LC/MS quantification of succinate (FIG. 2B) and fumarate (FIG. 2C) after SDHB and FH knockdown in YUNK1 cells and HLRCC cell lines.
Figure 2C:
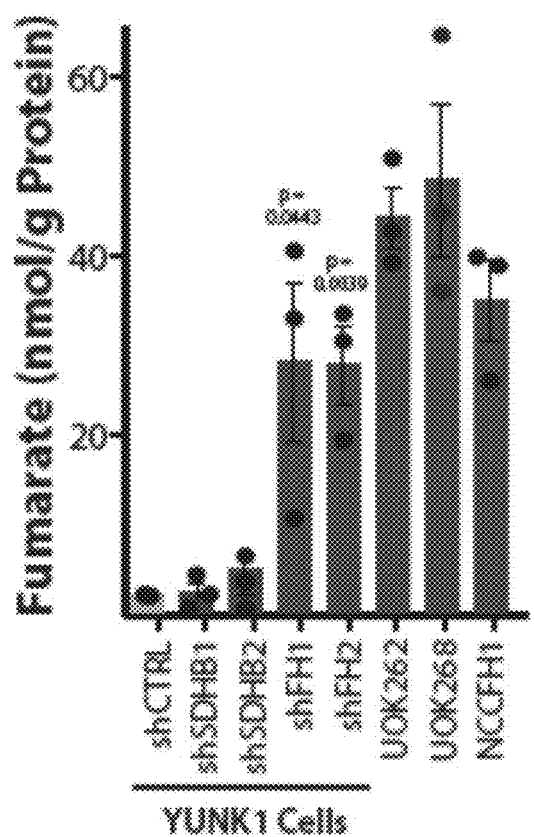
Figure 2E:
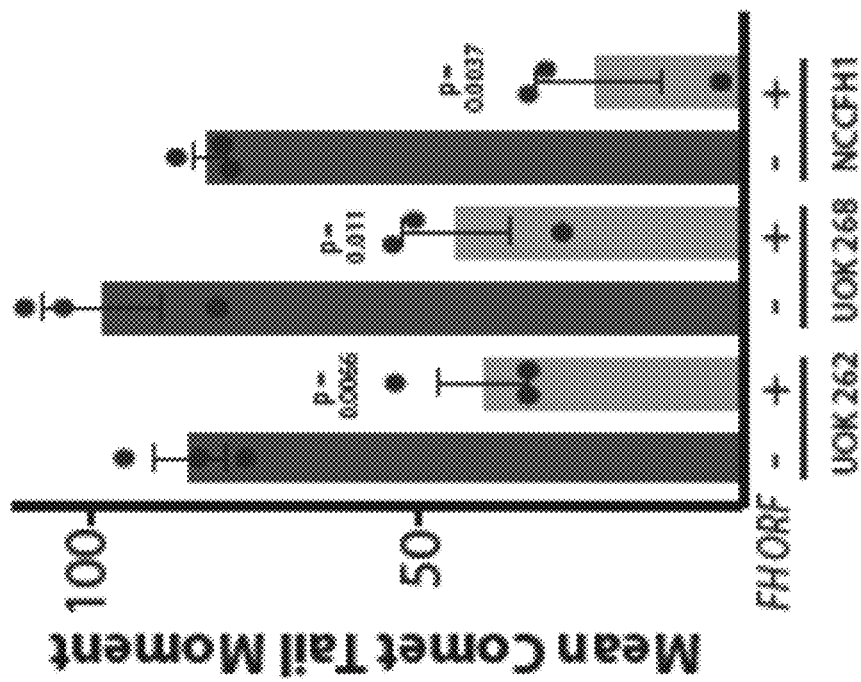
FIG. 2E: Quantification of neutral comet assay performed in HLRCC patient-derived cell lines with (+FH) or without FH plasmid complementation.
Figure 2D:
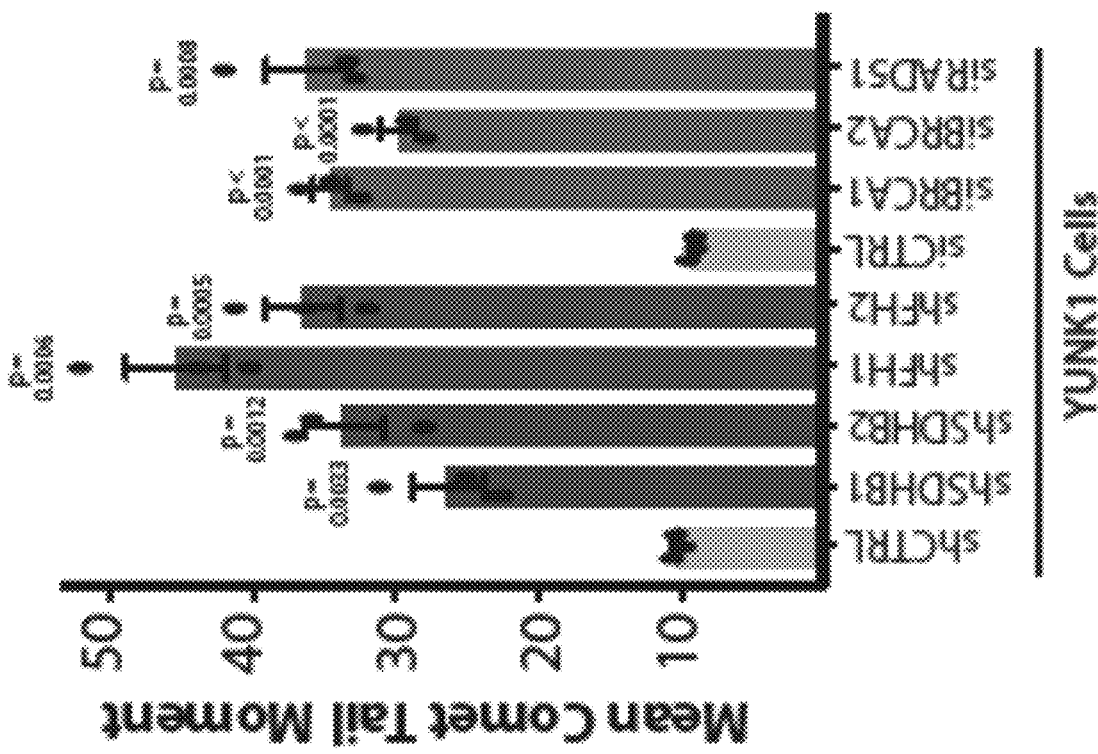
FIG. 2D: Quantification of neutral comet assay in YUNK1 cells with or without SDHB or FH knockdown compared to knockdown of the core HR factors, BRCA1, BRCA2, and RAD51.
Figure 2F:
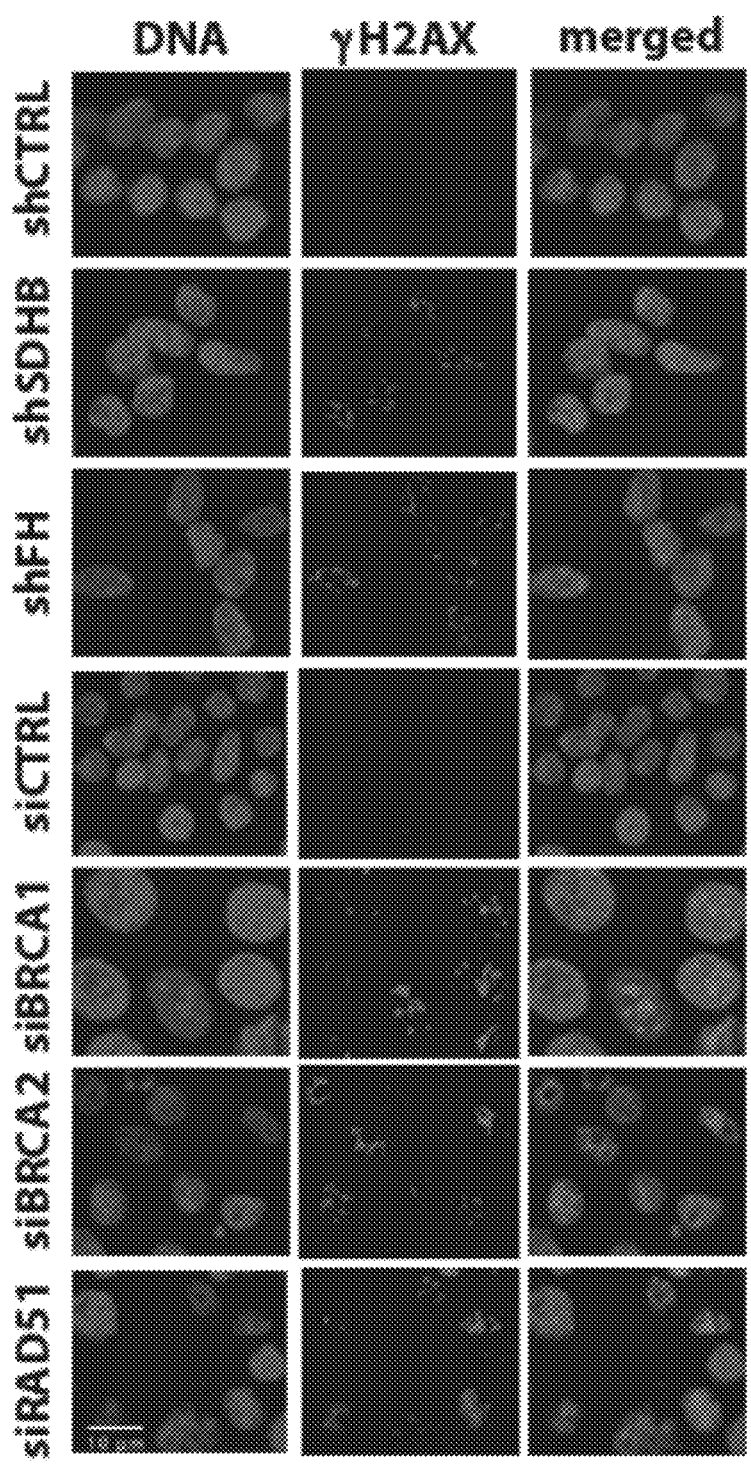
FIGS. 2F-2G: Representative images (FIG. 2F) and quantification (FIG. 2G) of γH2AX foci staining performed in HEK293FT cells with or without knockdown of the indicated factors. Quantification of γH2AX (FIG. 2H) and p53BP1 (FIG. 2I) foci in YUNK1 shRNA models of SDHB and FH knockdown, in HLRCC cell lines (UOK 262, UOK 268, and NCCFH19), and upon siRNA suppression of core HR factors in YUNK1 cells.
Figure 2G:
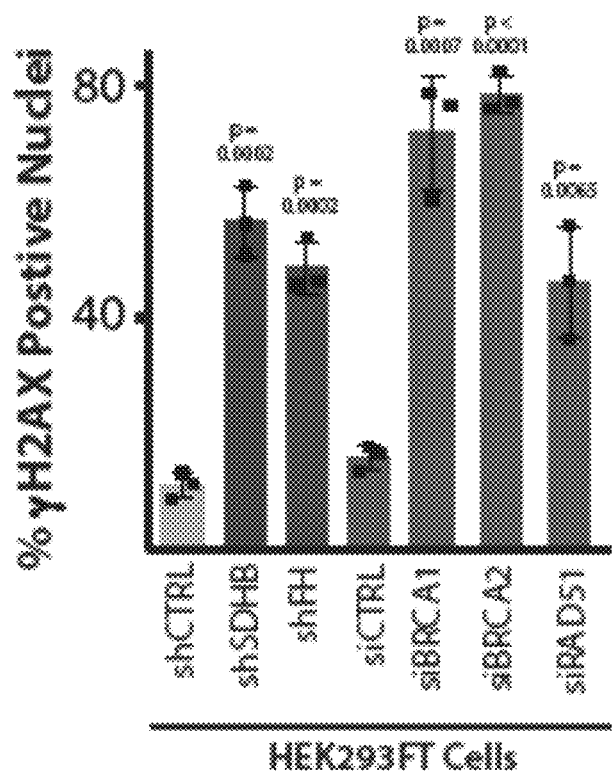
Figure 5E:
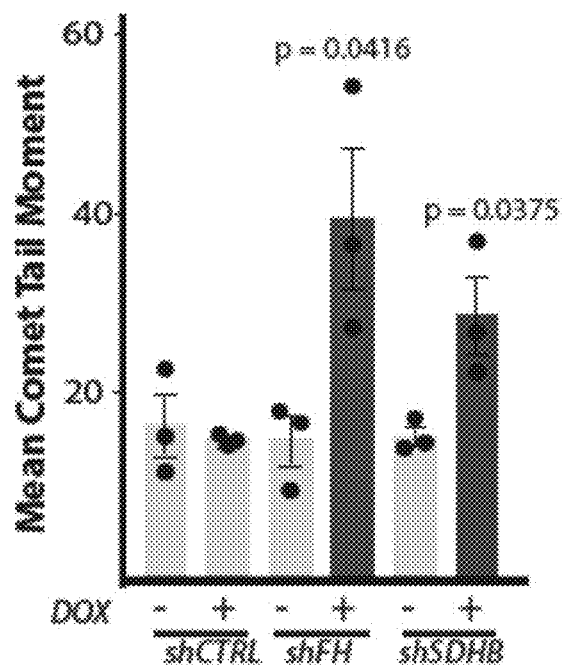
FIGS. 5A-5R: γH2AX ELISA and additional validation data for cell lines and reporter assays.
FIG. 5B: Western blot analysis of FH and SDHB in doxycycline-inducible shRNA models. Cells were collected 96 h after doxycycline induction of shRNA expression. Vinculin is used as a loading control.
FIGS. 5C-5D: LC/MS quantification of (FIG. 5C) succinate and (FIG. 5D) fumarate in YUNK1 doxycycline inducible shRNA models. n=3±SEM. Western blot analysis of (FIG. 5E) SDHB and (FIG. 5F) FH expression in pooled selected populations using two independent shFH shRNA sequences and 3 independent shFH clonal cell lines, and a single pooled population and two independent clones for shSDHB in HEK293FT shRNA models.
(FIG. 5G) Quantification and (FIG. 5H) representative images of neutral comet assays performed in YUNK1 doxycycline inducible shRNA models for shFH and shSDHB. n=3±SEM.
FIG. 5I: Quantification of neutral comet assay performed 96 h after doxycycline addition to media, for the independent sequences and clones of shFH and shSDHB in the HEK293FT cells. n=3±SEM.
FIG. 5J: Quantification of neutral comet assay performed 72 h post siRNA transfection of siBRCA1, siBRCA2 and siRAD51 in HEK293FT cells. n=3±SEM.
FIG. 5K: Quantification of neutral comet assay performed in parental DLD1 and BRCA2-/-DLD1 cells. n=3±SEM.
FIG. 5L: Western blot analysis of siRNA knockdown of BRCA1, BRCA2 and RAD51 in YUNK1 and HEK293FT cells.
FIG. 5M: Quantification by LC/MS of fumarate levels in patient-derived HLRCC cell lines UOK 262 and UOK 268 compared to HEK293FT and HEK293FT expressing shRNA targeting FH (clone 1). UOK 262, UOK268 and NCCFH1 fumarate quantification data is also presented in FIG. 2C. n=3±SEM.
FIG. 5N: Western blot analysis of FH expression in the NCCFH1, UOK 268, and UOK 262 patient-derived cell lines transiently transfected with an FH expressing vector. Vinculin is used as a loading control.
FIG. 5O: Quantification of luciferase reactivation by HR in parental DLD1 and BRCA2 −/−DLD1 cells. n=3±SEM.
FIG. 5P: Quantification of luciferase reactivation by non-homologous end-joining (NHEJ) in the doxycycline-inducible shRNA models of FH and SDHB knockdown in HEK293FT and YUNK1 cells. n=3±SEM.
FIG. 5Q: Western blot analysis of siRNA knockdowns of FH, SDHB, BRCA1, BRCA2, and RAD51 in U2OS cells.
Figure 5F:
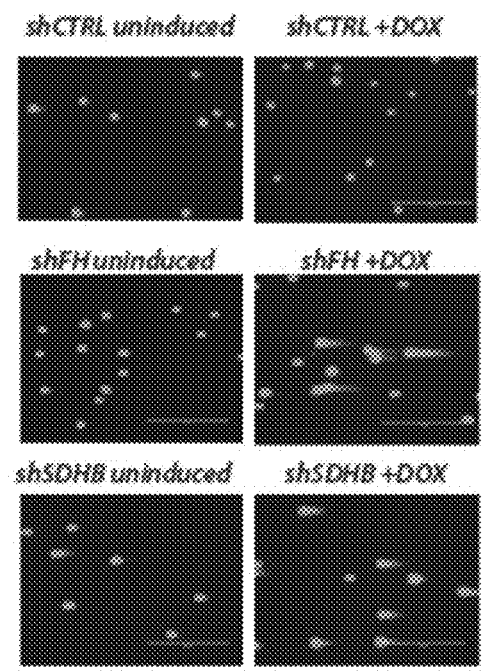

Next, the link between elevated DSBs and loss of SDHB or FH with the resultant metabolite overproduction was experimentally tested. Using both a constitutive shRNA system and a doxycycline-inducible lentiviral shRNA system in the SV40-immortalized Yale University Normal Kidney 1 (YUNK1) cell line (derived from uninvolved cortical tissue from a nephrectomy specimen) and in HEK293FT kidney cells, expression of SDHB or FH was knocked down, yielding the expected increased production of succinate and fumarate, respectively (FIGS. 2A-2C and FIGS. 5B-5D, 5G-5I). With either SDHB or FH knockdown, substantial increases in DSBs were observed as measured by the comet assay (FIG. 2D and FIGS. 5E-5F). Similar levels of elevated DSBs were observed upon knockdown of RAD51, BRCA1 and BRCA2 in YUNK1 and in HEK293FT cells, and upon BRCA2 homozygous knockout in DLD1 cells (FIG. 2D and FIGS. 5J-5L). In addition, similar elevations in DNA DSBs were found in three patient-derived HLRCC cell lines, UOK 262 (FH-/-), UOK 268 (FH p.His192Asp) and NCCFH1 (FH-/-) (FIG. 2E), all three of which are deficient in FH activity (as confirmed by elevated levels of fumarate measured by LC/MS; FIG. 5M). The elevated DSBs were suppressed in these lines upon complementation by transient expression of wild-type FH by plasmid transfection (FIG. 2E and FIG. 5N), further supporting the link between fumarate and suppression of HR.

Figure 2H:
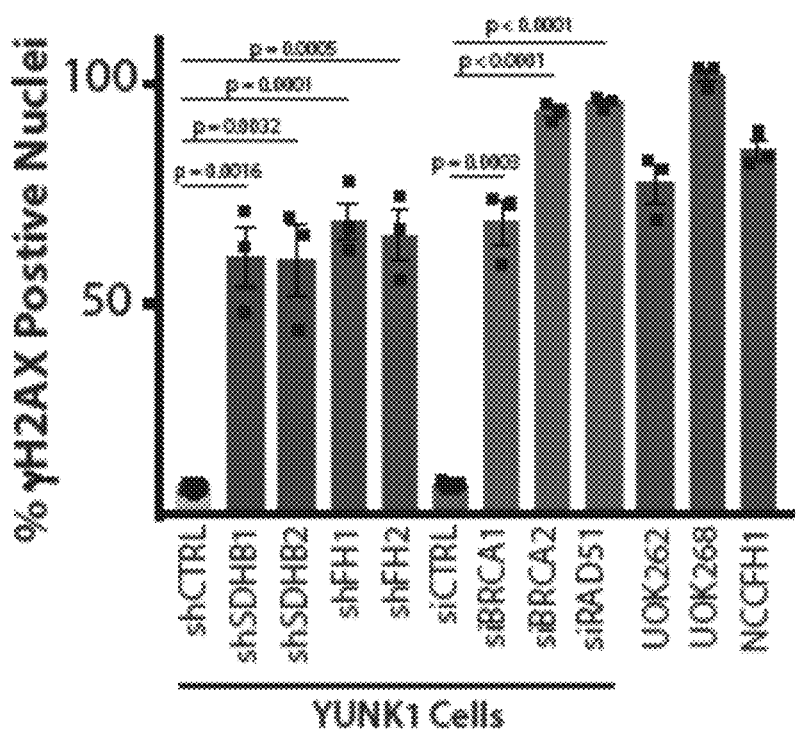
FIG. 2J: Luciferase-based plasmid reactivation assay to report HR.
FIGS. 2K-2M: Quantification of luciferase reactivation by HR in YUNK1 cells (FIG. 2K) with shRNAs suppressing SDHB and FH, in doxycycline-inducible shRNAs targeting SDHB and FH in YUNK1 and HEK293FT cells (FIG. 2L), and in patient-derived HLRCC cell lines transiently transfected or not with a plasmid expressing FH for complementation of the FH deficiency (FIG. 2M).
FIG. 2N: DR-GFP assay to report HR in U2OS cells.
FIG. 2O: Quantification of DR-GFP HR assay after transfection of U2OS cells with siRNAs targeting SDHB or FH as well as core HR factors.
FIG. 2P:
Quantification of RAD51 foci formation upon 2 Gy IR treatment of YUNK1 and HEK293FT cells with or without shRNA suppression of SDHB or FH.
Figure 2I:
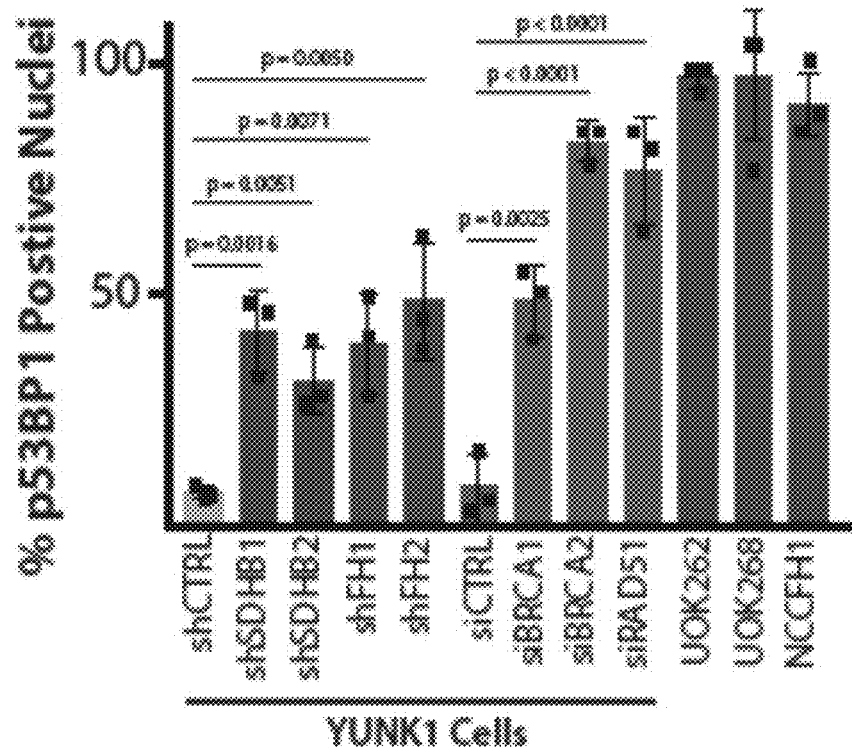

In addition to γH2AX foci, increased phosphorylated 53BP1 (p53BP1) nuclear foci are also markers of the cellular response to DNA DSBs, and HR-deficient cells show elevated levels of γH2AX and p53BP1 foci in the absence of exogenous DNA damage. shRNA knockdown of SDHB or FH resulted in high levels of γH2AX and p53BP1 foci, and that these foci levels were similar in magnitude to those seen in the context of siRNA knockdown of BRCA1, BRCA2 and RAD51, central factors in the HR pathway (FIGS. 2F-2I). High levels of these foci were also seen in UOK 262, UOK 268, and NCCFH1 cells (FIGS. 2H-2I).

Figure 2J:
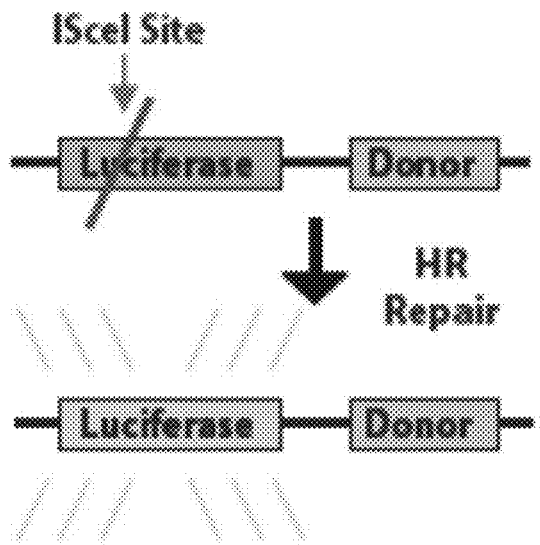
Figure 2K:
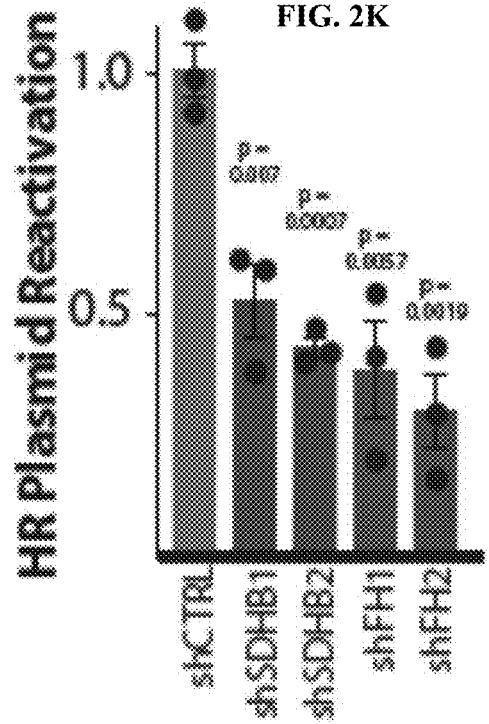
Figure 2L:
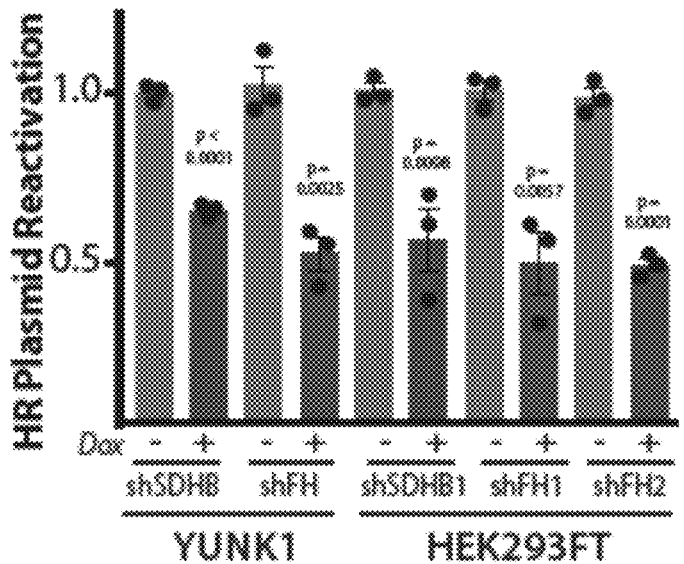

To directly test for DNA DSB repair deficiency, two different luciferase-based DNA repair assays, that can report either HR or non-homologous end-joining (NHEJ) activity (FIG. 2J), were employed. These assays can assess the relative differences in pathway specific DNA DSB repair activity across cell lines (FIG. 5O). Suppression of the HR pathway, along with a slight increase in the NHEJ pathway, were noted as a function of both SDHB or FH knockdown (FIGS. 2K-2L and FIG. 5P) and in the patient-derived HLRCC cell lines (FIG. 2M).

Figure 2M:
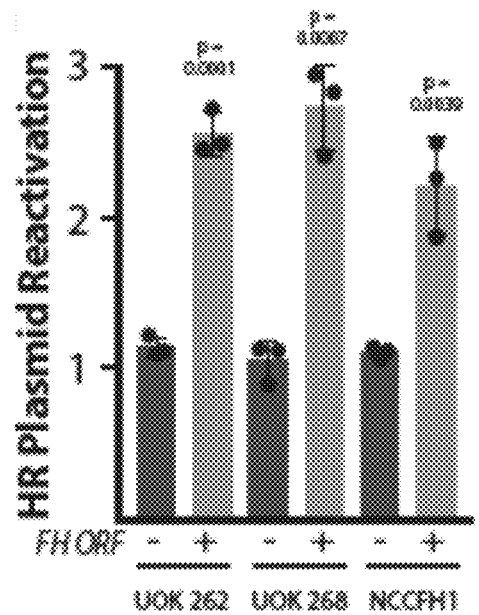
Figure 2N:
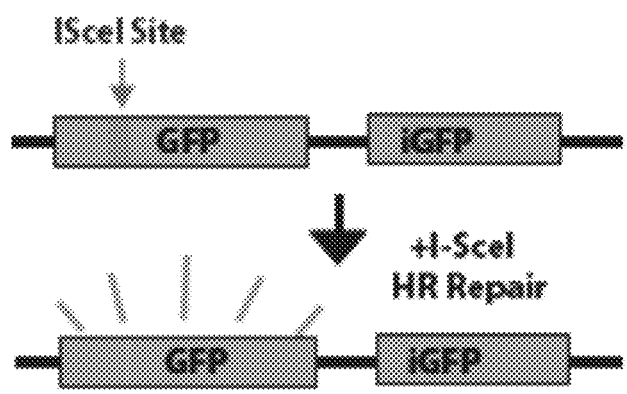
Figure 2O:
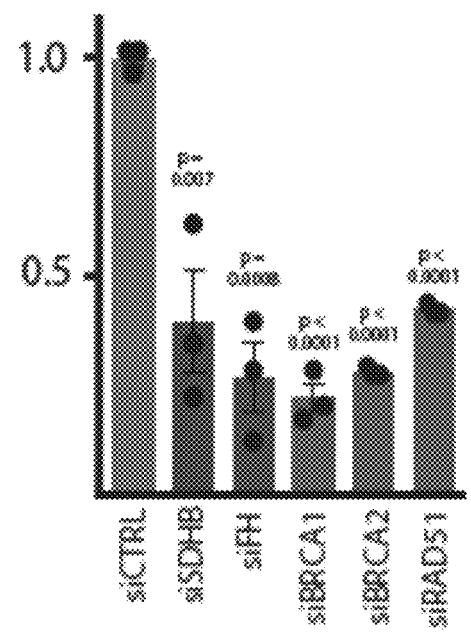
Figure 2P:
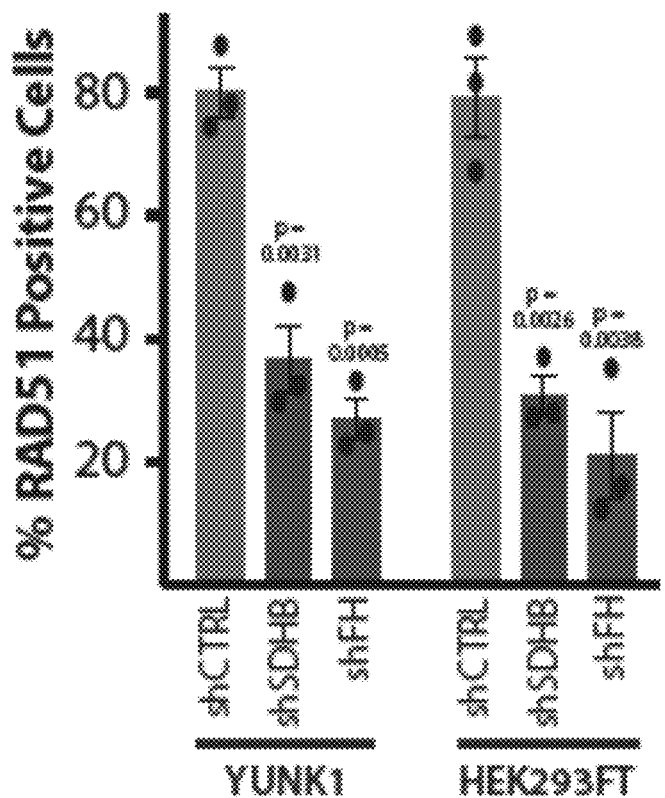
Figure 2Q:
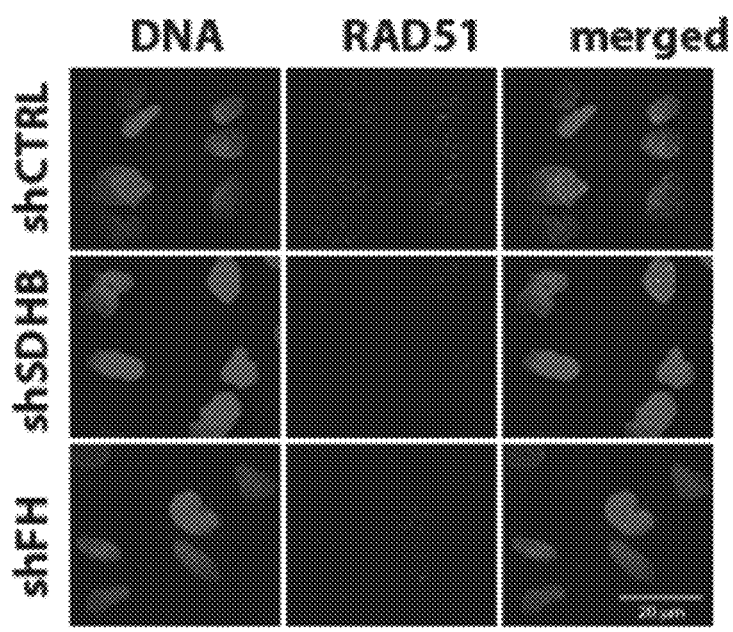
Figure 6E:
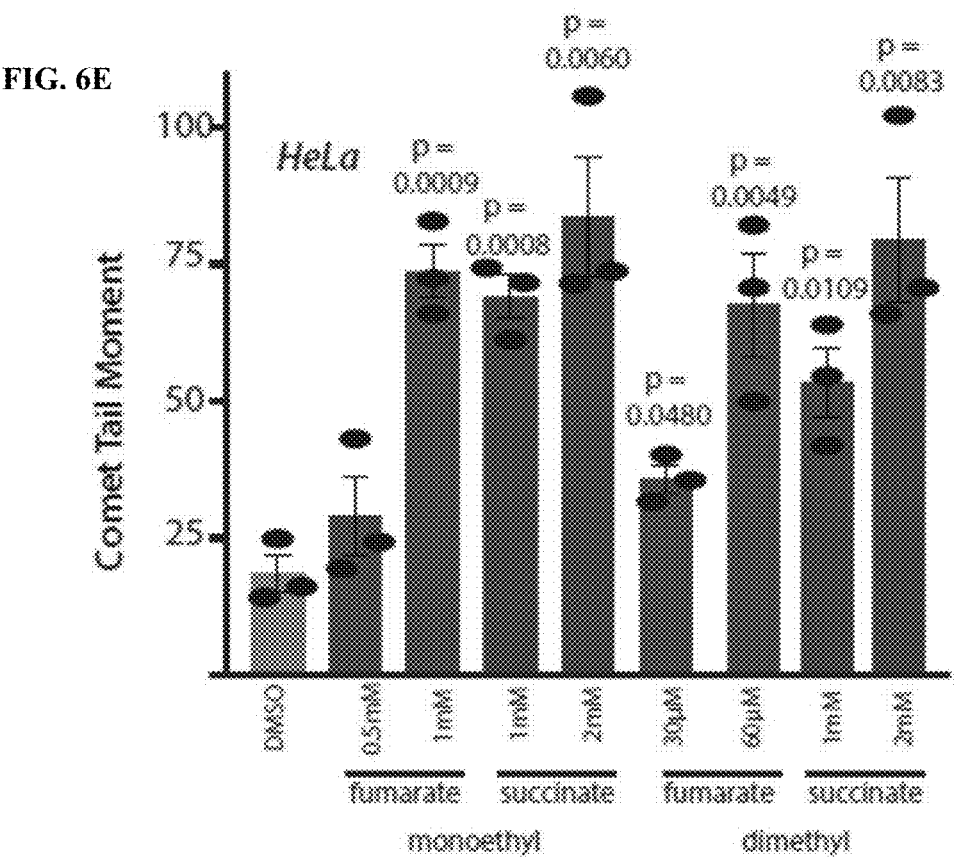
Figure 6F:
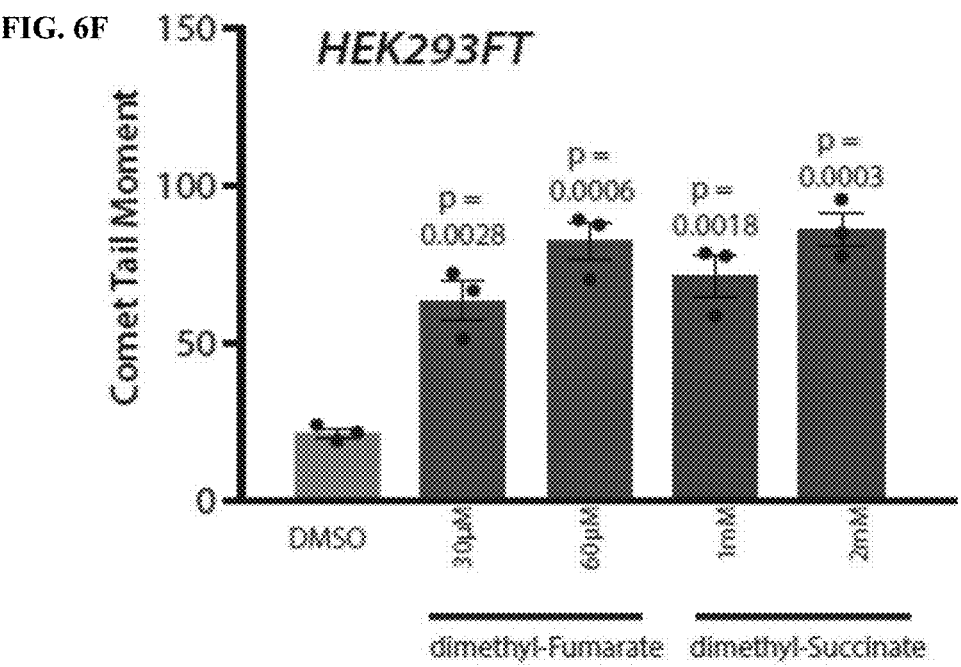
Figure 6G:
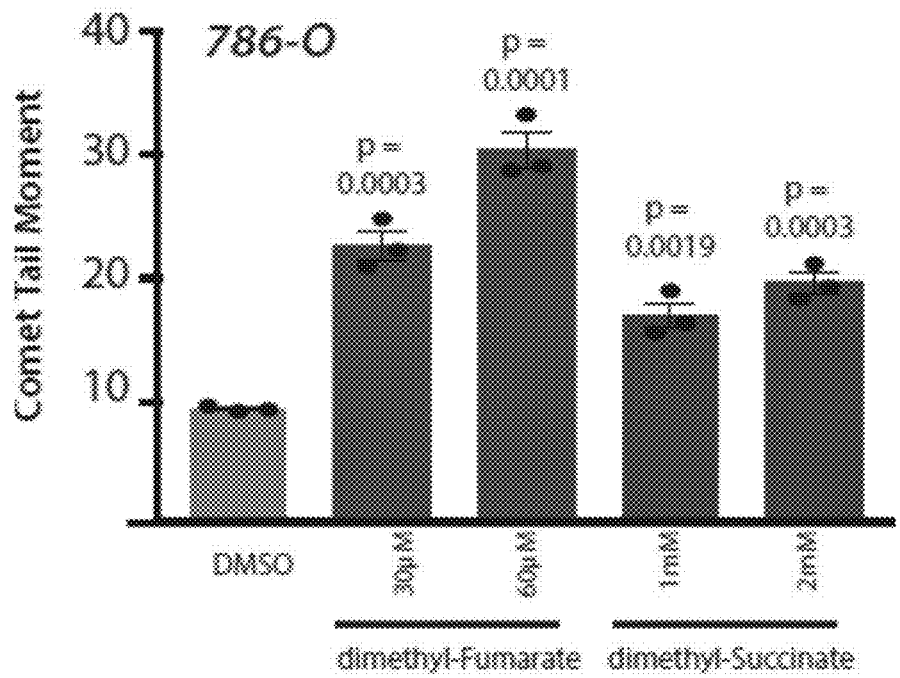
Figure 6H:
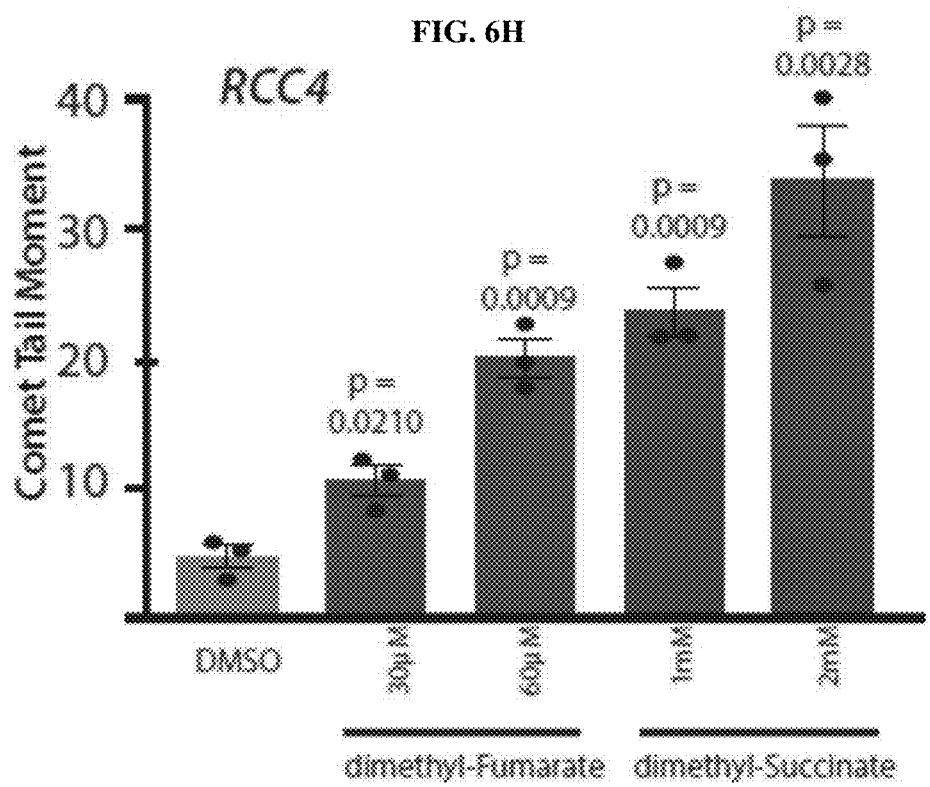
Figure 6I:
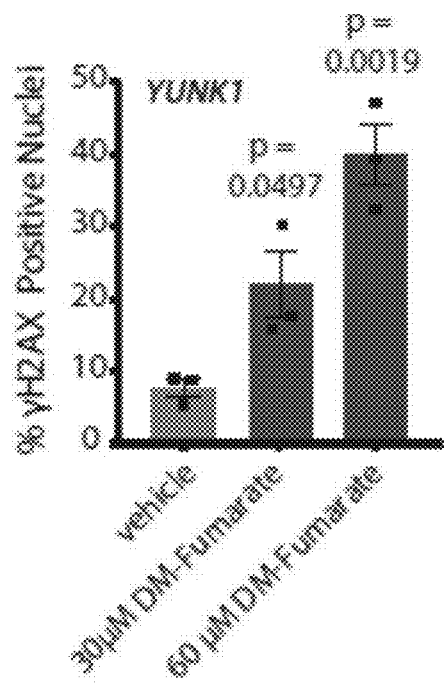
Figure 6J:
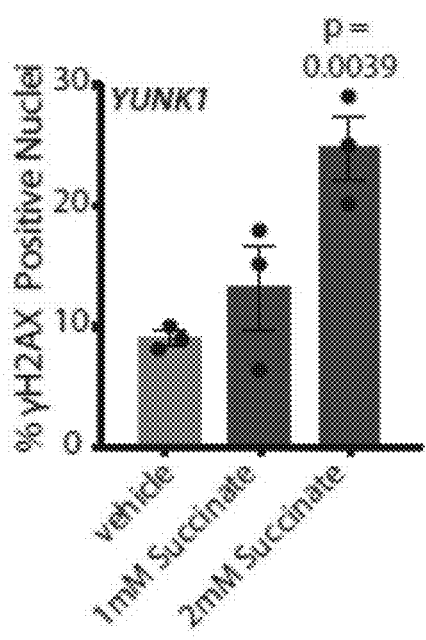
Figure 6K:
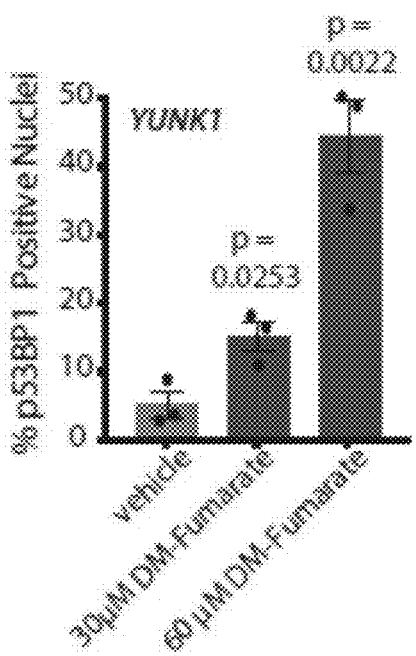
Figure 6L:
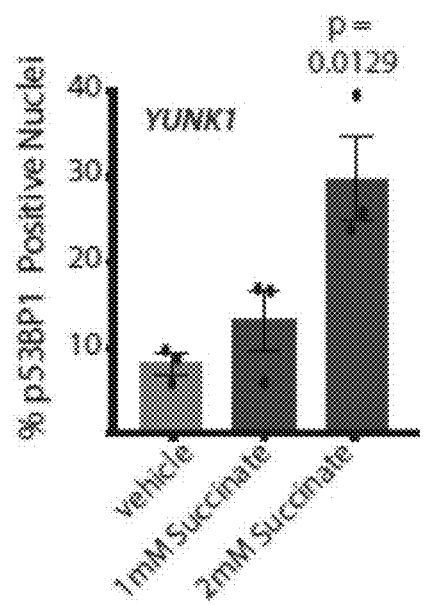

Complementation by expression of WT FH rescued HR function (FIG. 2M). Next, further evaluation of the extent of the HR suppression was sought using the well-established DR-GFP assay in U2OS cells, a chromosomal reporter assay for HR that is widely used as a benchmark assay in the DNA repair field (FIG. 2N). It was found that siRNAs targeting SDHB or FH resulted in substantial suppression of HR and that this suppression was similar in magnitude to that seen with siRNAs targeting key HR proteins including BRCA1, BRCA2, and RAD51 (FIG. 2O and FIG. 6Q). Another measure of HR capacity is the formation of RAD51 foci in response to DNA damage. It was observed that YUNK1 and HEK293FT cells with SDHB or FH knockdown have a deficiency in RAD51 foci formation after treatment with ionizing radiation (IR) consistent with reduced HR (FIGS. 2P-2Q and FIG. 6R).

Figure 3A:
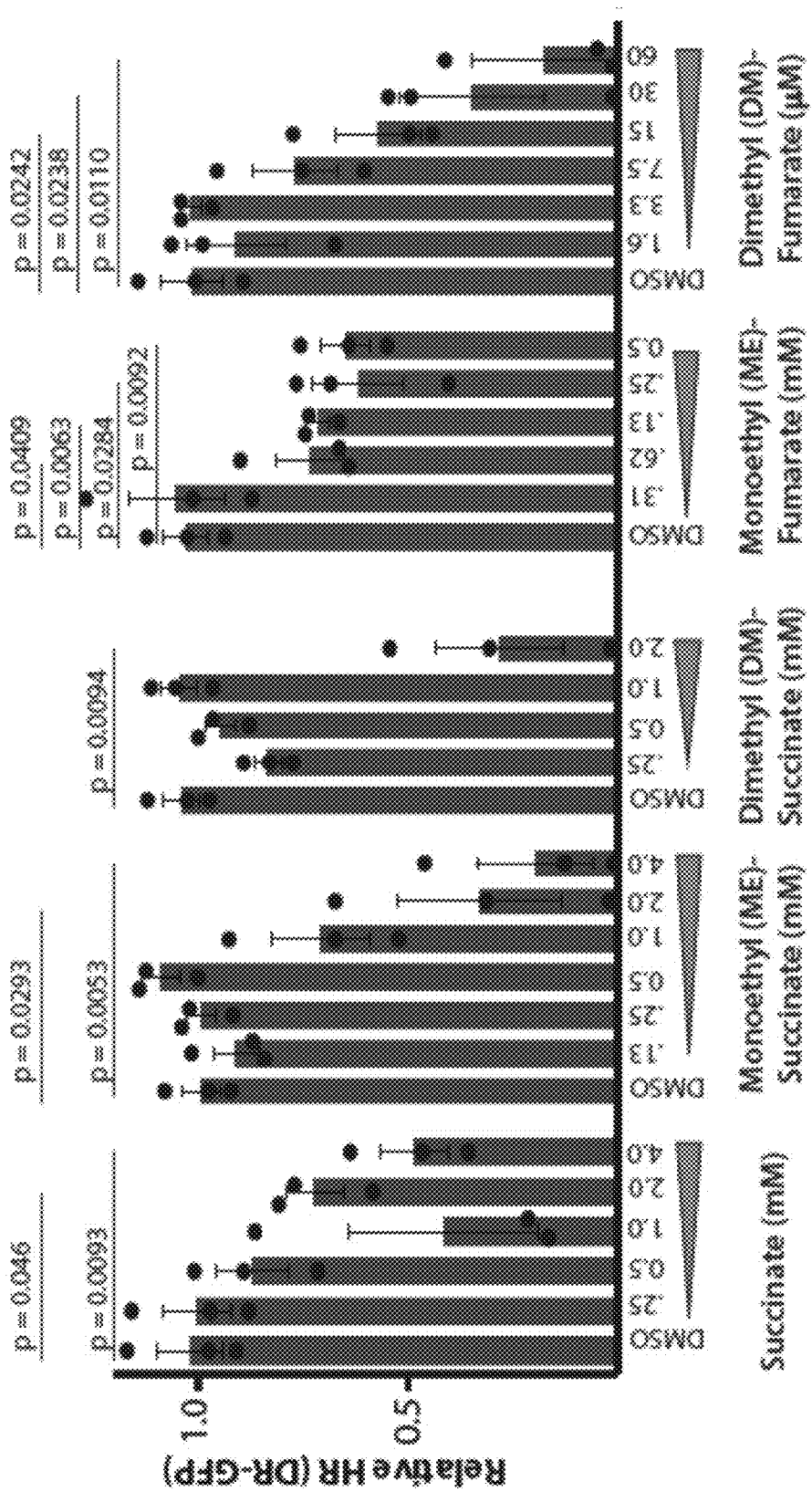
Figure 3G:
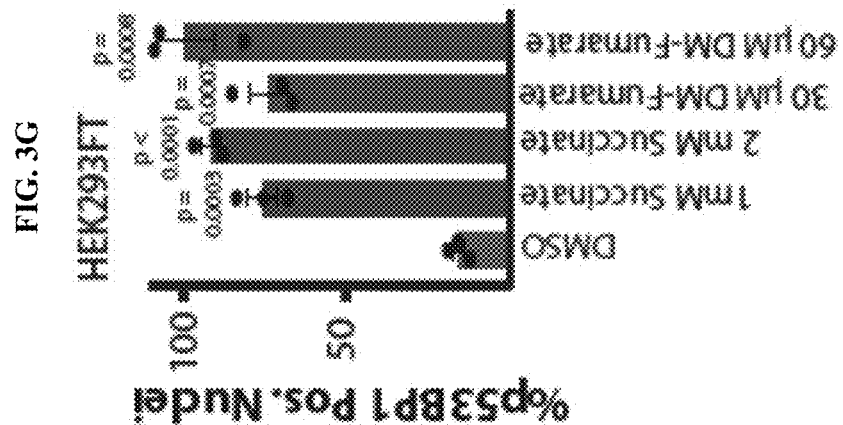
Figure 3F:
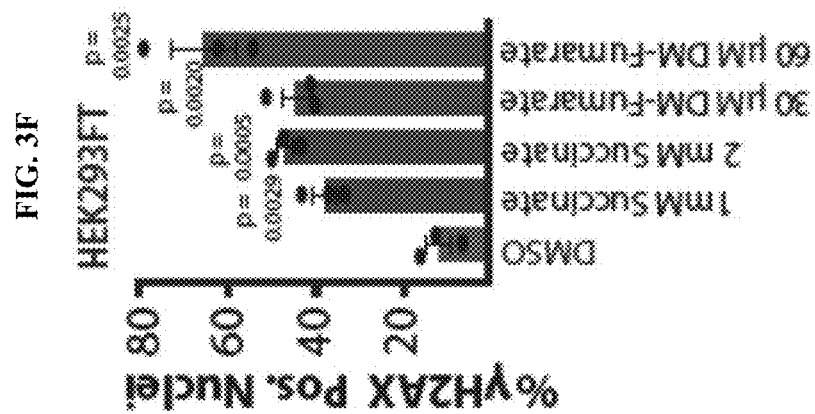
Figure 3E:
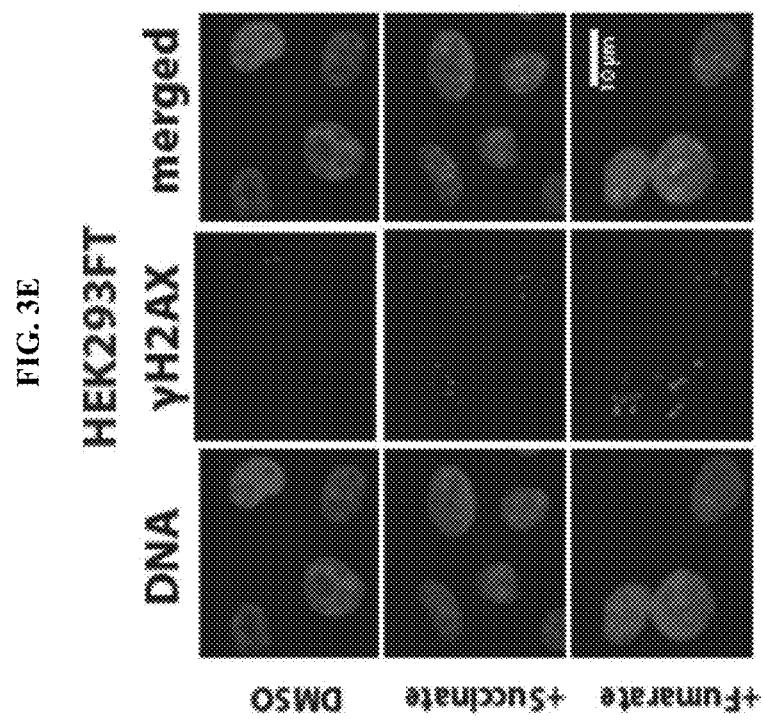
Figure 3I:
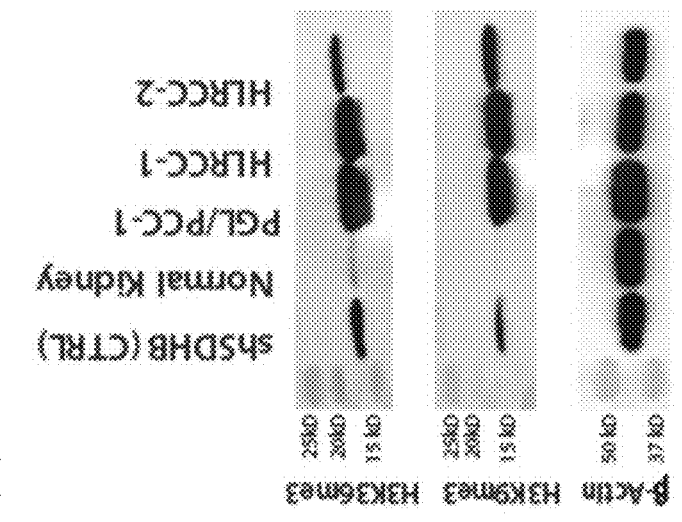
Figure 3H:
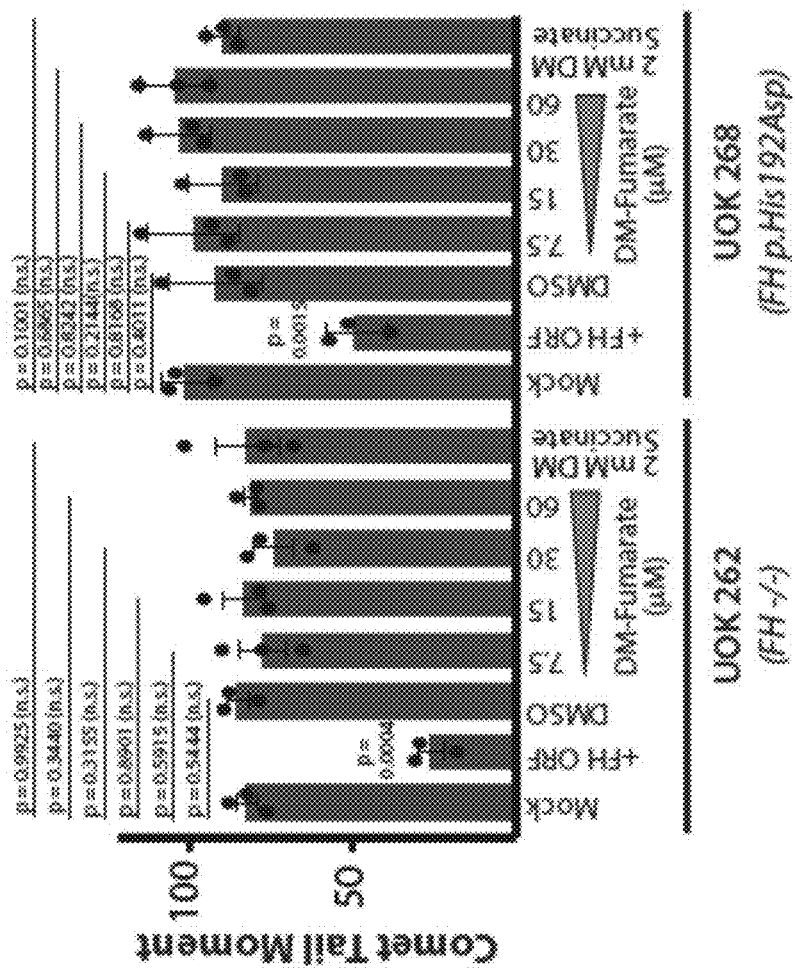

It was next tested if elevated levels of fumarate and succinate, themselves, are sufficient to drive the HR deficiency associated with SDHB or FH loss. Addition of the metabolites and/or cell permeable versions thereof (succinate, monoethyl-succinate, dimethyl-succinate, monoethyl-fumarate and dimethyl-fumarate) to the cell culture medium was sufficient to suppress HR in a dose-dependent manner as measured using the DR-GFP assay (FIG. 3A). The metabolites alone were sufficient to suppress HR in YUNK1 cells as measured by the luciferase-based HR reporter assay (FIG. 3B). Metabolite treatment of the YUNK1 cells also induced elevated DNA DSBs in the comet assay (FIGS. 3C-3D and FIGS. 6A-6C). Similar effects of the metabolites were seen in other cell lines (FIGS. 6D-6H). Increases in γH2AX and p53BP1 foci were also produced by addition of succinate or dimethyl-fumarate to the cell culture media in the HEK293FT cells (FIGS. 3E-3G) and YUNK1 cells (FIGS. 6I-6L). In a demonstration of epistasis, exogenous fumarate and succinate had no further effect on the levels of DNA DSBs in the FH-deficient HLRCC cells, UOK 262 and UOK 268, that already overproduce fumarate because of functional FH loss (FIG. 3H).

Figure 7A:
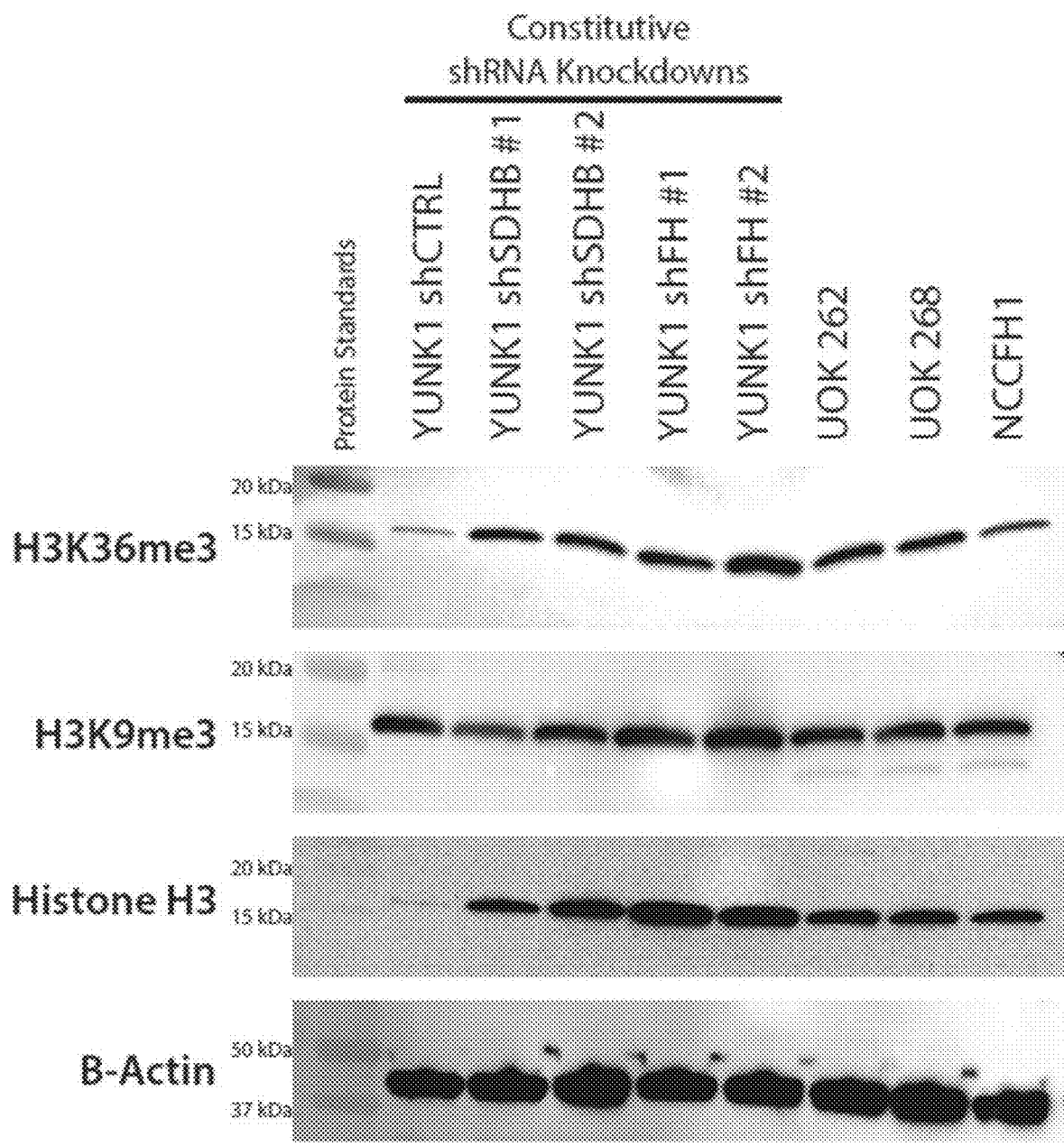
FIGS. 7A-7F: Histone hypermethylation in cells deficient in Krebs-cycle enzymes, in xenografts and in metabolite-treated cells.
Figure 7B:
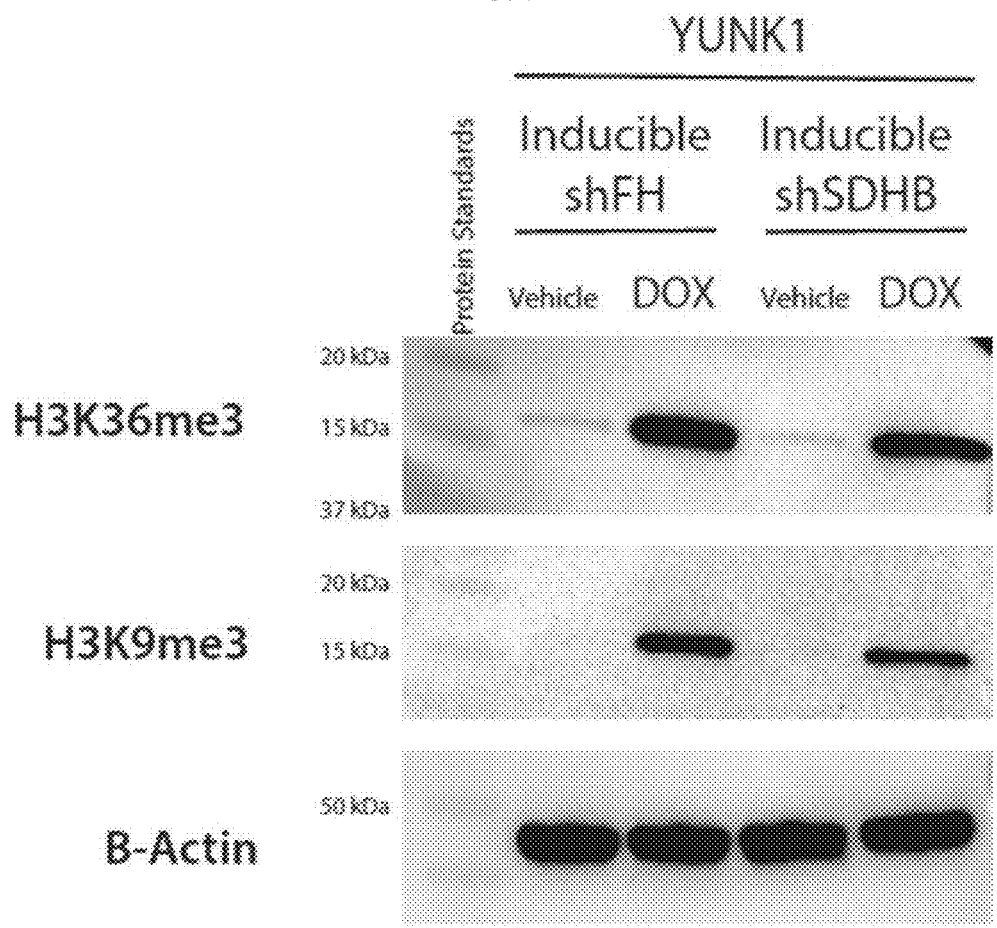
Figure 7C:
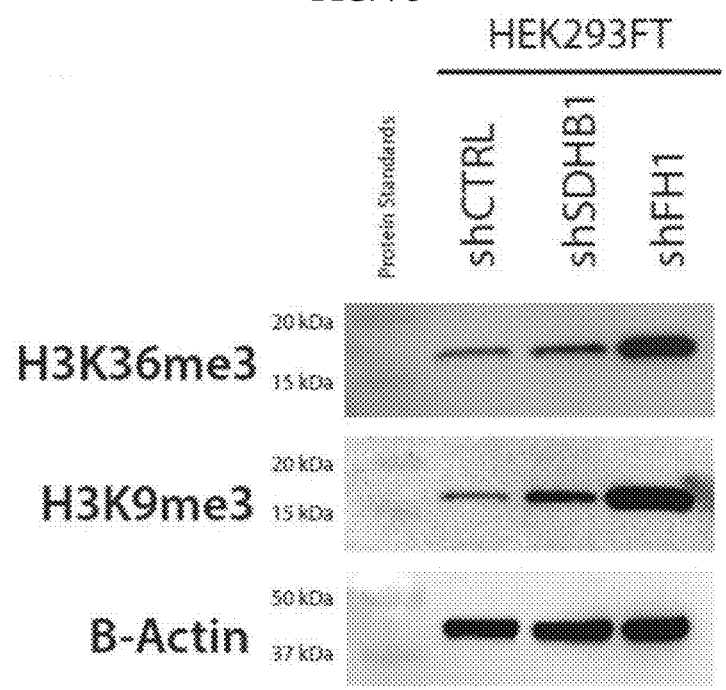
Figure 7D:
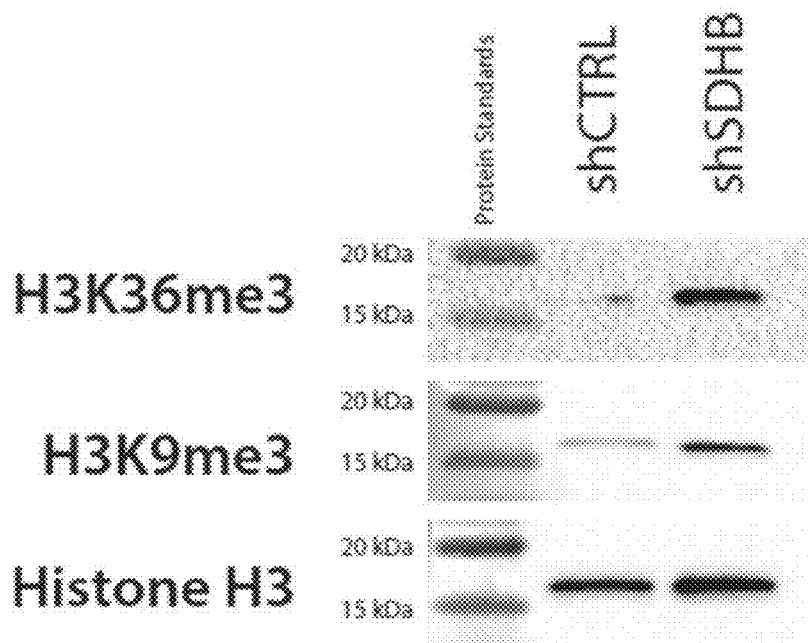
Figure 7E:
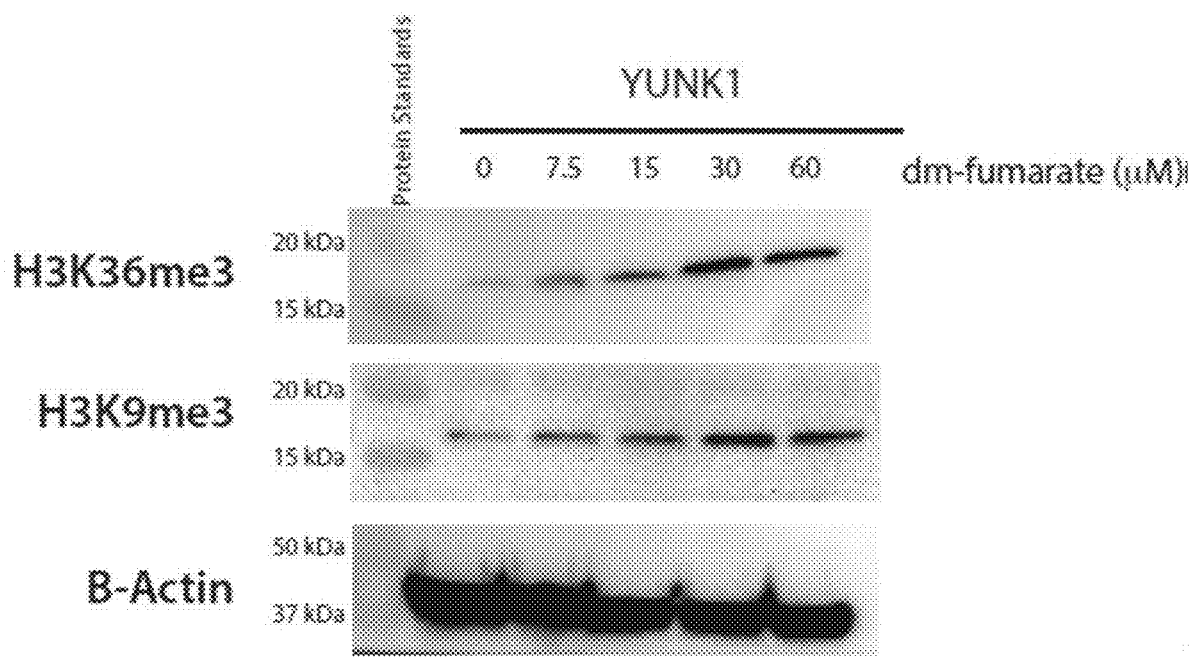
Figure 7F:
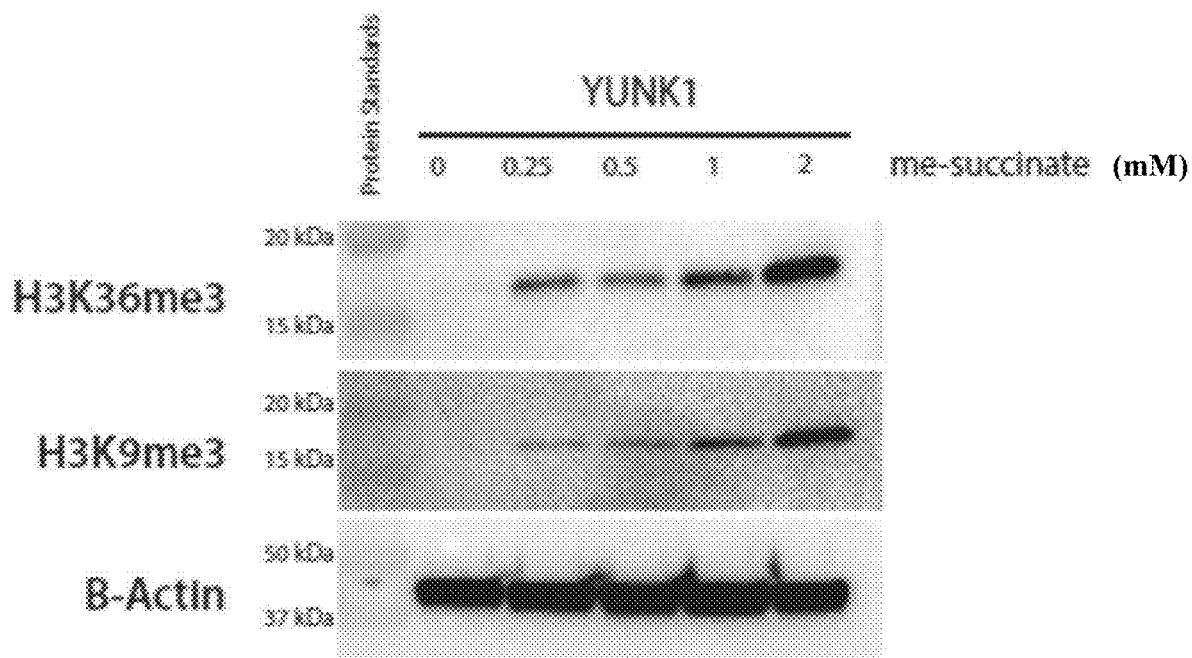

Mechanistically, fumarate and succinate have similar structure and are known to converge in function by competitively inhibiting αKG dependent dioxygenases, including the lysine demethylases, KDM4A and KDM4B, which are key regulators of DNA repair. To directly test for the predicted suppression of KDM4A and KDM4B activity, western blots were performed to measure the levels of tri-methylated histone 3 lysine 36 (H3L36me3) and tri-methylated histone 3 lysine 9 (H3K9me3), known targets for demethylation by KDM4A and B. H3K36me3 and H3K9me3 levels were elevated in human tumors with SDHB or FH deficiency (FIG. 3I), in patient-derived HLRCC cell lines (UOK 262 and UOK 268) (FIG. 7A), in YUNK1 and HEK293FT cells with SDHB or FH knockdown (FIGS. 7A-7C), and in xenograft tumors formed by HEK293FT cells with SDHB knockdown (FIG. 7D), compared to respective controls. A dose-dependent increase in H3L36me3 and H3K9me3 levels was observed upon treatment of YUNK1 cells with increasing doses of fumarate and succinate (FIGS. 7E-7F). These findings all provide functional evidence of KDM4A and B inhibition by elevated levels of succinate and fumarate.

Figure 3J:
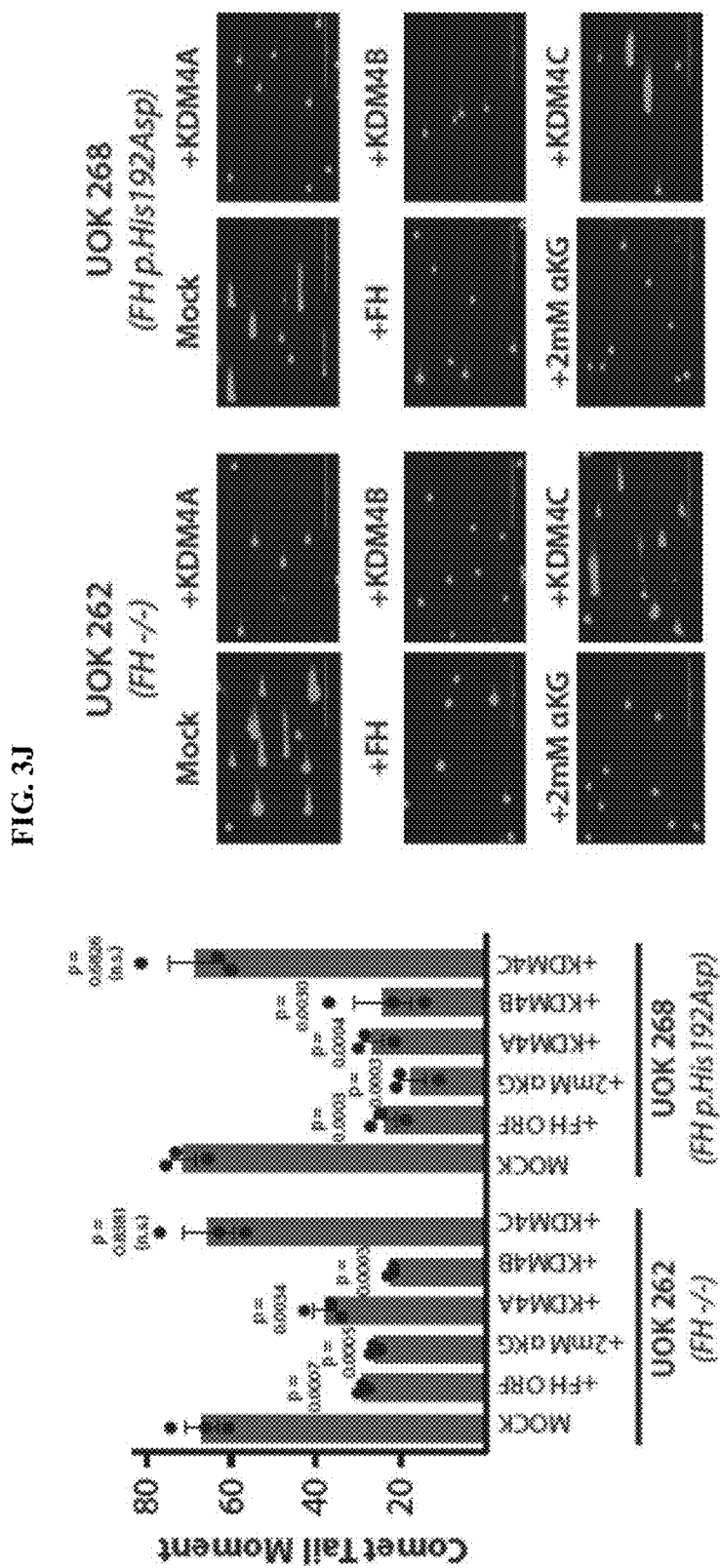
Figure 3K:
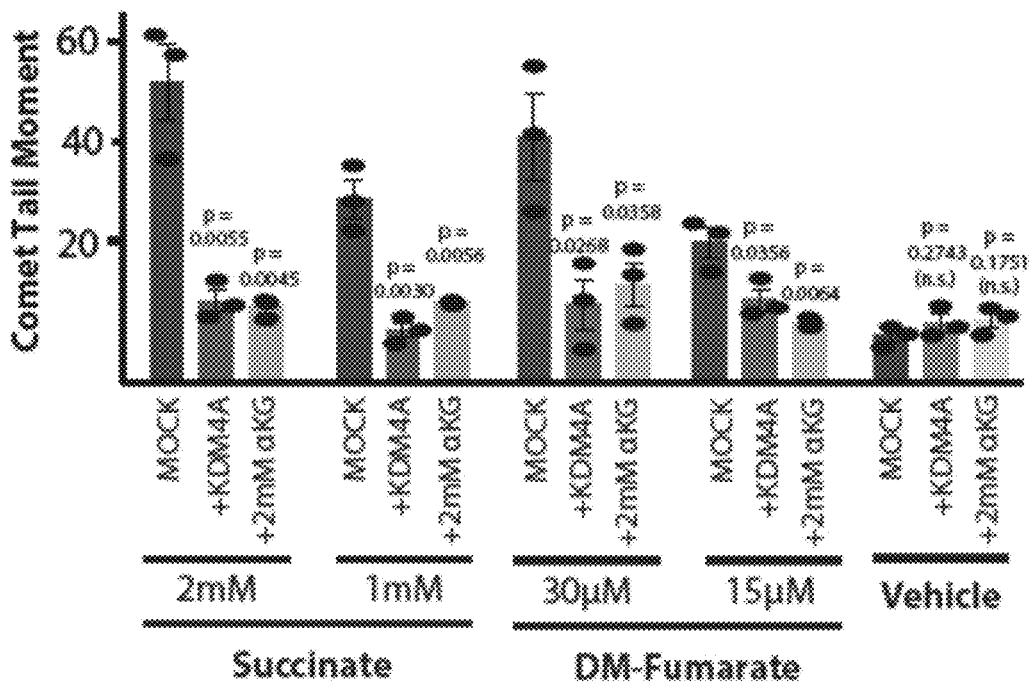
Figure 3L:
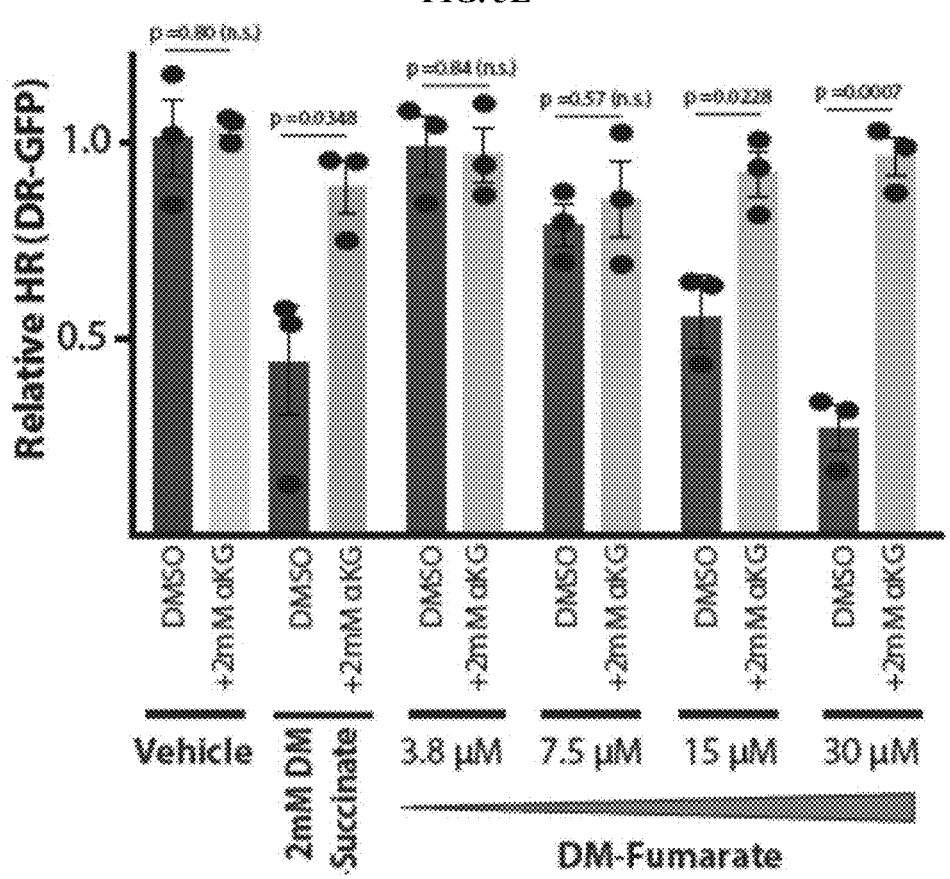

Next, the hypothesis that the HR suppression conferred by fumarate and succinate is mediated through this inhibition of KDM4A/B was tested. By forced expression of KDM4A or KDM4B, the elevated DSB phenotype (as measured by comet assay) of the two patient-derived HLRCC cell lines, UOK 262 and UOK 268, as well as the comet phenotype in YUNK1 induced by exogenous fumarate and succinate (FIG. 3J) were rescued. There was no effect seen when KDM4C was over-expressed, even though KDM4C is a member of the same JMJD2 family as KDM4A and B and shares substantial homology with them, showing the specificity for the KDM4A/B proteins (FIG. 3J). Further, the addition of αKG to the cells (to compete out the fumarate) also rescued the phenotype in the FH deficient cells (FIG. 3J) as well as the HR defect induced by succinate or fumarate, as measured in the DR-GFP assay (FIG. 3L).

In certain embodiments, the HR defect conferred by SDH or FH deficiency renders cells sensitive to DNA damaging agents. Clonogenic survival assays were performed, which showed that upon SDHB or FH knockdown cells have substantially reduced survival in response to IR, mitomycin C, cisplatin, and etoposide compared to the control shRNA (FIGS. 7A-7D).

Figure 4A:
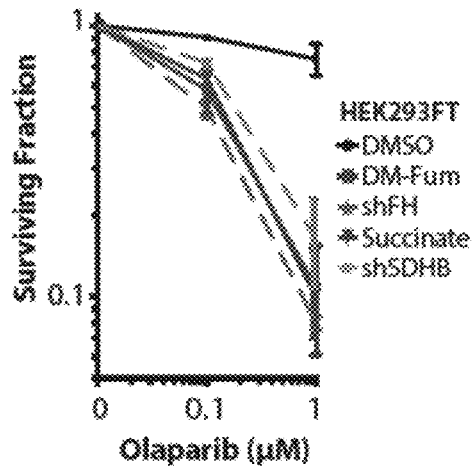
FIGS. 4A-4N: SDHB or FH deficiency confers PARP inhibitor sensitivity on human cells in culture and human tumor xenografts in mice.
Figure 4B:
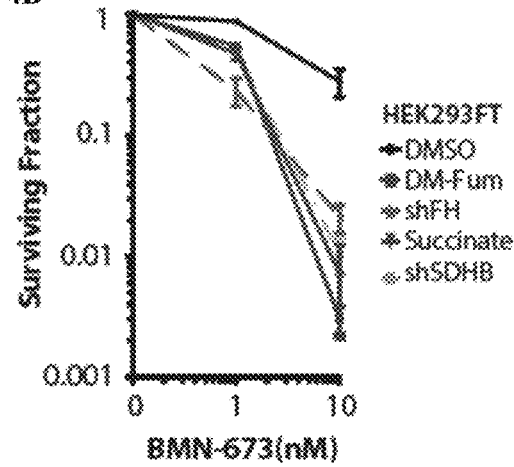
Figure 4C:
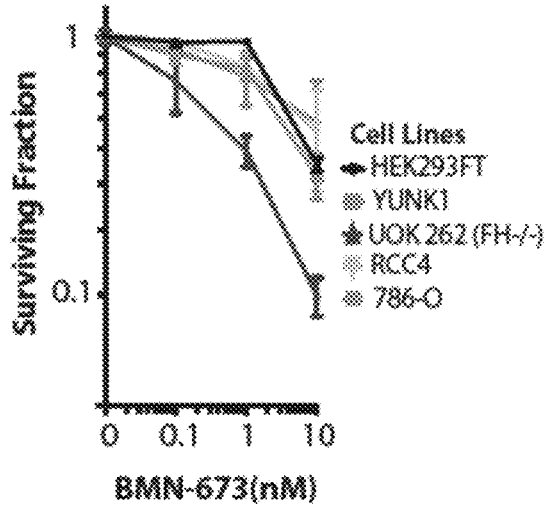
FIG. 4C: Clonogenic survival assays in response to the indicated doses of BMN-673 in cell lines of renal origin. For FIGS. 4A-4C, dots represent mean of 3 independent replicates±SEM.
Figure 8L:
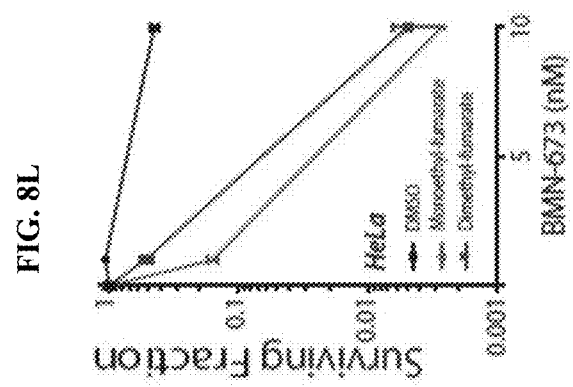
Figure 8K:
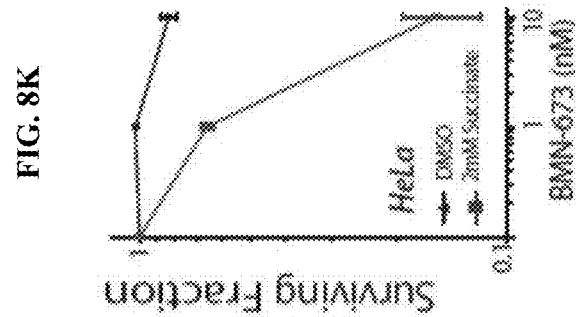
Figure 8J:
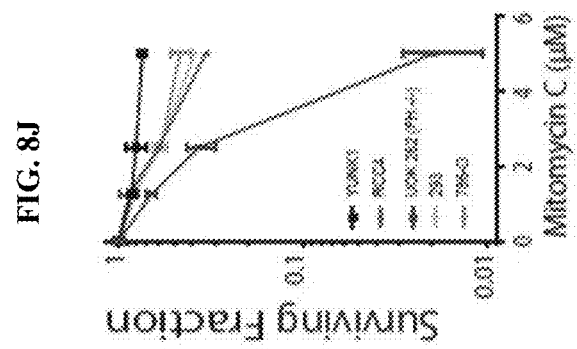
Figure 8I:
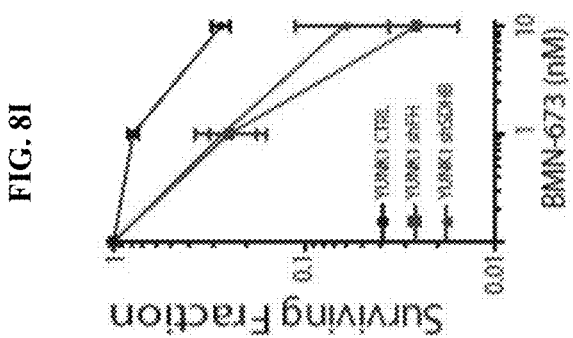

Clinically, an emerging strategy in the treatment of HR deficient cancers is the use of PARP inhibitors (PARPi), which recently have been approved by the FDA for use in patients BRCA1/2 deficient cancers. The effects of fumarate and succinate on PARPi sensitivity were tested. Knockdown of SDHB and FH as well as addition of exogenous dimethyl-fumarate or succinate to the culture media induced dramatic sensitivity to the PARP inhibitors, olaparib and BMN-673 (FIGS. 4A-4B and FIGS. 8E-8I). The FH-deficient HLRCC cell line, UOK 262, was markedly more sensitive to the PARPi, BMN-673 (FIG. 4C) (and to mitomycin C; FIG. 8J) than other cell lines of renal origin that are FH-proficient. Exogenously added succinate and fumarate analogs also strongly sensitized HeLa cells to PARPi as well (FIGS. 8K-8L).

Figure 4D:
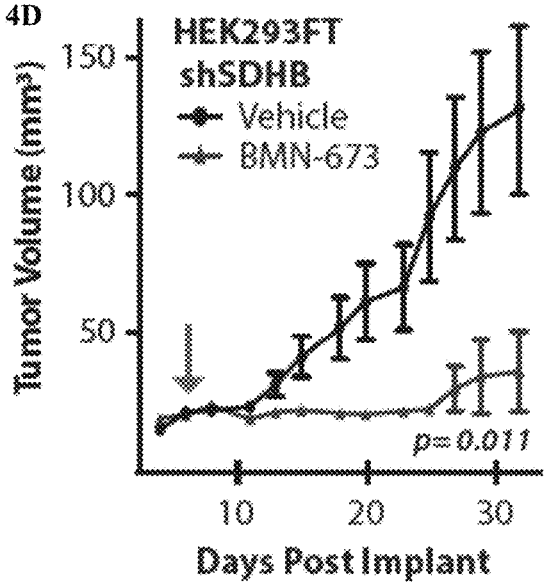
FIGS. 4D-4F: Tumor growth delay assay in shSDHB-expressing (F (1, 234)=40.61) (FIG. 4D), shFH-expressing (F (1, 144)=15.71) (FIG. 4E) and non-targeted control shCTRL-expressing (F (1, 234)=0.27) (FIG. 4F) HEK293FT tumor xenografts in nude mice treated with BMN-673 or vehicle control.
Figure 4E:
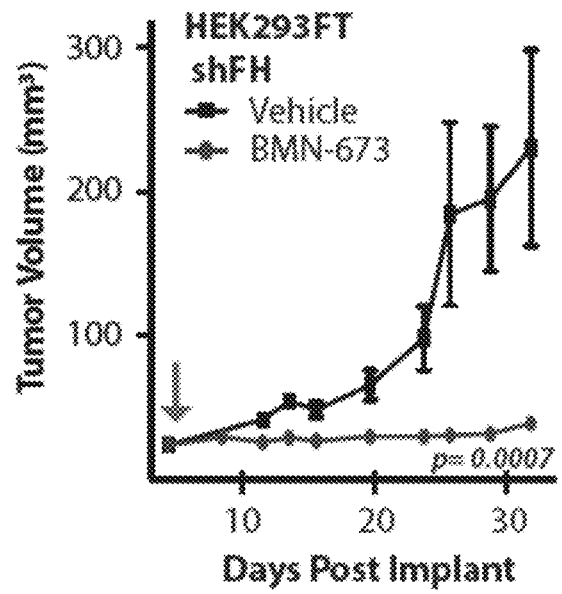
Figure 4F:
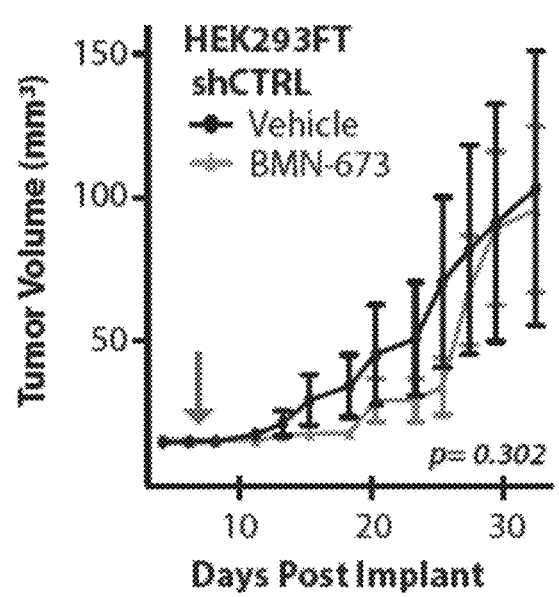
Figure 4G:
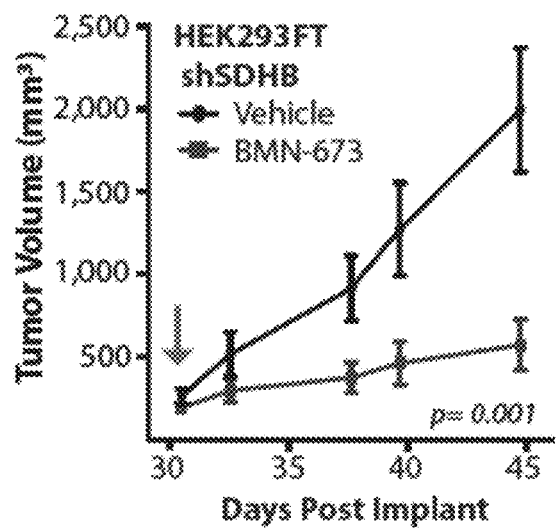
FIGS. 4G-4I: Tumor growth delay assay in shSDHB-expressing (F (1, 90)=28.58) (FIG. 4G), shFH-expressing (F (1, 126)=20.49) (FIG. 4H), and non-targeted control shCTRL (F (1, 90)=4.23) (FIG. 4H)-expressing HEK293FT xenograft tumors treated with BMN-673 or vehicle control. Treatment was initiated when tumors had reached an average size of 95-150 mm$^3$ (arrow). There were 10 animals per group for FIGS. 4D-4F and 10 animals per groups for FIGS. 4G-4I each harboring a single tumor.
Figure 4H:
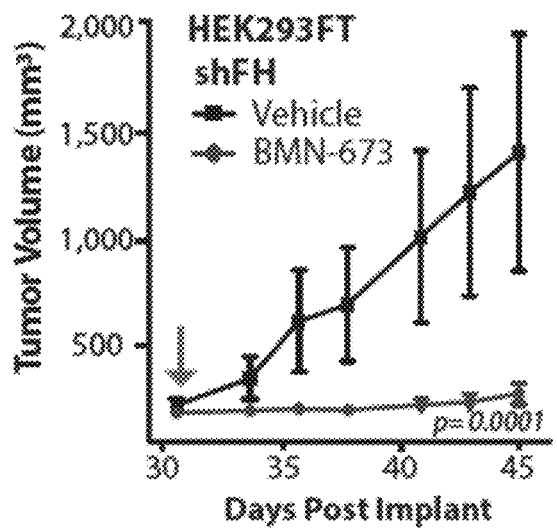
Figure 4I:
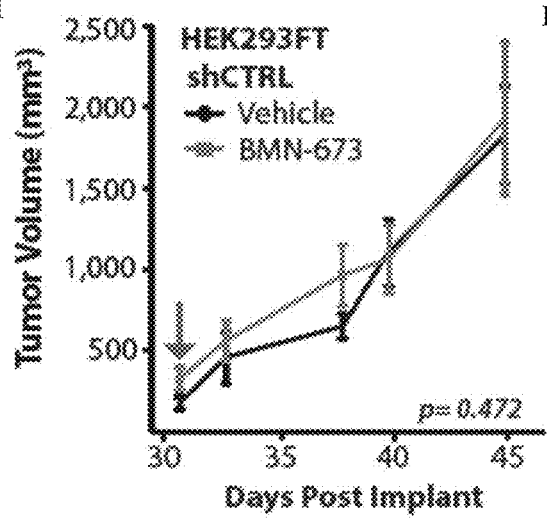
Figure 4J:
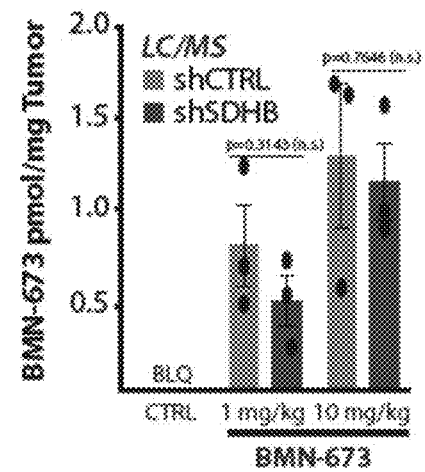
FIG. 4J: LC/MS quantification of BMN-673 accumulation in HEK293FT shSDHB and shRNA control xenograft tumors (approximate size at treatment of 80 mm$^3$) 24 h after treatment of mice with a single dose of BMN-673, as indicated, bars represent mean±SEM, n=3. Statistical analysis by two-sided t-test, df=4.
Figure 4K:
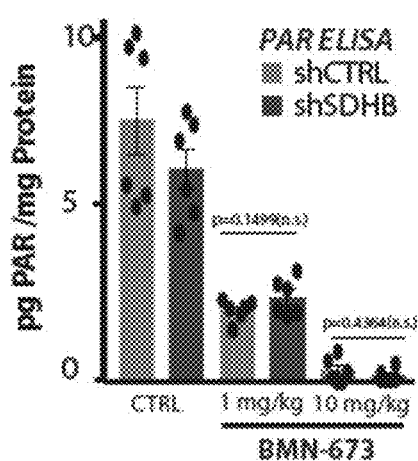
FIG. 4K: Quantification by ELISA of total poly-ADP-ribose (PAR) levels in HEK293FT shSDHB and shRNA control xenograft tumors 24 h after treatment with a single dose of BMN-673, bars represent mean±SEM, n=6, statistical analysis by two-sided t-test, df=10.
Figure 5G:
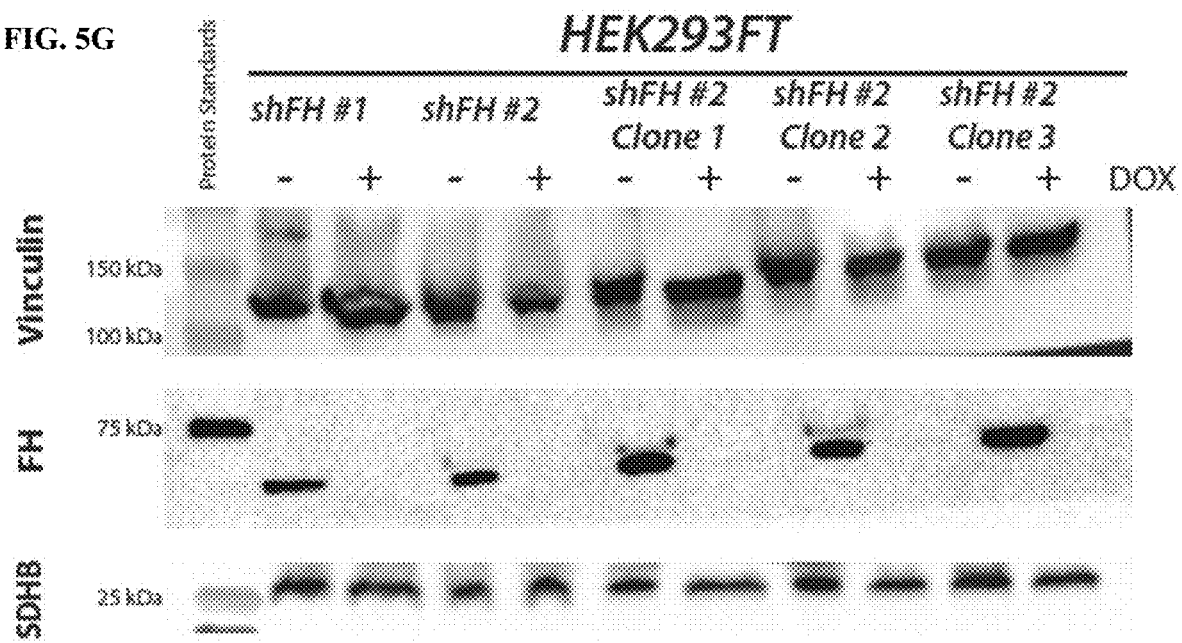
Figure 5H:
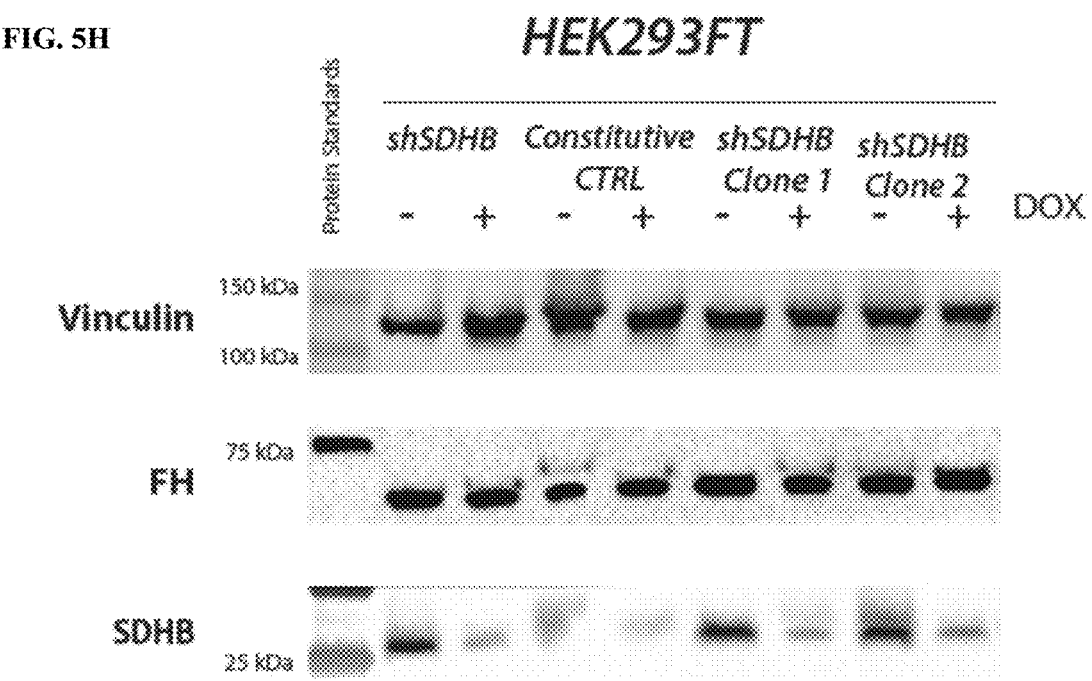
Figure 5I:
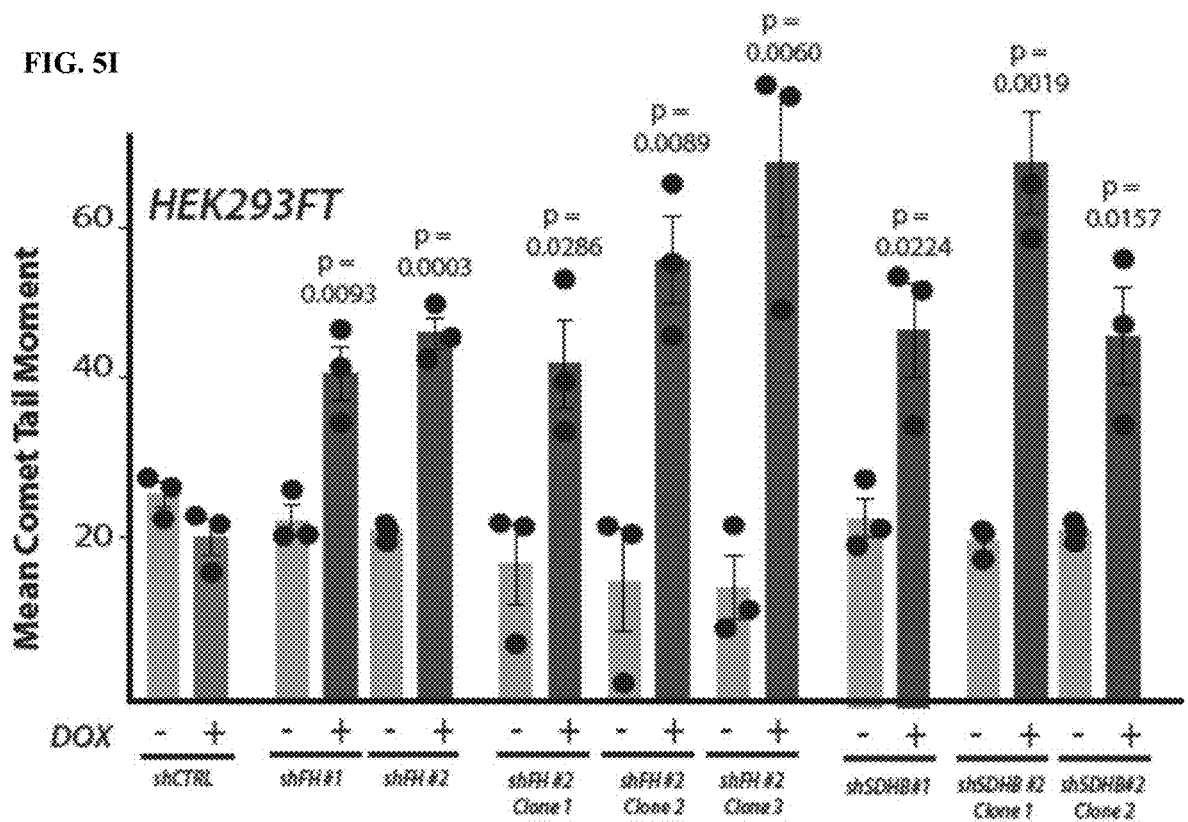
Figure 5M:
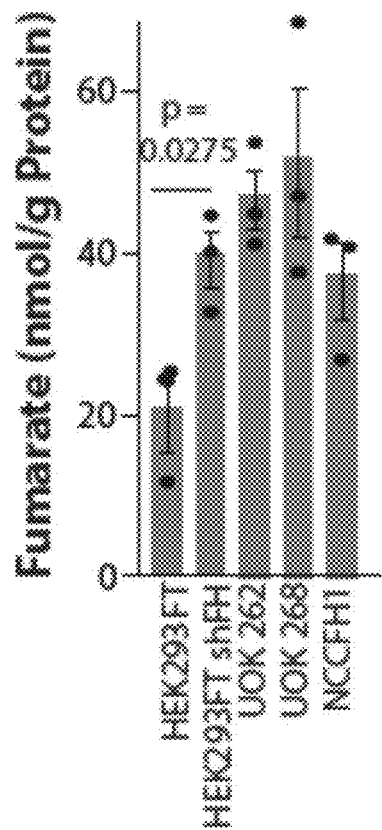
Figure 5N:
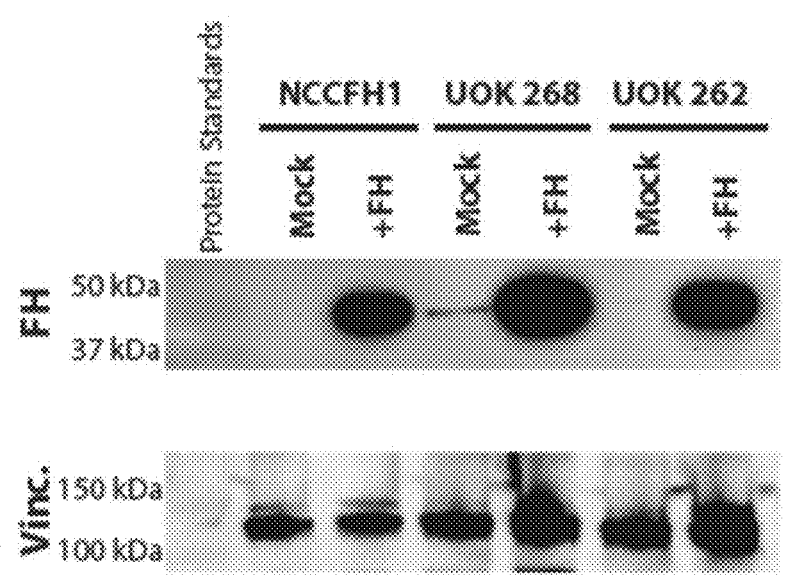
Figure 5O:
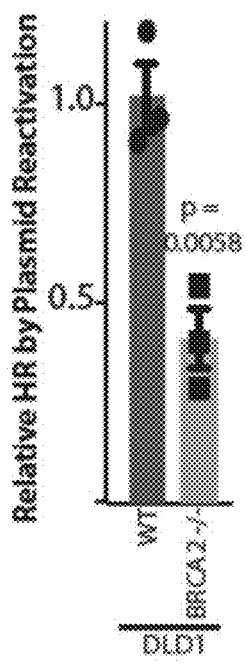
Figure 5P:
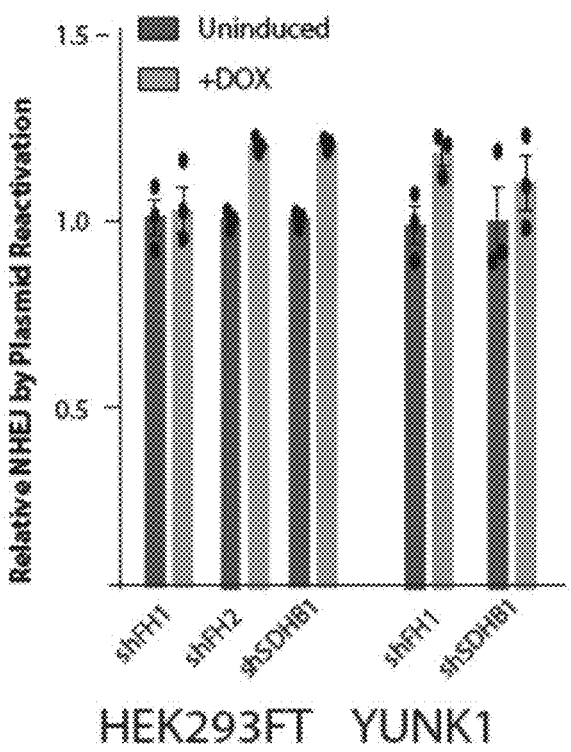
Figure 9B:
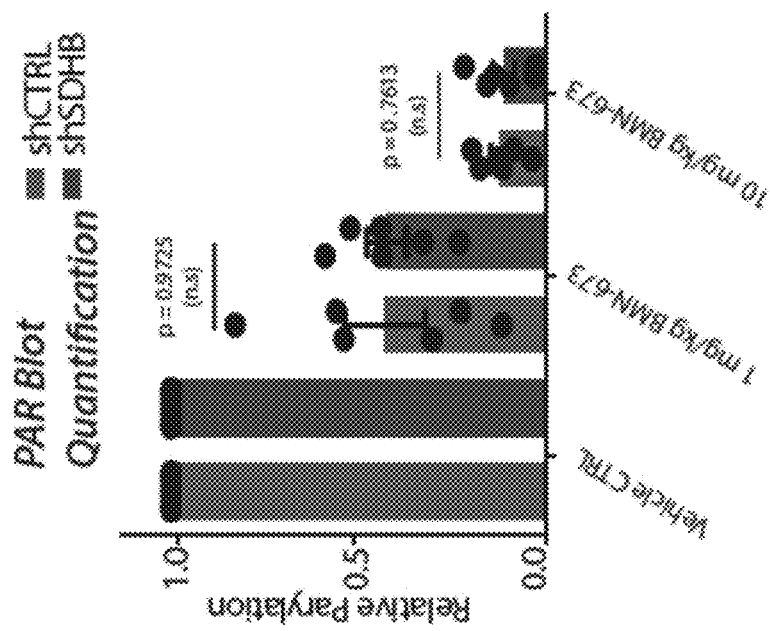
FIGS. 9A-9B: PAR levels determined by western blotting.
Figure 9A:
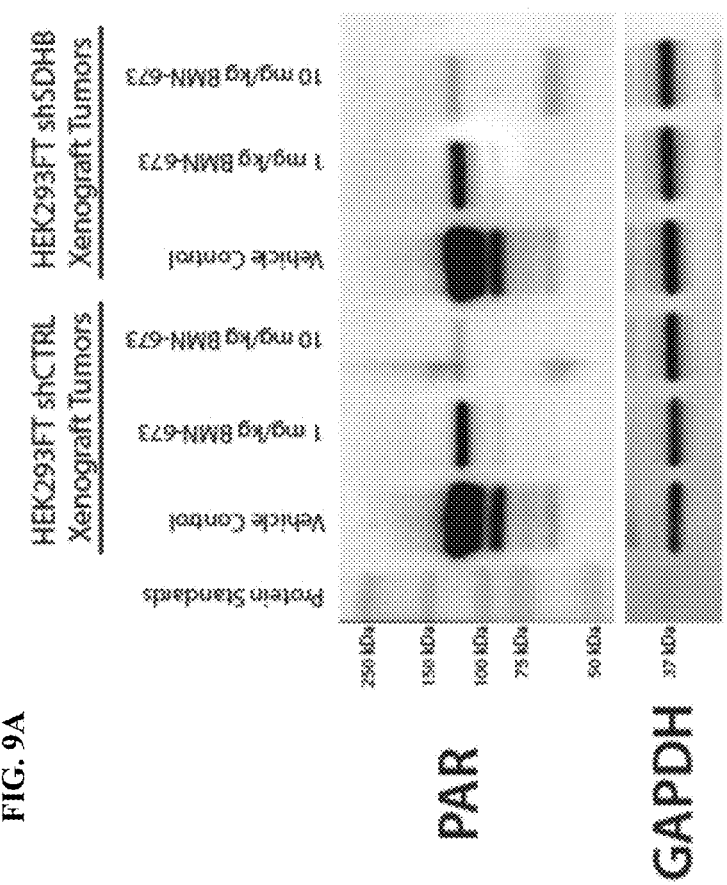

To test for this succinate and fumarate-induced PARPi sensitivity in tumors in vivo, the effect of the PARP inhibitor, BMN-673, on the growth of tumor xenografts formed in immune deficient mice by HEK293FT cells expressing either a non-targeting control shRNA (shCTRL), an shRNA to SDHB (shSDHB), or an shRNA to FH (shFH) (knockdown is shown in FIGS. 5G-5H) was assayed (HEK293FT is a tumorigenic cell line transformed by expression of SV40 Large T antigen). BMN-673 significantly inhibited the growth of both the SDHB-deficient and FH-deficient tumors in two separate sets of in vivo efficacy studies. In one set, mice were treated beginning four days after tumor cell implantation, showing robust suppression of tumor growth by the PARPi compared to the vehicle control in the shSDHB and shFH tumors with no effect in the shCTRL tumors (FIGS. 4D-4F). In the second set, the mice were treated after the tumors had grown to a palpable size (95-150 mm$^3$) (FIGS. 4G-4I). Again, BMN-673 inhibited the growth of the SDH-deficient and FH-deficient tumors (FIGS. 4G and 4H), but there was no growth inhibition relative to vehicle control in xenografts formed from the HEK293FT cells expressing the control shCTRL (FIG. 4I). Quantification of intra-tumoral BMN-673 levels 24 h after treatment by LC/MS showed no significant difference in drug levels between shSDHB and shCTRL HEK293FT tumors (FIG. 4J). In keeping with this, levels of poly-ADP-ribose (PAR) modification of cellular proteins as measured by ELISA (FIG. 4K) and by western blot (FIGS. 9A-9B) were reduced to the same extent 24 h post BMN-673 treatment in the SDHB knockdown tumors as in the shCTRL tumors.

Figure 4L:
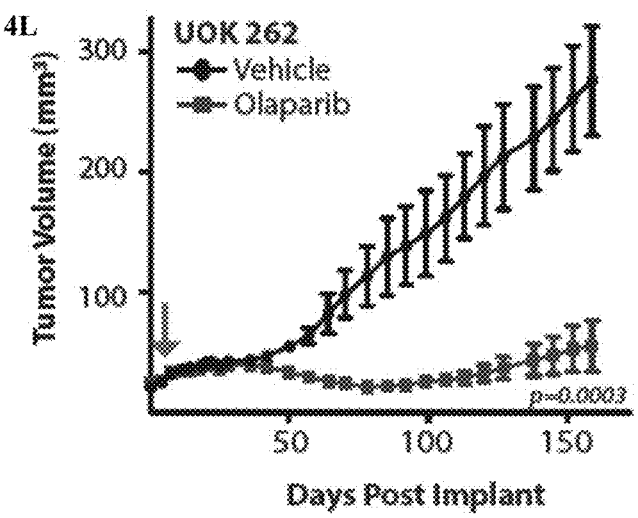
FIG. 4L: Tumor growth delay assay in patient-derived, HLRCC UOK 262 xenograft tumors in nude mice treated with Olaparib or vehicle control starting 4 days after implantation (arrow)(F (1, 532)=185.2).
Figure 4M:
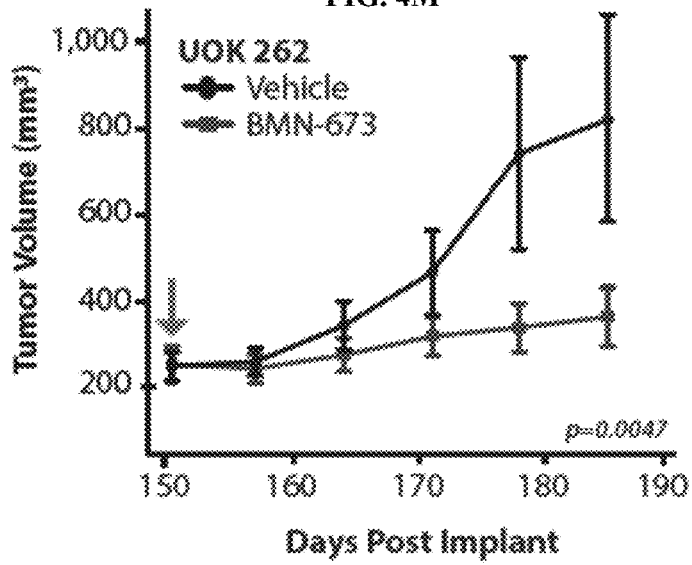
FIG. 4M: Tumor growth delay assay in patient-derived, HLRCC UOK 262 xenograft tumors in nude mice treated with BMN-673 or vehicle control starting once tumors reached an average size of 250 mm$^3$ (F (1, 48)=8.79). For FIG. 4L, 10 mice per group and for FIG. 4M, 6 mice per group. For all tumor growth delay curves shown in FIGS. 4D-4I and 4L-4M dots represent mean±SEM, and the p values were determined by ANOVA. For FIGS. 4D-4I and 4L-4M arrows represent treatment start.

Next, a third in vivo efficacy study was conducted using tumors formed from the UOK 262 cells, that, as discussed above, are an HLRCC patient-derived cell line deficient in FH. A significant growth delay was observed with PARPi treatment administered daily to the mice beginning 4 days after implantation and it continued on a long-term basis for 180 days (FIG. 4L). In a fourth in vivo experiment, mice were treated with BMN-673 or with vehicle control beginning when the UOK 262 xenografts had reached an average size of 250 mm$^3$ (after approximately 150 days of pretreatment growth). Again, the PARPi treatment (but not vehicle control) resulted in a substantial growth delay in the FH-deficient tumors (FIG. 4M). Together, these four in vivo tumor efficacy studies consistently show that PARPi treatment suppresses the growth of SDH- or FH-deficient tumors in mice.

Figure 4N:
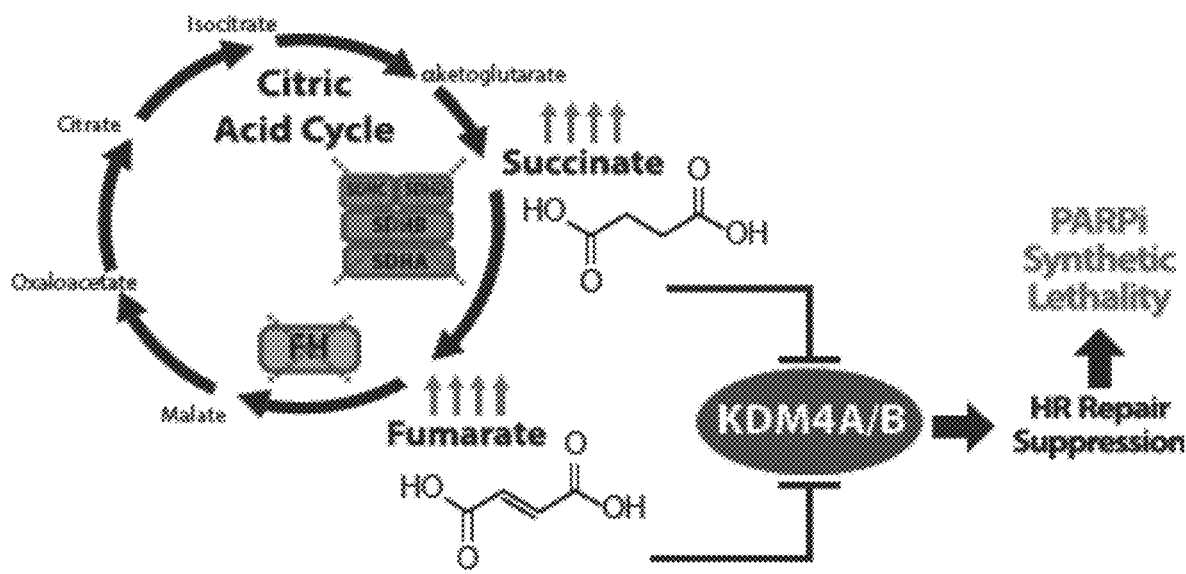

The results presented here demonstrate that the metabolites overproduced in the hereditary cancer syndromes, HLRCC and SDH PGL/PCC, compromise HR DNA repair (FIG. 4N). This finding identifies decreased DNA repair as a key oncogenic mechanism in these diseases much like the familial breast and ovarian cancer predisposition syndromes linked to the BRCA1/2 genes. In addition, our finding that succinate and fumarate render tumor cells highly susceptible to synthetic lethal targeting with PARP inhibitors provides a novel therapeutic strategy that could potentially be translated into the clinic for these otherwise difficult to treat malignancies.

The invention includes compositions and methods for treating or preventing cancer in a subject. In another aspect, the invention provides a pharmaceutical composition comprising an anti-tumor effective amount of at least one compound comprising fumarate, succinate, and/or analogues or derivatives thereof.

The invention includes a method of treating or preventing cancer in a subject in need thereof, wherein the cells in the cancer comprise a FH and/or SDH mutation. The method comprises administering to the subject at least one compound comprising a DNA repair inhibitor. Notwithstanding the aforementioned methods, the invention also includes a method of treating a cancer in a subject, where the cells of the cancer do not contain a FH and/or SDH mutation. The method comprises administering to the subject a therapeutically effective amount of at least one compound selected from the group consisting of fumarate, succinate, and/or an analogue or derivative thereof.

In certain embodiments, the methods of the invention further comprises administering to the subject a therapeutically effective amount of at least one compound comprising a DNA repair inhibitor, whereby the cancer is treated or prevented in the subject.

In certain embodiments, the at least one compound inhibits DNA double strand break repair in the cancer. In certain embodiments, the at least one compound inhibits a serine/threonine kinase, a PIKK protein kinase, a DNA-PK, an ATM or an ATR.

In other embodiments, the at least one compound inhibits homology recombination DNA repair in the cancer. In yet other embodiments, the at least one compound is a poly (ADP-ribose) polymerase (PARP) inhibitor selected from the group consisting of olaparib, Iniparib, Niraparib, Veliparib, Rucaparib, 3-aminobenzamide and BMN-673 (Talazoparib).

In further embodiments, the at least one compound is an alpha-ketoglutarate-dependent dioxygenase A or B (KDM4A or KDM4B) inhibitor selected from the group consisting of DMOG, NSC 636819, PK 118 310, NCGC 00247751, NCGC 00244536, NCGC 00247743, IXO1, Disulfiram and JIB04. PARP inhibitors and KDM4A/KDM4B inhibitors are well known and commonly used in the art. Any of these inhibitors or any derivatives therefrom are suitable for use in the methods of the invention.

In certain embodiments, the subject is further administered at least one additional antitumor agent. In other embodiments, the antitumor agent is selected from the group consisting of topoisomerase inhibitors; alkylating agents; nitrosoureas; antimetabolites; antitumor antibiotics; antimicrotubule agents; hormonal agents; DNA strand break inducing agents; epidermal growth factor (EGF) receptor inhibitors and ant-EGF receptor antibodies; AKT inhibitors; mTOR inhibitors; CDK inhibitors; receptor tyrosine kinase (RTK) inhibitors; ribonucleotide reductase inhibitors; serine/threonine kinase inhibitors, phosphatidyl inositol 3-kinase-like (PIKK) protein kinase inhibitors, DNA dependent protein kinase (DNA-PK) inhibitor, Ataxia Telangiectasia Mutated (ATM) inhibitors, Ataxia Telangiectasia and Rad3 Related (ATR) inhibitors and immune checkpoint inhibitors. In yet other embodiments, administration of the at least one compound and at least one additional antitumor agent is synergistic. In yet other embodiments, the at least one compound and at least one additional antitumor agent are coadministered to the subject. In yet other embodiments, the at least one compound and at least one additional antitumor agent are coformulated so that they are combined into a single pharmaceutical compound.

In certain embodiments, the subject is further administered radiation therapy. In other embodiments, administration of the at least one compound and the radiation therapy is synergistic.

In certain embodiments, the at least one compound is administered to the subject through a route selected from the group consisting of oral, transdermal, transmucosal, intravesical, intrapulmonary, intraduodenal, intragastrical, intrathecal, subcutaneous, intramuscular, intradermal, intraarterial, intravenous, intrabronchial, inhalation, pleural, peritoneal, subcutaneous, epidural, otic, intraocular, and topical.

In certain embodiments, the cancer comprises breast cancer, prostate cancer, ovarian cancer, cervical cancer, skin cancer, pancreatic cancer, colorectal cancer, renal cancer, liver cancer, brain cancer, glioma, glioblastoma multiforme, melanoma, lymphoma, acute myeloid leukemia (AML), cholangiocarcinoma, leukemia, lung cancer, endometrial cancer, head and neck cancer, sarcoma, multiple myeloma and/or neuroblastoma. In other embodiments, the cancer comprises glioma or leukemia. In yet other embodiments, the cancer comprises cells defective in at least one protein selected from the group consisting of BRCA1, BRCA2, PTEN, ATM, ATR, PALB2, FANCD2, RAD50, RAD51, other components of the homology dependent DNA repair pathway or the non-homologous end joining pathway or other components that mediate or regulate DNA repair.

n other aspects, the cancer comprises brain, head and neck cancer, glioma, meningioma, glioblastoma multiforme, lymphoma, leukemia, AML, cholangiocarcinoma, multiple myeloma and neuroblastoma. In yet other aspects, the cancer comprises glioma or AML.

In certain embodiments, the subject is a mammal. In other embodiments, the mammal is a human.

Pharmaceutical compositions comprising at least one compound of the invention, as well as at least one pharmaceutically acceptable carrier, are also contemplated in the invention. Pharmaceutical compositions comprising at least one compound of the invention and at least one additional antitumor agent, as well as at least one pharmaceutically acceptable carrier, are also contemplated in the invention.

Combination Therapies

In certain embodiments, the compounds of the invention are useful in the methods of the invention in combination with at least one additional antitumor compound. This additional compound may comprise compounds identified herein or compounds, e.g., commercially available compounds, known to treat, prevent or reduce the symptoms of cancer.

In one aspect, the present invention contemplates that a compound useful within the invention may be used in combination with a therapeutic agent such as an antitumor agent, including but not limited to a chemotherapeutic agent, an anti-cell proliferation agent or any combination thereof.

For example, any conventional chemotherapeutic agents of the following non-limiting exemplary classes are included in the invention: topoisomerase inhibitors; alkylating agents; nitrosoureas; antimetabolites; antitumor antibiotics; antimicrotubule agents; hormonal agents; DNA strand break inducing agents; EGF receptor inhibitors and anti-EGF receptor antibodies; AKT inhibitors; mTOR inhibitors; CDK inhibitors; receptor tyrosine kinase (RTK) inhibitors; ribonucleotide reductase inhibitors; serine/threonine kinase inhibitors, phosphatidyl inositol 3-kinase-like (PIKK) protein kinase inhibitors, DNA dependent protein kinase (DNA-PK) inhibitors, Ataxia Telangiectasia Mutated (ATM) inhibitors, and Ataxia Telangiectasia and Rad3 Related (ATR) inhibitors.

Topoisomerase inhibitors include etoposide, camptothecin, topotecan, irrinotecan, teniposide, and mitoxantrone.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Antimetabolites prevent incorporation of bases into DNA during the synthesis (S) phase of the cell cycle, prohibiting normal development and division. Non limiting examples of antimetabolites include drugs such as 5-fluorouracil, 6 mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Antimicrotubule agents include plant alkaloids that inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids. The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

DNA strand break inducing agents include bleomycin, doxarubicine, daunorubicine, idarubicine, and mitomycin.

Miscellaneous agents include chemotherapeutics such as hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In certain embodiments, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In other embodiments, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

A "synergistic effect" as used herein relates to an effect of two or more compounds on a subject where the effect of the combination is greater than the sum of their individual effects. A synergistic effect may be calculated, for example, using suitable methods such as, for example, the Sigmoid-$E_{max}$ equation (Holford & Scheiner, 19981, Clin. Pharmacokinet. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively. In some aspects, the effect of treatment of the subject in need thereof with a combination of the compound of the invention an additional antitumor agent (e.g. PARP inhibitor) is.

Kits

The invention includes a kit comprising at least a compound of the invention, an applicator, and an instructional material for use thereof. The instructional material included in the kit comprises instructions for preventing or treating a cancer with cells containing a FH and/or SDH mutation contemplated within the invention in a subject. The instructional material recites the amount of, and frequency with which, the at least one compound of the invention should be administered to the subject. In other embodiments, the kit further comprises at least one additional antitumor agent.

Patient Selection and Monitoring

Described herein are compositions and methods for treating or preventing a cancer in a subject in need thereof wherein the cancer contains a mutation contemplated herein. In some embodiments, the compositions and methods of this inventions are useful for a subject who is at risk of developing cancer associated with a mutation contemplated herein. In some embodiments, a subject is selected for treatment with a compound described herein based on a determination that the subject has a mutant enzyme (such as but not limited to FH and/or SDH). In some embodiments, the subject or a sample (e.g., tissue or bodily fluid) therefrom is evaluated for the presence or amount of a substrate, cofactor and/or product of the enzyme. The presence and/or amount of substrate, cofactor and/or product can correspond to the wild-type/non-mutant activity or can correspond to the mutated form of the enzyme. Exemplary bodily fluids that can be used to identify and evaluate the enzyme include but are not limited to amniotic fluid surrounding a fetus, aqueous humour, blood (e.g., blood plasma), serum, Cerebrospinal fluid, cerumen, chyme, sperm, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

In some embodiments, a subject can be evaluated for carrying an enzyme mutation using any methods known to one skilled in the art by way of non-limiting example: magnetic resonance, chemical assays (e.g., High performance liquid chromatography (HPLC)), sequencing and PCR. In other embodiments, the subject can be evaluated for the presence of and/or an elevated amount of succinate and/or fumarate relative to the amount of succinate and/or fumarate present in a subject who does not have a certain enzyme mutation.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or rophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limitin example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRYTM White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Solutions, suspensions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 min up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 min, about 20 min, or about 10 min and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 min, about 20 min, or about 10 min, and any and all whole or partial Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods

Western Blot analyses. Western blot analysis of protein levels was conducted by loading 30 µg of whole cell lysate onto a 4-20% polyacrylamide gel. Total protein was transferred to a nitrocellulose membrane. After blocking with 5% milk, membranes were incubated with primary antibodies. Antibodies used were: Rabbit monoclonal anti-Fumarase (D9C5,Cell Signaling Technologies) 1:1000 in 5% BSA, mouse monoclonal anti-SDHB (21A11AE7, Abcam) 1:1000 in % 5 milk, mouse monoclonal anti-Vinculin (SPM227, Abcam) 1:1000 in 5% milk, rabbit polyclonal anti-Histone 3 Lysine 36 trimethyl (9050, Abcam) 1:500 in 5% BSA, anti-Histone 3 Lysine 9 trimethyl (D4W1U, Cell Signaling Technologies) 1:1000 in 5% BSA, mouse monoclonal anti-Beta Actin (60008, Protein Tech) 1:5000 5% milk, rabbit Polyclonal anti-Histone H3 (ab1791, Abcam 1:5000 5% BSA), rabbit Polyclonal anti-PAR (4336-BPC-100, Trevigen) 1:5000 5% BSA, mouse monoclonal anti-GAPDH (60004 Protein Tech) 1:5000 5% milk, mouse monoclonal anti-BRCA2 (ab1, Millipore, 1:1000 5% Milk), mouse monoclonal anti-BRCA1 (D-9, Santa Cruz, 1:200 5% milk), mouse monoclonal anti-RAD51(14B4 Novus bio, 1:1000 5% milk). Patient sample blots were reprobed. Reprobed blots were stripped with Restore Plus Stripping Buffer (Thermo Fischer) and re-blocked with 5% milk prior to reprobing. Blots were tested to ensure all residual detection reagents were removed. Dual Color Precision Plus Protein standard was used as a molecular weight standard for western blots.

Cell Culture. YUNK1 cells were generated in culture from uninvolved cortical renal tissue from a patient undergoing a radical nephrectomy for kidney cancer. This cell line was grown in DMEM with 10% FBS and was capable of 10 passages before senescence. YUNK1 was immortalized with a lentiviral vector containing SV40 Large T antigen (Addgene plasmid #22298). Lentiviral production was performed using HEK293FT (ATCC) using plasmids pMDLg/pRRE, pRSV-Rev, pCMV-VSG-G (Addgene #12251, 12253, and 8454). YUNK1 cells were maintained in DMEM+10% FBS+1% Pen/Strep. HEK293FT cells (ATCC) were maintained in DMEM+10% FBS+1% Pen/Strep. After lentiviral infections with TRIPZ-shRNA or GIPZ lentiviruses, cells were maintained in DMEM+10% FBS+1% Pen/Strep+2 µg/mL Puromycin. For dox inducible shRNAs, expression was induced with 2 µg/mL doxycycline. Doxycycline induced knockdown was monitored by western blot as well as by RFP fluorescence from the internal and dox-inducible reporter on the TRIPZ construct. U2OS DR-GFP cells were maintained in DMEM+10% FBS+1% Pen/Strep. UOK 262 and UOK 268 HLRCC cells are previously described in Yang, et al., 2010, Cancer Gent. Cytogent. 196:45-55; Yang, et al., 205, Cancer Genet. 205:377-390. They were obtained courtesy of W. M. Linehan and were maintained in DMEM+ 10% FBS+1% Pen/Strep+1 mM Sodium-Pyruvate. NCCFH1 cells were maintained in DMEM+10% FBS+1% Pen/Strep+1 mM Sodium-Pyruvate. Hela cells (ATCC), RCC4 (ATCC) and 786-0 (ATCC) were maintained in DMEM+10% FBS+1% Pen/Strep.

Chemicals: Succinate (S9512, Sigma), monoethyl-succinate (475505, Sigma), dimethyl-succinate (112755, Sigma), monoethyl-fumarate (128422, Sigma), dimethyl-fumarate (242926, Sigma), and dimethyl-alpha-ketoglutarate (349631, Sigma) were obtained from Sigma Aldrich.

shRNA. Doxycycline-inducible shRNA knockdowns were made using TRIPZ doxycycline-inducible shRNA lentiviruses available from Ge Dharmacon. Lentiviral particles were produced using plasmids pMDLg/pRRE, pRSV-Rev, pCMV-VSG-G (Addgene #12251, 12253, and 8454). The TRIPZ shRNA clones used were as follows, shFH #1: Ge Dharmacon, V3THS_324846, TRIPZ shFH #2: Ge Dharmacon, V3THS_324847. TRIPZ shSDHB #1: Ge Dharmacon, V3THS_346327, TRIPZ shSDHB #2: Ge Dharmacon, V3THS_347328, and TRIPZ non-targeting control (RHS4743, Ge Dharmacon). Pooled populations and single cell clones were selected with 2 µg/mL Puromycin and maintained in selective media. Single cell clones were derived by limiting dilution. shRNA expression was induced with 1 µg/mL Doxycline for 4 days before starting an assay, and repression of the target proteins was routinely monitored by western blot. Constitutive shRNA knockdown shRNA lentivirus were produced using identical protocols using the GIPZ lentiviral constructs, for shFH #1: Ge Dharmacon, V2LHS_83495, shFH #2 Ge Dharmacon, V3LHS_403312, shSDHB #1 Ge Dharmacon, V3LHS_346327, shSDHB #2

Ge Dharmacon, V3LHS_346329 and GIPZ non-targeting control (RHS4348, Ge Dharmacon). Cells were selected in 2 µg/mL Puromycin and maintained in selective media and clones were isolated by limiting dilution in selective media. Neutral comet assays. Neutral comet assays were performed as previously described in Sulkowski, et al., 2017, Science Transl. Med. 9:eaa12463. Patient tumor samples were processed one at a time, diced with a razor blade on ice to dissociate the cells in cold PBS, counted and suspended in low-melt agarose at a concentration of 2000 cells per assay. Upon solidification of the agarose, the cells were immediately lysed and the neutral comet assay was performed as previously described (Sulkowski, et al., 2017, Science Transl. Med. 9:eaa12463). Neutral comet assays on cell line samples were performed as previously described (Sulkowski, et al., 2017, Science Transl. Med. 9:eaa12463). For doxycycline-inducible shRNA of FH and SDHB, the assays were performed 5 days after induction of shRNA with 2 µg/mL Doxycycline. For plasmid transfection assays, $1\times10^5$ cells per well were seeded in a 12-well dish and allowed to attach overnight. The next day the cells were transfected with 1 µg of pCMV-FH (Origene), pCMV-HA-JMJ2A (KDM4A) (Addgene), pCMV-HA- MJ2B (KDM4B) (Addgene), or pCMV-HA-GASC1 (KDM4C) (Addgene) using 1 µL of Lipofectamine 3000 and 1 µL of p3000 reagent. 48 h later cells were collected on ice, suspended in PBS, and then adjusted to a concentration of 2000 cells per assay in low melt agarose. For assays following treatment with exogenous metabolites, these were added 24 h before performing the neutral comet assay. Data are presented as means of three biological replicates±SEM. Replicates reflect independent cultures for in vitro assays. For analysis for patient samples, 3 replicates were performed on each patient tissue sample. siRNA. siRNA transfections were carried out with Dharmafect 2 (GE Dharmacon) per manufacturers protocol with final siRNA concentration at 20 nM for all assays. siRNAs used were ON-TARGET Plus siRNA targeting BRCA1 (GE Dharmacon, L-003461), RAD51 (GE Dharmacon, L-003530), BRCA2(L-003462, GE Dharmacon), SDHB (GE Dharmacon, L-011773), FH (L-009512, GE Dharmacon) and the ON-TARGET Plus siRNA non-targeting control (GE Dharmacon, D-001810)

γH2AX ELISA. FFPE samples were collected as a 10 µM slice off the tissue block. Samples were deparaffinized with 3 washes in 1 mL xylene. Samples were then washed 3 times in 100% Ethanol, followed by 3 washes in 85% Ethanol and 3 washes in 70% Ethanol. Samples were then incubated in extraction buffer (20 mM TRIS pH 8.8, 100 mM DTT, 2% SDS) and incubated at 100° C. for 20 min, followed by a −20° C. The γH2AX ELISA assay was performed using the γH2AX Pharmacodynamic Assay Kit per manufacturers protocol, using an input of 2 µg protein per replicate. Data are presented as means of three biological replicates±SEM. Luciferase-based reporter assays for homology-directed repair and non-homologous end-joining. Briefly, the HR luciferase reporter construct was generated by cloning an inactivating I-SceI recognition site into the BstBI site 56 amino acids into the firefly luciferase gene in the gWIZ.Luciferase vector (Genlantis) and cloning a promoterless copy of the firefly luciferase ORF 700 base pairs downstream in reverse orientation as a donor template for HR. A DSB in the firefly luciferase gene is induced by I-SceI digestion and confirmed by electrophoresis. Linearized plasmid is then transfected into cells to measure HR as a function of luciferase activity (firefly luciferase activity can only be restored by HR, which removes the inactivating I-SceI site). To assay NHEJ, a Hind III-mediated DSB was generated between the promoter and the coding region of the firefly luciferase gene in the pGL3-Control Vector (Promega) and confirmed by electrophoresis. After transfection of linearized plasmid, repair of the DSB by NHEJ restore firefly luciferase activity. All reporter assays were performed in 12-well format by seeding $1\times10^5$ cells per well 24 hours before transfection and transfecting 1 µg of reporter or positive control vector and 50 ng of Renilla luciferase vector (as a transfection control) per well. For HR, cells were analyzed 48 hours after reporter transfection, and for NHEJ, cells were analyzed 24 hours after reporter transfection. Luciferase activity was measured using the Dual-Luciferase Reporter Assay System (Promega) for all samples and normalized to Renilla luciferase signal to control for transfection efficiency, to the positive control luciferase expression vector: gWIZ.luciferase for HR or pG13-Control for NHEJ. Data are presented as means of three biological replicates±SEM.

U2OS DR-GFP assays. U2OS DR-GFP assays were performed as previously described in Sulkowski, et al., 2017, Science Transl. Med. 9:eaa12463. siRNAs were transfected to a final concentration of 20 nM, and cells were assayed 96 h after siRNA transfection. Metabolites were added to the cells at indicated concentration 24h before performing the assay.

Clonogenic survival assay. After 5 days of Doxycycline exposure for the shRNA models, cells in culture were irradiated at varying doses of IR. Four hours after irradiation, they were trypsinized, washed, counted, and seeded in six-well plates in triplicate at threefold dilutions, ranging from 1200 to 300 cells per well. For drug treatments, cells were seeded 24 hours before addition of the drug. PARP inhibitors were added and left on the cells for the duration of the assay. Cisplatin was a 24 h treatment, and MMC and Etoposide were 1 h treatments. For assays that included treatment with exogenous metabolites, these were added 24 h before the drug treatment. Plates were incubated for 10-14 days until colonies formed. Colonies were fixed with 2% formaldehyde, then stained with crystal violet and quantified.

Immunofluorescence and Foci Assays. Primary antibodies: γH2AX antibody mouse (1:400; #05-636; EMD Millipore), phospho-53BP1 rabbit (1:300; #2675; Cell Signaling Technology), Rad51 antibody rabbit (1:300; #PC130-100; EMD Millipore). Secondary antibodies: anti-mouse AF Plus 488, anti-mouse AF Plus 647, anti-rabbit AF Plus 488, anti-rabbit AF Plus 647 (1:400; #A32723, #A32728, #A32731, #A32733; Thermo Fisher Scientific). Cells were seeded in chamber slides. Subsequently, cells were fixed and permeabilized in 3% PFA/0.2% Triton-X100/2% sucrose for 20 min and blocked with 10% bovine serum albumin in PBS overnight at 4° C. Proteins were stained overnight at 4° C. with primary antibodies diluted in blocking solution. Upon three times of washing with 0.5% Triton-X100 in PBS, samples were incubated with secondary antibodies for 90 min at RT. DNA was stained with DAPI (2.5 µg/mL; #1816957; Thermo Scientific Inc) for 20 min at RT. After staining and 3 times washing, chambers were removed from the slides and the slides were covered with coverslips using DAKO Fluorescence Mounting Medium (#S3023; Dako NA Inc.). Images were analyzed with a Nikon Eclipse Ti fluorescence microscope with a Plan Apo 60X/1.40 Oil DIC h objective, a CSU-W1 confocal scanning unit with a iXon Ultra camera (Andor Technology), MLC 400B laser unit (Agilent Technologies) and NIS Elements 4.30 software (Nikon Corporation). Foci were analyzed with the Focinator v2-21 software. RAD51 foci analysis plus radiation was performed 4 h after 2 Gy IR, cells with greater than 20 foci per nucleus were considered RAD51 positive. For γH2AX greater than 15 foci per nucleus were considered foci positive cells and for p53BP1 analysis greater than 5 foci per nucleus were considered foci positive cells.

LC-MS/MS analysis. The concentrations of succinate and fumarate in frozen tissue and cell samples were determined using a validated liquid chromatography-tandem mass spectrometry (LC-MS/MS) method, as described below. The calibration curve was prepared in distilled water, with the concentration range of 0.002-10 μM for succinate and 0.02-100 μM for fumarate. The intra- and inter-day precision and accuracy of the quality control samples met the generally accepted criterial for bioanalytical methods (i.e., <15%).

Sample preparation. Tissue homogenate was prepared by adding 100 μL of distilled water to a weighted tissue sample (~20 mg) followed by homogenization using a PRECELLYS® homogenizer (at 6500 RPM for two 20 seconds with 5 seconds pause). Cell homogenate was prepared by adding 500 μL water into cell pellet (~5 million cells) followed by sonication. Into tissue or cell homogenate (original or 20-fold diluted sample), the stable isotope labeled internal standards, $D_6$-succinate and $1,4^{13}C_2$, $2,3$-$D_2$-fumarate, were added and followed by vortexed-mixing. Then, 60 μL was taken and protein precipitated by adding 240 μL of ice-cold methanol. The supernatant was transferred to a 2-mL Eppendorf tube; 0.1 mL of ice-cold 80% methanol was added to the precipitated pellet followed by vortex-mixing and centrifugation (at 10,000 rpm, 4° C. for 10 min). The supernatants from two extractions were combined, and dried-down using a CENTRIVAP® Refrigerated Centrifugal Concentrator (Kansas City, Mo.) at 10° C. The residue was reconstituted in 60 μL distilled water followed by vortex-mixing and centrifugation, and 5 μL of the supernatant was injected into the LC-MS/MS system.

LC-MS/MS analysis. All LC-MS/MS analyses were performed on an AB SCIEX (Foster City, Calif.) QTRAP 6500 system, which consists of an enhanced high-performance hybrid triple quadrupole/linear ion trap mass spectrometer, interfaced with a SHIMADZU (Kyoto, Japan) Nexera ultra-high-performance liquid chromatography (UHPLC) system. Chromatographic separation was achieved on a Synergi RP column (2.0 mm×150 mm, 4 μm) under a gradient elution consisting of mobile phase A (0.03% formic acid in water) and mobile phase B (0.03% formic acid in acetonitrile), at a flow rate of 0.25 mL/min. Succinate, fumarate, and their respective internal standards were monitored under the negative electrospray ionization mode at the mass transitions of 117.0>73.0, 114.9>71.0, 121.0>76.9, and 119.0>74.0, respectively. ANALYST® 1.6 software was used for system control and data acquisition and MULTIQUANT® 3.0 software was used for data processing and quantitation.

In vivo efficacy studies: HEK293FT xenografts. Female athymic nu/nu mice (Hsd:Athymic Nude-Foxnlnu, Envigo) were used for all in vivo xenograft studies. Mice were quarantined for at least 1 week before experimental manipulation. Tumors were formed using shRNA-expressing versions of the tumorigenic human embryonic kidney cell-derived line, HEK293FT. HEK293FT is a subline of HEK293 cells that has been transformed by expression of SV40 Large T-antigen. TRIPZ-shSDHB, shFH, or shCTRL (non-targeted control) expressing HEK293FT cells were implanted subcutaneously (5×10$^6$ cells in 0.1 cc PBS) in the right flank of nude mice. Two efficacy studies were conducted. In one, mice were randomized into treatment and non-treated groups (10 mice/group) at day 3, with treatment initiation 4 days post implant. In a second independent in vivo efficacy study, mice were injected as above with 10 mice per group, and treatment was started only once the tumor volumes reached 95-150 mm. For both studies, mice were visually observed daily and tumors were measured three times per week by calipers to determine tumor volume using the formula: Volume=L×W×W×0.532. Mice were fed with a grain based rodent diet containing Doxycycline at 200 mg/kg (Bioserv, Catalog #S3888). BMN-673 was solubilized in DMSO and diluted with PBS containing 10% dimethylacetamide (Sigma-Aldrich) and 6% Solutol (Sigma). BMN-673 (0.5 mg/kg, 0.2 cc), or vehicle (0.2 cc) was administered by oral gavage once daily for the duration of the experiment. Mean (geometric) tumor volume (mm$^3$) was plotted over time to monitor tumor growth. P-values were determined by ANOVA with repeated measures.

In vivo efficacy studies: UOK 262 xenografts. Female athymic nu/nu mice (Hsd:Athymic Nude-Foxnlnu, Envigo) were used for all in vivo xenograft studies. Mice were quarantined for at least 1 week before experimental manipulation. UOK 262 cells were implanted subcutaneously using 5×10$^6$ cells in 0.1 cc PBS mixed with 0.1 cc of Corning Matrigel Matrix (Cat. No. 354234) per animal. Mice were randomized at day 3 day into two groups (n=10/group). Olaparib (Selleckchem) was solubilized in DMSO and diluted with 10% (w/v) 2-hydroxy-propyl-beta-cyclodextrin (Sigma) to obtain the desired concentration and delivered via intraperitoneal injection (50 mg/kg) once daily, five days per week. In a second, UOK 262 in vivo efficacy study, mice were randomized into treatment and control groups (n=6 per group) after the volume reached 250 mm. The control group received the vehicle and the other group received BMN-673 (0.5 mg/kg, 0.2 cc) gavage administered daily.

LC/MS analysis of intratumoral BMN-673. Human embryonic kidney cells TRIPZ-shSDHB or shCTRL (non-targeted control) subcutaneously (5×10$^6$ cells in 0.1 cc PBS) in both flanks.

Tumors developed with mice on a rodent diet including doxycycline just as in the in vivo efficacy studies. Once tumors were at 80 mm$^3$ mice were gavaged with BMN-673 at 1 or 10 mg/kg or vehicle. Tumors were collected 24 hours later for and frozen at −80° C. The concentrations of BMN-673 in tumor samples were determined using liquid chromatography with tandem mass spectrometry (LC-MS/MS). In brief, an aliquot (30 μL) tumor homogenate was protein precipitated with volumes of methanol, and 5 μL of supernatant was injected into the LC-MS/MS system. LC-MS/MS analyses were performed on a Waters LC-MS/MS system consisting a Waters AQUITY UPLC system coupled with a TQ-XS triple quadrupole mass spectrometer (Milford, Mass., USA). Chromatographic separation was achieved on an XBridge C18 column (2.1×50 mm, 3.5 μm) using a gradient elution consisting of acetonitrile and 0.1% formic acid in water, at a flow rate of 0.4 mL/min. BMN673 was monitored using the positive electrospray ionization mode at the most sensitive and specific mass transition, m/z 381.0>228.8. The linear calibration curve was established at BMN673 concentration range of 5-5000 nM in mouse serum. The precision and accuracy of quality control samples were within generally acceptable criteria for bioanalytical methods.

Poly-ADP-Ribose ELISA. Poly-ADP-Ribose ELISA was performed per manufacturer's protocol using the PARP in vivo Pharmacodynamic Assay II Kit (Trevigen). 2 μg of protein input was used per replicate and luminescence reading were converted to pg PAR/μg protein using a standard curve.

Statistics and Reproducibility. Data are means±SEM and compared using two-sided t-test, or ANOVA with repeated measures when appropriate. All t-tests were two-sided. Statistical analyses were carried out using GraphPad Prism and Stata software. Replicates were defined as individual cultures for all in vitro assays and statistics were performed on measurements from independent cultures. For in vivo assays replicates were defined as individual mice harboring a xenograft tumor.

The disclosures of each and every patent, patent application, and publication cited herein are hereby incorporated herein by reference in their entirety.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A method of treating or ameliorating a cancer in a mammalian subject in need thereof, the method comprising administering to the subject a therapeutically effective amount of at least one compound selected from the group consisting of a DNA repair inhibitor, a DNA strand break repair inhibitor, and a homologous recombination (HR) repair inhibitor,
   wherein cells in the cancer comprise at least one of a fumarate hydratase (FH) mutation and a succinate dehydrogenase (SDH) mutation.

2. The method of claim 1, wherein the cancer is not one selected from the group consisting of Hereditary Leiomyomatosis and Renal Cell Cancer (HLRCC) and Succinate Dehydrogenase-related Hereditary Paraganglioma and Pheochromocytoma (SDH PGL/PCC).

3. The method of claim 1, wherein the cancer is HLRCC or SDH PGL/PCC.

4. The method of claim 1, wherein the at least one compound comprises
   at least one poly(ADP-ribose) polymerase (PARP) inhibitor selected from the group consisting of olaparib, Iniparib, Niraparib, Veliparib, Rucaparib, 3-aminobenzamide, and BMN-673 (Talazoparib), or
   at least one alpha-ketoglutarate-dependent dioxygenase A or B (KDM4A or KDM4B) inhibitor selected from the group consisting of DMOG, NSC 636819, PK 118 310, NCGC 00247751, NCGC 00244536, NCGC 00247743, IXO1, Disulfiram, and JIB04.

5. The method of claim 1, wherein the subject is further administered at least one antitumor agent.

6. The method of claim 5, wherein the antitumor agent is selected from the group consisting of a topoisomerase inhibitor, an alkylating agent, nitrosoureas, an antimetabolite, an antitumor antibiotic, an antimicrotubule agent, a hormonal agent, a DNA strand break inducing agent, an epidermal growth factor (EGF) receptor inhibitor, an anti-EGF receptor antibody, an AKT inhibitor, an mTOR inhibitor, a CDK inhibitor, a tyrosine kinase receptor (TKR) inhibitor, a serine/threonine kinase inhibitor, a phosphatidyl inositol 3-kinase-like (PIKK) protein kinase inhibitor, a DNA dependent protein kinase (DNA-PK) inhibitor, an Ataxia Telangiectasia Mutated (ATM) inhibitor, an Ataxia Telangiectasia and Rad3 Related (ATR) inhibitor, a ribonucleotide reductase inhibitor, and an immune checkpoint inhibitor.

7. The method of claim 5, wherein treatment of the subject with the at least one compound and at least one antitumor agent is synergistic.

8. The method of claim 5, wherein the at least one compound and at least one antitumor agent are co-administered to the subject.

9. The method of claim 8, wherein the at least one compound and at least one antitumor agent are coformulated for administration to the subject.

10. The method of claim 1, wherein the subject is further administered radiation therapy.

11. The method of claim 10, wherein treatment of the subject with at least one compound and the radiation therapy is synergistic.

12. The method of claim 1, wherein the at least one compound is administered to the subject by a route selected from the group consisting of oral, transdermal, transmucosal, intravesical, intrapulmonary, intraduodenal, intragastrical, intrathecal, subcutaneous, intramuscular, intradermal, intra-arterial, intravenous, intrabronchial, inhalation, pleural, peritoneal, subcutaneous, epidural, otic, intraocular, and topical.

13. The method of claim 1, wherein the cancer comprises at least one selected from the group consisting of brain head and neck cancer, glioma, meningioma, glioblastoma multiforme, lymphoma, leukemia, acute myeloid leukemia (AML), cholangiocarcinoma, multiple myeloma, and neuroblastoma.

14. The method of claim 1, wherein the cancer comprises glioma, acute myelogenous leukemia, or cholangiocarcinoma.

15. The method of claim 1, wherein the mammal is a human.

* * * * *